(12) United States Patent
Cheng et al.

(10) Patent No.: US 8,791,240 B2
(45) Date of Patent: Jul. 29, 2014

(54) AUTO-DEVELOPING AND REGULARLY-WEIGHTED PROTEIN MOLECULAR WEIGHT MARKER KIT AND METHOD FOR PREPARING THE SAME

(75) Inventors: Tian-Lu Cheng, Kaohsiung (TW); Chiu-Min Cheng, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 186 days.

(21) Appl. No.: 13/402,086

(22) Filed: Feb. 22, 2012

(65) Prior Publication Data
US 2013/0217133 A1 Aug. 22, 2013

(51) Int. Cl.
*C07K 1/00* (2006.01)
*C12P 21/04* (2006.01)

(52) U.S. Cl.
USPC .......................................... 530/350; 435/71.1

(58) Field of Classification Search
CPC ................. C12Q 2525/121; C12Q 2525/161; C12Q 2525/205; C12Q 1/6827; A01N 2300/00
See application file for complete search history.

(56) References Cited

PUBLICATIONS

Chang, M. et al., Dye-free protein molecular weight markers, Electrophoresis 2005, 26, 3062-3068.

*Primary Examiner* — Alexander Kim
(74) *Attorney, Agent, or Firm* — WPAT, P.C.; Anthony King

(57) ABSTRACT

The present invention provides an auto-developing and regularly-weighted protein molecular weight marker kit, comprising: (a) a plurality of recombinant proteins having formula (I), $$(B)_m\text{-}A\text{-}(C)_n \qquad (I),$$

wherein A is a polypeptide of SEQ ID NO: 1, B and C are independently any mutually identical or different polypeptides with the value of molecular weight being a multiple of 5, and m and n is independently 0 or any integer larger than 0; and (b) one or more solvents for stabilizing the recombinant proteins. The present invention also provides a method for preparing the auto-developing and regularly-weighted protein molecular weight marker kit.

9 Claims, 13 Drawing Sheets

FIGURE 2 A

15  NdeI — 14 tags — (S) — NheI — XhoI — EcoRI — HindIII — (S)

20  NdeI — 14 tags — XhoI — 1.4KDa — NheI — EcoRI — HindIII — (S)

25  NdeI — 14 tags — XhoI/SalI — EcoRI — TRX — HindIII — (S)

30  NdeI — 14 tags — XhoI — 1.4KDa — NheI — EcoRI — TRX — HindIII — (S)

40  NdeI — 14 tags — XhoI — GST — NsiI — NcoI — HpaI — EcoRV — SalI — EcoRI — (S) — NheI — EcoRI — TRX — HindIII — (S)

50  NdeI — 14 tags — XhoI — GST — NsiI — NcoI — HpaI — EcoRV — SalI — EcoRI — TRX — HindIII — (S)

60  NdeI — 14 tags — XhoI — GST — NsiI — NcoI — HpaI — EcoRV — SalI — TRX — NheI — EcoRI — TRX — HindIII — (S)

80  NdeI — 14 tags — XhoI — GST — NsiI — NcoI — HpaI — MBP — EcoRV — NcoI — HindIII — (S) — EcoRV — SalI — EcoRI — TRX — HindIII — NheI — EcoRI — TRX — HindIII — (S)

100 NdeI — 14 tags — XhoI — GST — NsiI — NcoI — HpaI — MBP — EcoRV — SalI — EcoRI — TRX — HindIII — NheI — EcoRI — TRX — HindIII — (S)

120 NdeI — 14 tags — XhoI — GST — NsiI — NcoI — HpaI — MBP — EcoRV — SalI — EcoRI — (S) — NheI — EcoRI — TRX — HindIII — (S)

160 NdeI — 14 tags — XhoI — GST — NsiI — NcoI — HpaI — MBP — EcoRV — SalI — NsiI — MBP — HpaI — MBP — EcoRV — NcoI — HindIII — (S)

180 NdeI — 14 tags — XhoI — GST — NsiI — MBP — HpaI — MBP — EcoRV — SalI — NsiI — MBP — EcoRV — SalI — EcoRI — TRX — HindIII — NheI — EcoRI — TRX — HindIII — (S)

200 NdeI — 14 tags — XhoI — GST — NsiI — MBP — HpaI — MBP — EcoRV — SalI — NsiI — MBP — HpaI — MBP — EcoRV — NcoI — HindIII — (S)

240 NdeI — 14 tags — XhoI — GST — NsiI — MBP — HpaI — MBP — MBP — EcoRV — SalI — NsiI — MBP — HpaI — MBP — EcoRV — NcoI — HindIII — (S)

FIGURE 2 B

TRX (~300bp) : SalI — EcoRI — TRX — HindIII — NheI

GST (~645bp) : XhoI — GST — NsiI — NcoI — HpaI — EcoRV — SalI — EcoRI —(S)— NheI

MBP1 (~1078bp) : SalI — NsiI — MBP1 — HpaI

MBP2 (~1079bp) : HpaI — MBP2 — EcoRV — NcoI — HindIII —(S)— EcoRV — SalI — PstI

MBP (~2157bp) : SalI — NsiI — MBP1 — HpaI — MBP2 — EcoRV — NcoI — HindIII —(S)— EcoRV — SalI — PstI FIGURE 3
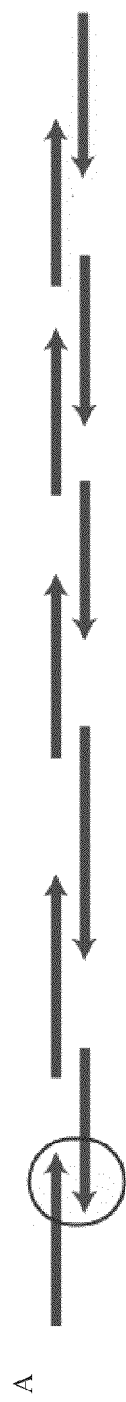
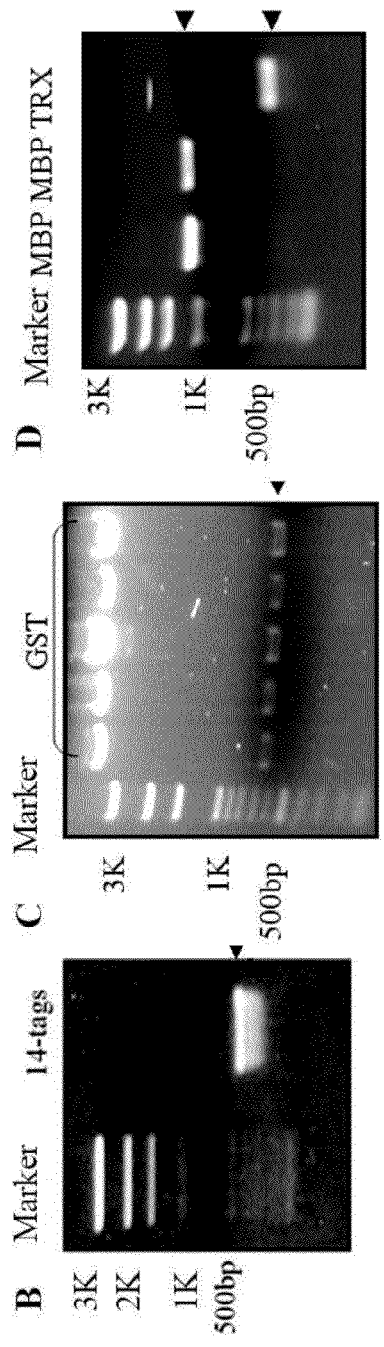

AUTO-DEVELOPING AND REGULARLY-WEIGHTED PROTEIN MOLECULAR WEIGHT MARKER KIT AND METHOD FOR PREPARING THE SAME

FIELD OF THE INVENTION

The present invention relates to a regularly-weighted protein molecular weight marker kit comprising 14-tag, which can be further used as a positive control of Western blotting.

BACKGROUND OF THE INVENTION

Protein markers play a crucial role in proteomics research with the coming of post-genome era. However, protein markers nowadays still have many restrictions and inconveniences. For example, (1) currently, the protein markers have to be copied manually from nitrocellulose paper to film instead of developing directly in the film during western blotting; (2) the common pre-stain protein markers sold on market have low-accuracy since the staining results in heterogeneity and electricity alteration; and (3) the current protein marker kits use known proteins as markers, yet their molecular weights are fixed and irregular. Therefore, there is a need for developing an auto-developing and regularly weighted protein molecular weight marker for Western blot to solve the problems encountered in proteomics research.

There are presently various types of protein markers for electrophoresis and Western blotting, and most of them are pre-stain markers. For instance, the multicolored protein marker is known for its colorful marker that enables easy observation, but the low-accuracy problem is still unsolved.

Chang et al. used a set of green fluorescent protein (GFP) fused proteins to construct dye-free protein molecular weight markers, which can emit fluorescence and present bands as regular as a ladder (Chang M., Hsu H. Y. and Lee H. J. Dye-free protein molecular weight markers. Electrophoresis, 26: 3062-68, 2005). Although the markers are convenience, they cannot be heated since GFP would be denatured and lose function. Without heating, however, the markers cannot be denatured thoroughly. Thus, the low-accuracy problem still remains.

Biotinylated protein markers are also available. These markers are dye-free but additional biotin label is required. Moreover, in order to be detected by color reaction, there is a need of labeling with HRP-conjugated anti-biotin antibody or HRP-conjugated avidin, which causes many inconveniences. In addition, biotin labeling may also alter the electric charge of protein marker and result in inaccuracy.

There are products of HIS-tag, S-tag or E-tag-fused protein markers as well. When using HIS-tag, S-tag, or E-tag antibodies to carry out development, the protein markers would auto-develop on film simultaneously. Those protein markers are not popular for the reason that the color presents simultaneously only when HIS-tag, S-tag, or E-tag antibodies is used to monitor protein expression. Otherwise, adding HRP-conjugated HIS-tag, S-tag, or E-tag antibodies is needed to activate the color reaction, which makes the procedure quite troublesome.

BRIEF DESCRIPTION OF THE DRAWINGS

The invention can be more fully understood by reading the subsequent detailed descriptions and examples with references made to the accompanying drawing, wherein:

FIGS. 2A and 2B indicate the restriction enzyme maps of the recombinant protein markers. Constructing the restriction enzyme map in advance could not only decrease burdens of gene cloning for adding molecular weight but also prevent repetition of cutting sites. The numbers on the left side represent molecular weight; (s) represents stop codon.

FIG. 3 shows (A) gene cloning design of basic recognition unit of 14-tag recombinant protein markers, GST, MBP, and TRX; and (B-C) size checking result of 14-tag, GST, MBP, and TRX by restriction enzyme digestion and agarose gel electrophoresis. (A) The schematic diagram of assembly polymerase chain reaction (PCR). 10 primers were designed, and 18 bp at 3'-end of one primer is complementary to the 5'-end of the next primer. Those primers were annealed into a linear sequence with restriction enzyme cutting sites at each end. (B) The size of assembly PCR product is confirmed about 409 bp by argarose gel electrophoresis. (C) The size of GST, after PCR amplification, insertion into pBlunt plasmid and restriction enzyme digestion, is confirmed about 645 bp. (D) The size of MBP and TRX, after PCR amplification, insertion into pBlunt plasmid and restriction enzyme digestion, are confirmed about 1134 bp and 300 bp respectively. M indicates protein molecular weight marker.

SUMMARY OF THE INVENTION

Figure 1:
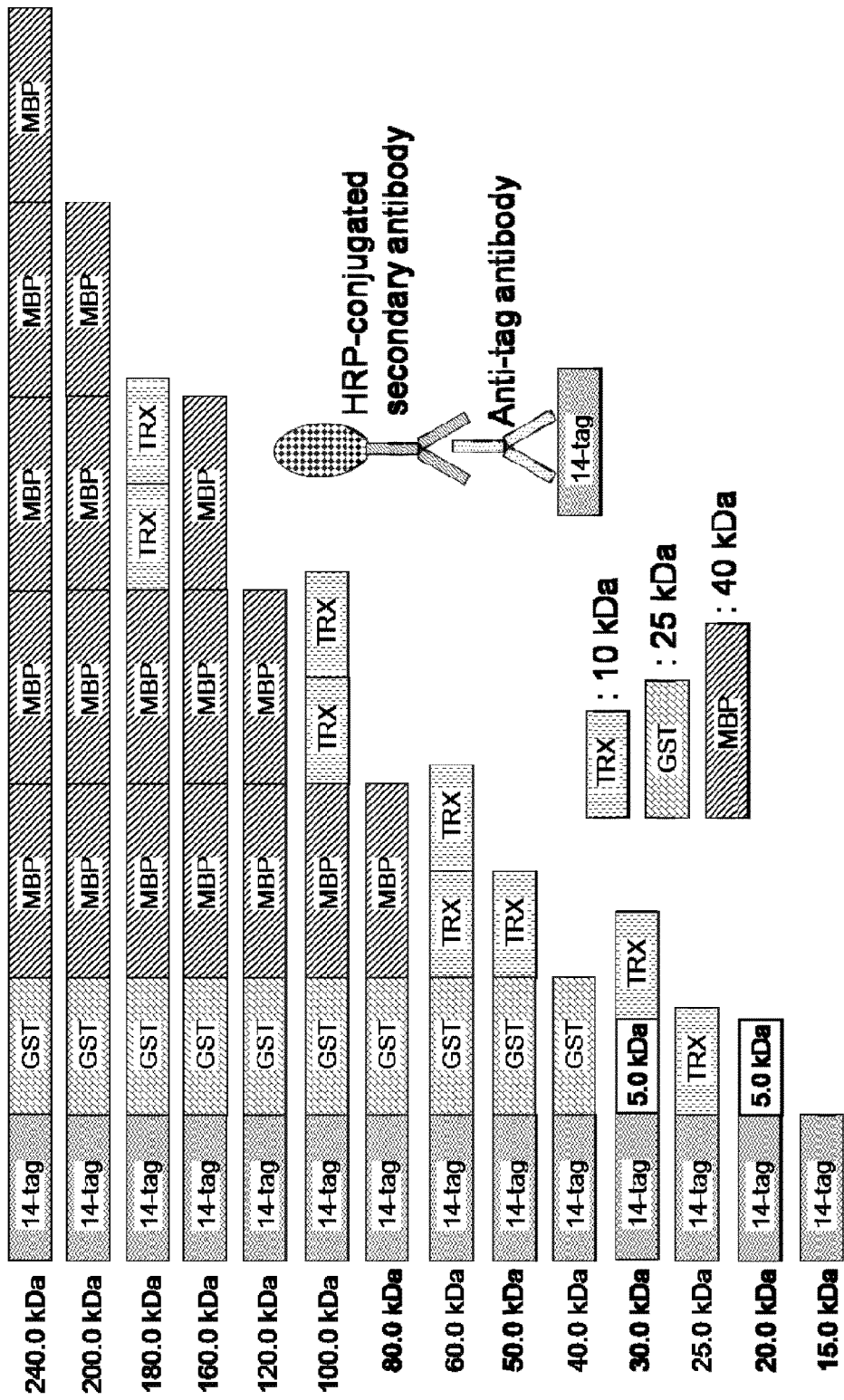
FIG. 1 shows the schematic representation of the 14-tag protein marker of the present invention, which is auto-developed and regular molecular weight. The numbers on the left side of the figure represent molecular weight. In order to form the ladder-like 14-tag protein marker with regular molecular weight, the 14 tags is used as basic recognition unit and connected with GST (glutathione-S-transferase), MBP (maltose-binding protein), TRX (thioredoxin) and/or 5.0 kDa artificial peptides. When detecting target protein with anti-tag antibodies, the protein marker of present invention is recognized at the same time and developed on film.

The present invention provides an auto-developing and regularly-weighted protein molecular weight marker kit, which comprises: (a) a plurality of recombinant proteins having formula (I), $$(B)_m\text{-}A\text{-}(C)_n \quad (I),$$

wherein A is a polypeptide of SEQ ID NO: 1, B and C are independently any mutually identical or different polypeptides with molecular weight being about a multiple of 5, and m and n is independently 0 or any integer larger than 0; and (b) one or more solvents for stabilizing the recombinant proteins. The present invention also provides a method for preparing the auto-developing protein marker kit with regular molecular weight comprising: (a) constructing a plurality of nucleotide sequences encoding recombinant protein having formula (I) into DNA plasmids independently, and obtain a recombinant protein expressing vector, $$(B)_m\text{-}A\text{-}(C)_n \quad (I),$$

wherein A is a polypeptide of SEQ ID NO: 1, B and C are independently any mutually identical or different polypeptides with molecular weight being about a multiple of 5, and m and n is independently 0 or any integer larger than 0; (b) transforming the recombinant protein expressing vector into competent cells; (c) selecting the competent cells carried the recombinant protein expressing vector; (d) administering the competent cell carried the recombinant protein expressing vector with inducer to induce expression of recombinant proteins; and (e) extracting recombinant proteins with different molecular weights independently, and mixing the plurality of recombinant proteins with one or more solvents for stabilizing recombinant proteins.

DETAILED DESCRIPTION OF THE INVENTION

As used herein, the term "a plurality of" is employed to describe the number of elements and components of the present invention. This description should be read to more than one unless it is obvious that it is meant otherwise.

As used herein, the term "a" or "an" is employed to describe elements and components of the invention. This is done merely for convenience and to give a general sense of the invention. This description should be read to include one or at least one and the singular also includes the plural unless it is obvious that it is meant otherwise.

As used herein, the term "or" is employed to describe "and/or".

The unit of molecular weight of polypeptide is kDa or kDa in the present invention.

In order to improve the flaws of above-mentioned well known technology, the present invention provides an auto-developing and regularly-weighted protein molecular weight marker kit, which comprises: (a) a plurality of recombinant proteins having formula (I), $$(B)_m\text{-}A\text{-}(C)_n \quad (I),$$

wherein A is a polypeptide of SEQ ID NO: 1, B and C are independently any mutually identical or different polypeptides with the value of molecular weight being a multiple of 5, and m and n is independently 0 or any integer larger than 0; and (b) one or more solvents for stabilizing the recombinant proteins.

In which, the A of formula (I) is selected from one or more amino acid sequences of commercial tags and arranged properly. In some embodiments, the A is selected from the group consisting of His6-tag, HA-tag, T7-tag, E-tag, VSV-g-tag, V5-tag, AU5-tag, S-tag, HSV-tag, FLAG-tag, Lumio-tag, Glu-Glu-tag, cMyc-tag, and AU1-tag. The amino acid sequences and encoding DNA sequences thereof are shown in Table 1.

TABLE 1

The amino acid sequences of 14 tags and the encoding DNA sequences thereof

| Tag | Amino acid sequence | DNA sequence |
|---|---|---|
| His6 | SEQ ID NO: 19<br>HHHHHH | SEQ ID NO: 20<br>CATCATCATCATCATCAT |
| cMyc | SEQ ID NO: 21<br>EQKLISEEDL | SEQ ID NO: 22<br>GAACAAAAACTCATCTCAGAAGAGGATCTG |
| HA | SEQ ID NO: 23<br>YPYDVPDYA | SEQ ID NO: 24<br>TATCCATATGATGTTCCAGATTATGCT |
| S | SEQ ID NO: 25<br>KETAAAKFERQHMDS | SEQ ID NO: 26<br>AAAGAAACCGCTGCTGCTAAATTCGAACGC<br>CAGCACATGGACAGC |
| FLAG | SEQ ID NO: 27<br>DYKDADDDK | SEQ ID NO: 28<br>GATTACAAGGATGACGACGATAAG |

TABLE 1-continued

The amino acid sequences of 14 tags and the encoding DNA sequences thereof

| Tag | Amino acid sequence | DNA sequence |
|---|---|---|
| V5 | SEQ ID NO: 29<br>GKPIPNPLLGLDST | SEQ ID NO: 30<br>GGTAAGCCTATCCCTAACCCTCTCCTCGGTC<br>TCGATTCTACG |
| T7 | SEQ ID NO: 31<br>MASMTGGQQMG | SEQ ID NO: 68<br>ATGGCTAGCATGACTGGTGGACAGCAAATG<br>GGT |
| E | SEQ ID NO: 32<br>GAPVPYPDPLEPR | SEQ ID NO: 33<br>GGTGCGCCGGTGCCGTATCCGGATCCGCTGG<br>AACCGCGT |
| VSV-g | SEQ ID NO: 34<br>YTDIEMNRLGK | SEQ ID NO: 35<br>TACACCGACATCGAGATGAACCGGTTGGGC<br>AAG |
| HSV | SEQ ID NO: 36<br>SQPELAPEDPED | SEQ ID NO: 37<br>AGCCAGCCAGAACTCGCTCCTGAAGACCCA<br>GAGGAT |
| Lumio | SEQ ID NO: 38<br>CCPGCC | SEQ ID NO: 39<br>TGTTGTCCTGGCTGTTGC |
| Glu-Glu | SEQ ID NO: 40<br>CEEEEYMPME | SEQ ID NO: 41<br>TGTGAAGAAGAAGAATACATGCCGATGGAA |
| AU1 | SEQ ID NO: 42<br>DTYRYI | SEQ ID NO: 43<br>GACACCTACCGTTACATC |
| AU5 | SEQ ID NO: 44<br>TDFYLK | SEQ ID NO: 45<br>ACCGACTTCTACCTGAAG |

In some embodiments, under the premise without decreasing the developing effect of Western blotting, the arrangement and construction strategy of tags assembling A can be adjusted. Such adjustments include but are not limited to:
(1) in order to achieve the goal of assembling regularly-weighted protein molecular weight marker, such as forming the ladder-like protein molecular weight marker, a tag is allowed to share one or more amino acids to the next tag to adjust the molecular weight;
(2) in order to prevent particular restriction enzyme digestion in the sequences or to meet codon usage bias of cells expressing the recombinant proteins, one or more bases of each tag-encoding DNA shown in Table 1 can be replaced in favor of construction and expression of recombinant proteins, which assemble the regularly-weighted protein molecular weight markers;
(3) in order to add shorter artificial peptide sequences and adjust the molecular weight of A in formula (I), or to add new restriction enzyme cutting sites, one or more bases of each tag-encoding DNA shown in Table 1 can be added and/or, eliminated in favor of construction and expression of recombinant proteins, which assemble the regularly-weighted protein molecular weight markers;
(4) in order to enhance the recognition sensitivity of anti-tag antibodies, base(s) of each tag-encoding DNA shown in Table 1 can be added and/or eliminated to create amino acid(s) helpful to recognition sensitivity of the anti-tag antibodies.

In a particular embodiment, the arrangement of tags assembling A is His-HA-T7-E-VSVg-V5-AU5-S-HSV-FLAG-Lumio-Glu-Glu-cMyc-AU1 and the molecular weight thereof is about 15.0 kDa.

In a preferred embodiment, the A of formula (I) is the polypeptide of SEQ ID NO: 1 and the molecular weight thereof is about 15.0 kDa.

B and C of formula (I) are independently any mutually identical or different polypeptides with the value of molecular weight being a multiple of 5, and m and n are independently 0 or any integer larger than 0. In some embodiments, B and C are electric neutral, hydrophilic and/or polypeptides relatively insusceptible to glycosylation to prevent inaccuracy problem of the present recombinant protein as protein molecular weight marker.

In a preferred embodiment, the peptide sequences of B and C are selected from the group consisting of amino acid sequence of thioredoxin comprising one or a plurality of SEQ ID NO: 2, amino acid sequence of glutathione-S-transferase comprising one or a plurality of SEQ ID NO: 3, amino acid sequence of maltose-binding protein comprising one or a plurality of SEQ ID NO: 4, and amino acid sequence comprising one or a plurality of SEQ ID NO: 5. Among these sequences, the arrangement of the amino acid sequence of thioredoxin comprising one or a plurality of SEQ ID NO: 2, the amino acid sequence of glutathione-S-transferase comprising one or a plurality of SEQ ID NO: 3, the amino acid sequence of maltose-binding protein comprising one or a plurality of SEQ ID NO: 4, and the artificial amino acid sequence comprising one or a plurality of SEQ ID NO: 5 is any possible permutation and combination. The flanking region of selected amino acid sequences mentioned previously may include the residual amino acid sequence resulted from recombinant protein construction. Those residual fragments may derive from partial commercially available vector sequences or restriction enzyme recognition sequences, designed for simplifying the recombinant protein construction.

For $(B)_m$-A-$(C)_n$ of the present invention, the flanking region of $(B)_m$, A, and $(C)_n$ may include the residual amino acid sequence resulted from recombinant protein construction. Those residual fragments may derive from partial commercially available vector sequences or restriction enzyme recognition sequences, designed for simplifying the recombinant protein construction.

For the recombinant protein of formula (I), if m=0 and n=0, it is indicated that the recombinant protein consists of polypeptide A; if m=0 and n>0, it is indicated that the N terminal of the recombinant protein is polypeptide A; if m>0 and n=0, it is indicated that the C terminal of recombinant protein is polypeptide A; if m>0 and n>0, it is indicated that there are other amino acid sequences at the two ends of polypeptide A. In a preferred embodiment, m is 0 and n is 0 or larger than 0, such as various recombinant proteins shown in FIG. 1. The 15.0 kDa recombinant protein is a polypeptide of m=0, n=0, and A is SEQ ID NO: 1; the 20.0 kDa recombinant protein is the polypeptide of m=0, n=1, A is SEQ ID NO: 1, and C is an artificial amino acid sequence of SEQ ID NO: 5.

The auto-developing and regularly-weighted protein molecular weight marker kit of the present invention further comprises a solvent for stabilizing recombinant proteins. The solvent for stabilizing recombinant proteins extends the shelf-life of the recombinant protein and prevents the protease degradation. The solvent includes but not limits to Tris-$H_3PO_4$, ethylene diamine tetraacetic acid (EDTA), sodium dodecyl sulfate (SDS), dithiothreitol (DTT), $NaN_3$ and/or glycerol with proper concentration and/or pH value.

According to the requirement, a plurality of recombinant proteins having formula (I) is selected for the protein molecular weight marker kit of the present invention. In some embodiments, the plurality of recombinant proteins having formula (I) are selected from the group consisting of a polypeptide of SEQ ID NO: 1 (M.W. is about 15.0 kDa), a polypeptide of SEQ ID NO: 6 (M.W. is about 20.0 kDa), a polypeptide of SEQ ID NO: 7 (M.W. is about 25.0 kDa), a polypeptide of SEQ ID NO: 8 (M.W. is about 30.0 kDa), a polypeptide of SEQ ID NO: 9 (M.W. is about 40.0 kDa), a polypeptide of SEQ ID NO: 10 (M.W. is about 50.0 kDa), a polypeptide of SEQ ID NO: 11 (M.W. is about 60.0 kDa), a polypeptide of SEQ ID NO: 12 (M.W. is about 80.0 kDa), a polypeptide of SEQ ID NO: 13 (M.W. is about 100.0 kDa), a polypeptide of SEQ ID NO: 14 (M.W. is about 120.0 kDa), a polypeptide of SEQ ID NO: 15 (M.W. is about 160.0 kDa), a polypeptide of SEQ ID NO: 16 (M.W. is about 180.0 kDa), a polypeptide of SEQ ID NO: 17 (M.W. is about 200.0 kDa), and a polypeptide of SEQ ID NO: 18 (M.W. is about 240.0 kDa), which are shown in FIG. 1.

For example, if there is a need for preparing protein molecular weight marker kit suitable for low molecular weight, SEQ ID NO. 1 (MW 15.0 kDa), SEQ ID NO. 6 (MW 20.0 kDa), SEQ ID NO. 7 (MW 25.0 kDa), SEQ ID NO. 8 (MW 30.0 kDa), SEQ ID NO. 9 (MW 40.0 kDa), SEQ ID NO. 10 (MW 50.0 kDa), SEQ ID NO. 11 (MW 60.0 kDa), SEQ ID NO. 12 (MW 80.0 kDa), SEQ ID NO. 13 (MW 100.0 kDa), and SEQ ID NO. 14 (MW 120.0 kDa) are selected to obtain the protein molecular weight marker kit used for low molecular weight.

Based on the well-known protein electrophoresis technology, the auto-developing and regularly-weighted protein molecular weight marker kit is used as protein marker for SDS-PAGE. For each and every recombinant protein of the present protein molecular weight marker kit contains the amino acid sequences of one or more commercial tags, users applying the present protein molecular weight marker kit in Western blotting do not need to buy new antibodies if the target protein contains the same protein marker(s). It is because that all the recombinant proteins has the amino acid sequence of SEQ ID NO: 1 that can be recognized by antibody selected from the group consisting of anti-His6-tag antibody, anti-HA-tag antibody, anti-T7-tag antibody, anti-E-tag antibody, anti-VSV-g-tag antibody, anti-V5-tag antibody, anti-AU5-tag antibody, anti-5-tag antibody, anti-HSV-tag antibody, anti-FLAG-tag antibody, anti-Lumio-tag antibody, anti-Glu-Glu-tag antibody, anti-cMyc-tag antibody, and anti-AU1-tag antibody. At the same time, the present protein molecular weight marker kit is also useful as positive control.

The present invention also provides a method for preparing the auto-developing and regularly-weighted protein molecular weight marker kit comprising (a) constructing vectors, which comprise a plurality of nucleotide sequences encoding recombinant proteins of formula (I) independently, to obtain recombinant protein expression vectors, $$(B)_m\text{-}A\text{-}(C)_n \qquad (I),$$

wherein A is a polypeptide of SEQ ID NO: 1, B and C are independently any mutually identical or different polypeptides with the value of molecular weight being a multiple of 5, and m and n is independently 0 or any integer larger than 0;

(b) transforming the recombinant protein expression vectors into competent cells;

(c) selecting the competent cells carrying the recombinant protein expression vectors;

(d) inducing the competent cells carrying the recombinant protein expression vectors to express the recombinant proteins by administrating a inducer, such as IPTG; and (e) extracting each of recombinant protein with different molecular weights independently, and mixing a plurality of recombinant proteins with one or more recombinant protein stabilizing solvents.

For increasing protein purity, protein purification is further performed by using various well-known protein purification technologies, such as affinity column and S200 gel filtration, before above-mentioned step (e).

In some embodiments, the above-mentioned plurality of nucleotide sequences encoding recombinant protein of formula (I) are selected from the group consisting of a nucleotide sequence encoding the polypeptide of SEQ ID NO: 1, a nucleotide sequence encoding the polypeptide of SEQ ID NO: 6, a nucleotide sequence encoding the polypeptide of SEQ ID NO: 7, a nucleotide sequence encoding the polypeptide of SEQ ID NO: 8, a nucleotide sequence encoding the polypeptide of SEQ ID NO: 9, a nucleotide sequence encoding the polypeptide of SEQ ID NO: 10, a nucleotide sequence encoding the polypeptide of SEQ ID NO: 11, a nucleotide sequence encoding the polypeptide of SEQ ID NO: 12, a nucleotide sequence encoding the polypeptide of SEQ ID NO: 13, a nucleotide sequence encoding the polypeptide of SEQ ID NO: 14, a nucleotide sequence encoding the polypeptide of SEQ ID NO: 15, a nucleotide sequence encoding the polypeptide of SEQ ID NO: 16, a nucleotide sequence encoding the polypeptide of SEQ ID NO: 17, and a nucleotide sequence encoding the polypeptide of SEQ ID NO: 18.

The next examples provide some exemplary embodiments of the present invention as follows:

EXAMPLES

The examples below are non-limiting and are merely representative of various aspects and features of the present invention.

Example 1

FIG. 1 is a schematic diagram of protein markers containing 14 tags at N-terminal and having different molecular size. 14 tags of most common-used in current proteomic studies (shown in Table 1) were selected and used as "locomotive" of the present protein marker. Other proteins were sequentially connected to the 14 tags to form ladder-like protein markers with regular molecular weights. During color development operating procedure of Western blotting, if antibodies recognizing any one of the 14 tags were used, and the HRP-conjugated secondary antibodies were then employed to recognize the anti-tag antibodies, ladder-like protein markers with regular molecular weight can be auto-developed on the film; convenience and accuracy of protein-related studies were therefore increased. 14-tag was used as a beginning in this example, and proteins with different molecular weights, TRX (thioredoxin, molecular weight is about 10.0 kDa), GST (glutathione-S-transferase, molecular weight is about 25.0 kDa), or MBP (maltose-binding protein, molecular weight is about 40.0 kDa), were connected sequentially to construct protein marker with specific size.

Example 2

Construction of Genes Encoding 14-Tag, GST, MBP, TRX

The required primers listed in Table 2 were ordered.

TABLE 2 primers used for annealing 14-tag by assembly-PCR

| Primer No. | Length (Repeating Sequence Length) | Sequence 5' → 3' |
|---|---|---|
| P1 | 57 | SEQ ID NO: 46<br>GGAACGCCATATGCACCATCATCATCATCATTATCCTTACGATGTTCCAGATTATGC |
| P1new | 40 | SEQ ID NO: 47<br>GGAATTCCATATGCGGGGTTCTCATCATCATCATCATCAT |
| P2-A | 57 (18) | SEQ ID NO: 48<br>CCACCAGTCATACTGGCCATGATGTAACGGTAGGTGTCAGCATAATCTGGAACATCG |
| P3 | 57 (18) | SEQ ID NO: 49<br>GGCCAGTATGACTGGTGGACAGCAAATGGGTGCGCCGGTGCCGTATCCGGACCCACT |
| P4-A | 57 (18) | SEQ ID NO: 50<br>CCCAACCGGTTCATCTCGATGTCGGTGTAACGCGGTTCCAGTGGGTCCGGATACGGC |
| P5 | 57 (18) | SEQ ID NO: 51<br>CGAGATGAACCGGTTGGGCAAGCCTATCCCTAACCCTCTCCTCGGTCTCGATTCTAC |
| P6-A | 57 (18) | SEQ ID NO: 52<br>TCAAATTTAGCAGCAGCGGTTTCCTTCAGGTAGAAGTCCGTAGAATCGAGACCGAGG |
| P7 | 57 (18) | SEQ ID NO: 53<br>CGCTGCTGCTAAATTTGAGCGCCAGCACATGGACAGCCAGCCAGAACTCGCTCCTGA |
| P8-A | 57 (18) | SEQ ID NO: 54<br>CAACACTTATCGTCGTCATCCTTGTAATCCTCTGGGTCTTCAGGAGCGAGTTCTGGC |
| P9 | 57 (18) | SEQ ID NO: 55<br>TGACGACGATAAGTGTTGTCCTGGCTGTTGCGAAGAAGAAGAATACATGCCGATGGA |
| P10-A | 58 (18) | SEQ ID NO: 56<br>CTAGCTAGCTCACAGATCCTCTTCTGAGATGAGTTTTTGTTCCATCGGCATGTATTCTTCAGAAGAGGATCTGCTCGAGGGTGATGTTAAACTTACCCAATCGTACGCTAGCTAG<br>Reverse primer (SEQ ID NO: 57):<br>AGAATACATGCCGATGGAACAAAAACTCATCTCAGAAGAGGATCTGTGAGCTAGCTAG |

TABLE 2-continued

Primers used for annealing 14-tag by assembly-PCR

| Primer No. | Length (Repeating Sequence Length) | Sequence 5' → 3' |
|---|---|---|
| P11-A | 57 (15) | SEQ ID NO: 58<br>CTAGCTAGCGTACGATTGGGTAAGTTTAACATCACCCTCGAGCAGATCCTCTTCTGA<br>Reverse primer (SEQ ID NO: 59):<br>TCAGAAGAGGATCTGCTCGAGGGTGATGTTAAACTTACCCAATCGTACGCTAGCTAG |

The sequences of the initial and the end primers (P1 and P10-A) contained the designed restriction enzyme cutting sites. Assembly-PCR was utilized to anneal these primers into one fragment, and the fragment was inserted to pBlunt vector (Invitrogen). The obtained recombinant plasmid was named pBlunt-15 kDa. To conduct PCR, P1new and P10-A were then used as primers and pBlunt-15 kDa was used as template, and the PCR fragments were ligated to pBlunt vector to obtain pBlunt-RGS-15 kDa plasmid. Subsequently, P1new and P11-A (without stop codon) were used as primers and pBlunt-15 kDa was used as template for conducting PCR, and the PCR fragments were ligated to pBlunt vector. The obtained product was named pBlunt-20 kDa plasmid.

In addition, the primers that were designed to contain special cutting sites were as Table 3.

PCR technique was utilized to insert gene fragments, such as GST, MBP, and TRX, into pBlunt vectors (pBlunt-GST'pBlunt-MBP'pBlunt-TRX). The plasmids were transformed into TOP10 *E. coli* to select a colony. Plasmid DNA was extracted from selected colony and cut by restriction enzyme to confirm the size of sequence. The colony containing fragment of correct size was subjected to further sequencing analysis.

1. Assembly-Polymerase Chain Reaction

PCR Reaction Solution:

| | |
|---|---|
| 10× PCR buffer (Taq DNA polymerase buffer) | 5 μl |
| 2.5 mM dNTP | 5 μl |
| primer mixture | 1 μl |
| ddH$_2$O | 37.3 μl |

TABLE 3

Primers for PCR cloning of TRX, MBP and GST

| Primer No. | Length (Repeating Sequence Length) | Sequence 5' → 3' |
|---|---|---|
| GST-P1 | 24 (18) | SEQ ID NO: 60<br>CTCGAGATGTCCCCTATACTAGGT |
| GST-P2-A | 59 (14) | SEQ ID NO: 61<br>GCTAGCTCAGAATTCGTCGACGATATCGTTAACCCATGGATGCATATACTTGCTGGATT |
| MBP1-P1 | 58 (18) | SEQ ID NO: 62<br>GTCGACATGCATAAAATCGAAGAAGGTAAACTGGTAATCTGGATTAACGGCGATAAAG |
| MBP1-P2-A | 58 (18) | SEQ ID NO: 63<br>GTTAACGGCTTCATCGACAGTCTGACGACCGCTGGCGGCGTTGATCACCGCAGTACGC |
| MBP2-P1 | 58 (18) | SEQ ID NO: 64<br>GTTAACAAAATCGAAGAAGGTAAACTGGTAATCTGGATTAACGGCGATAAAGGCTAT |
| MBP2-P2-A | 58 (18) | SEQ ID NO: 65<br>CTGCAGGTCGACGATATCCTAAAGCTTCCATGGGATATCGGCTTCATCGACAGTCTGA |
| TRX-P1 | 52 (18) | SEQ ID NO: 66<br>GTCGACGAATTCAGCGATAAAATTATTCACCTGACTGACGACAGTTTTGACA |
| TRX-P2-A | 50 (18) | SEQ ID NO: 67<br>GCTAGCAAGCTTACCCACTTTGGTTGCCGCCACTTCACCGTTTTTGAACA |

-continued

| Cell cDNA | 1 μl |
|---|---|
| Taq DNA polymerase | 0.5 μl |
| Pfu DNA polymerase | 0.2 μl |
| Total Volume | 50 μl/reaction |

Reaction Cycle:

94° C. 2 min→[94° C. 30 sec→55° C. 30 sec→72° C. 1 min]×30 circles→72° C. 5 min→4° C.

2. DNA Ligation Reaction Solution

| fragment to be inserted | 7 μl |
|---|---|
| vector (100~200 ng) | 1 μl |
| 10× polymerase buffer | 1.5 μl |
| ATP (10 mM) | 1.5 μl |
| T4 DNA polymerase (U/μl) | 1.5 μl |
| ddH$_2$O | 2.5 μl |
| Total Volume | 15 μl |

Overnight reaction under 16° C. (16-24 hr)

3. Mini-Preparation of Plasmid DNA

One white colony was picked from the plate, and seeded into 3 ml LB medium (containing 1 μg/ml Ampicillin). After cultivation in incubator under 37° C. and 180 rpm for 14-16 hr, 1.5 ml of bacteria liquid was transferred to a 1.5 ml microcentrifuge tube and subjected to 6000 rpm centrifugation for 5 min under room temperature. The supernatant was removed; 150 μl of Solution I (50 mM Tris/HCl, 10 mM EDTA (pH 8.0), and 100 μg/ml ribonuclease) was added; and vortex to resuspend the pellet. 150 μl of Solution II (200 mM NaOH and 1% SDS) was added; and the tube was gently inverted for 6-8 times followed by stood still under room temperature for 3 min. 180 μl of 3M KOAc (pH 5.5) was added. After being gently inverted for 6 to 8 times (vortex was prohibited), the tube was rested under room temperature for 3 min followed by 12000 rpm centrifugation for 3 min. The supernatant (approximate 400 μl) was transferred to another new 1.5 ml microcentrifuge tube, added with equal volume of isopropanol (400 μl), and mixed thoroughly. After placing in −20° C. refrigerator, the tube was subjected to 12000 rpm centrifugation or 3 min. The supernatant was removed. 1 ml of 75% iced alcohol was added to wash the pellet, and the tube was subject to 12000 rpm centrifugation for 3 min. After removing of the supernatant, the alcohol was discarded and the pellet was air-dried in the vacuum oven. The pellet was resuspended with 20 μl ddH$_2$O (the volume of ddH$_2$O can be adjusted according to the size of pellet).

Example 3

Gene Construction of Recombinant Protein Markers (1) pRSETB-14tags (15 kDa) plasmids and pRSETB-14tags (20 kDa) plasmids were obtained by NdeI and HindIII digestion of pBlunt-15 kDa plasmid and pBlunt-20 kDa plasmid, which followed by ligation into pRSETB expression vector (Invitrogen).
(2) TRX was inserted after 20 kDa with EcoRI and HindIII to obtain pRSETB-14tags-TRX (30 kDa) plasmid.
(3) To obtain pRSETB-14tags-GST-stop-TRX (40 kDa) plasmid, an in-between sequence of 30 kDa recombinant protein was replaced with GST, which followed by a stop codon, by using XhoI and NheI.
(4) To remove the stop codon between GST and TRX and thus obtain pRSETB-14tags-GST-TRX (50 kDa) plasmid, the pRSETB-14tags-GST-stop-TRX (40 kDa) plasmid was digested by EcoRI and then self-ligated.
(5) To obtain pRSETB-14tags-TRX (25 kDa) plasmid, the in-between GST of the 50 kDa plasmid was removed by using XhoI and SalI; and the cutting sites of XhoI and SalI were ligated to each other to make the original restriction cutting site disappeared.
(6) TRX was inserted into the sequence of 40 kDa plasmid by using HpaI and NheI to replace the stop codon after GST and form a pRSETB-14tags-GST-TRX-TRX (60 kDa) plasmid.
(7) MBP, which was followed by a stop codon, was inserted into the 60 kDa plasmid by using HpaI and SalI; and a pRSETB-14tags-GST-MBP-stop-TRX-TRX (80 kDa) plasmid was thus formed.
(8) For obtaining pRSETB-14tags-GST-MBP-TRX-TRX (100 kDa) plasmid, the 80 kDa plasmid was digested by EcoRV and self-ligated to remove the stop codon between MBP and TRX.
(9) MBP-MBP was inserted into 40 kDa plasmid before the stop codon by using NsiI and HpaI; pRSETB-14tags-GST-MBP-MBP-stop-TRX (120 kDa) plasmid was then obtained.
(10) For obtaining pRSETB-14tags-GST-MBP-MBP-MBP (160 kDa) plasmid, MBP-MBP was substituted for TRX-TRX of 100 kDa plasmid by using SalI and HindIII to make the plasmid carry continuous three MBPs.
(11) For obtaining pRSETB-14tags-GST-MBP-MBP-MBP-TRX-TRX (180 kDa) plasmid, MBP-MBP was inserted into 100 kDa plasmid by using NsiI and HpaI to make the plasmid carry continuous three MBPs and two TRXs.
(12) For obtaining pRSETB-14tags-GST-MBP-MBP-MBP-MBP (200 kDa) plasmid, MBP-MBP was substituted for the stop-TRX of 120 kDa plasmid by using SalI and HindIII to make the plasmid carry continuous four MBP.
(13) For obtaining pRSETB-14tags-GST-MBP-MBP-MBP-MBP-MBP (240 kDa) plasmid, MBP-MBP was substituted for the last TRX-TRX of 180 kDa plasmid by using SalI and HindIII to make the plasmid carry continuous five MBP.

Example 4

E. coli Transformation

The competent cells strains, Top 10 and BL21 (DE3), prepared by our laboratory, were taken out from −80° C. refrigerator and unfrozen. 100 μl of culture was transferred to a 1.5 ml microcentrifuge tube, and 7.5 μl DNA annealing product or 1 μl DNA plasmid of protein marker was added into the tube and mixed with the culture thoroughly. After setting on ice for 30 min, the tube was placed in water bath to heat shock for 1 min and 30 sec under 42° C., and then it was placed on ice for 5 min. 600 μl LB (Luria-Broth) was added into the tube at a Laminar flow hood. The tube was incubated in 37° C. incubator for 45 min with vertical shake at 180-200 rpm, and then subjected to centrifugation at 5000 rpm for 5 min. About 550 μl of supernatant was discarded, and the cells were resuspended with about 150 μl of remaining medium. Finally, the bacteria solution was plated in LB plates containing Kanamycin (1 μg/ml, used to screen cells containing pBlunt-derived vectors) or Ampicillin (1 μg/ml, used to screen cells containing pRSETB-derived vectors), which were incubated in 37° C. incubator for 14 to 16 hr. Next day, a single white colony was picked from the plate and subjected to culture and amplification.

Example 5

Large Induction of Recombinant Protein Marker Expression

A successful transformed colony was picked from the plate and seeded in 3 ml Ampicillin-containing LB (1 μg/ml). After cultivating in 37° C. incubator for several hours, the culture was poured into a flask with 500 ml of Ampicillin-containing LB medium (1 μg/ml) and cultivated in 37° C. incubator until the $OD_{600}$ reached 0.2-0.3. 1M isopropyl β-D-1-thiogalactopyranoside (IPTG) was added into the culture to the final concentration of 0.5 mM. The culture was cultivated in 25° C. incubator until the $OD_{600}$ reached 0.6-0.8. The bacteria were pelleted by supercentrifugation at 6000 rpm, and the pellet was stored frozen after removing the supernatant.

Example 6

Monitoring the Expression of Recombinant Protein

1. SDS-PAGE Gels Preparation

10% or 12.5% SDS-PAGE running gel solution was prepared and pipetted into glass electrophoresis cell carefully. A small amount of distilled water was added carefully with dropper to produce a horizontal surface of the running gel during condensation. The gel was set for 30 min until solidified. In the following, 3% stacking gel was prepared. After discarding distilled water, the stacking gel was pipetted onto the running gel and comb with appropriate thickness was inserted to create wells for loading samples. The gel was set for another 30 min until the stacking gel solidified.

2. Analysis of SDS-PAGE Gel Electrophoresis

The bacteria harvested previously were resuspended with 50 μl PBS buffer (50 μl PBS buffer for per ml of bacteria solution pellet). 80 μl bacteria and 20 μl 6× reducing buffer were mixed thoroughly, heated at 95° C. for 5 min to make protein denature, and then placed on ice. 10-20 μl of sample was loaded in each well of upper-layer stacking gel. Electrophoresis in stacking gel was performed with electric current of 25 mA, and the following electrophoresis in running gel was performed under 158V. After finishing of the electrophoresis, the Western blotting was applied for analysis.

3. Western Blotting

SDS-PAGE was utilized to separate the protein. After that, SDS-PAGE was removed and rinsed in elector-transfer buffer to transfer the proteins from SDS-PAGE to nitrocellulose membrane (under voltage of 94V for about 1.5 hr). The nitrocellulose membrane was blocked with blocking buffer (PBS containing 5% fat-free milk) at 4° C. overnight and washed once by PBST (i.e. PBS+Tween surfactants) for 15 min in the next day. The needed primary antibody (one of the anti-tags-antibodies, listed in Table 4) was diluted with blocking buffer. The nitrocellulose membrane was reacted with blocking buffer-diluted antibody, accompanied constant shaking, at room temperature for 1 hr.

TABLE 4 the brand and dilution ratio of antibodies used in the Western blot

| Antibody Name | Species | Brand Name (Catalog no.) | Dilution ratio |
|---|---|---|---|
| AU1 | Goat | Bethyl(A190-124A) | 1/2000 |
| cMyc | Mouse | Self production (ascites) | 1/7500 |
| E-tag | Goat | Bethyl(A190-132A) | 1/2000 |
| Flag | Mouse | Sigma | 1/7500 |
| GluGlu | Goat | Bethyl(A190-110A) | 1/2000 |
| HA | Mouse | Covance | 1/4000 |
| His | Mouse | Serotech | 1/200 |
| HSV | Goat | Bethyl(A190-136A) | 1/2000 |
| S-tag | Goat | Bethyl(A190-134A) | 1/4000 |
| T7 | Goat | Bethyl(A190-116A) | 1/2000 |
| V5 | Mouse | Sigma(V8012) | 1/4000 |
| VSV-G | Goat | Bethyl(A190-130A) | 1/2000 |
| Anti-goat IgG-HRP | Rabbit | Jackson | 1/2000 |
| Anti-mouse IgG-Fc-HRP | Goat | Jackson | 1/2000 |

After repeating the 15 min washing step three times, the nitrocellulose membrane was reacted with HRP-conjugated antibody, which was diluted 2000 times with blocking buffer, on shaker at room temperature for 1 hr. The 15 min washing step was repeated three times. ECL reagents (Amersham) were utilized to detect conjugated antibodies. Equal volumes of reagent A and reagent B were mixed, and the nitrocellulose membrane was soaked in the mixture for 2-3 min. After that, the excess reagent was removed by towels. The nitrocellulose membrane was placed into cassette, and then an X-ray film was placed on the nitrocellulose membrane. The film was exposed for 3-60 sec and subjected to development. All the ECL procedures were operated in darkroom or detect the image by chemiluminescent detection system (Bio-rad) of Department of Biotechnology, Kaohsiung Medical University.

Results

1. Screening the Basic Recognition Unit and Increasing Molecular Weight Unit

The subject of the present invention is to develop an autodeveloping protein marker. First of all, the commonly used tags were selected and utilized as recognition unit of protein marker. By searching information about frequently used tags from current catalogs and references, the most commonly used tags and the sequences thereof were generalized (listed in previous Table 1) and used as the main framework of recombinant protein markers. These tags were all popularly used by current researchers. The protein marker would autodevelop only if researchers applied appropriate anti-tag antibodies, which dramatically increased user's convenience.

After identifying proper tags as the basic recognition unit of recombinant protein marker, other protein sequences were selected for assembling of protein markers with different molecular weights. Through a series of search, GST, MBP, and TRX were selected and used as fusing proteins that connected with the basic recognition unit. In addition to the benefit of increasing water solubility, these three proteins could be used as tags for purifying and antibody recognition. The 14-tag basic recognition unit was combined with these three proteins with various repetitions to create protein markers of different molecular weights (FIG. 1). Repetition of restriction enzyme cutting sites during assembly procedure can be prevented by designing their locations and order in advance (FIG. 2).

2. Gene Cloning of 14-Tag Basic Recognition Unit of Recombinant Protein Markers

The selected 14 sequences of commonly used tags were constructed into a recombinant 14-tag basic recognition unit, which was served as the basic component of protein markers with different molecular weights. The 10 primers containing sequences of these 14 tags were designed for assembly PCR to anneal primers into a 15 kDa fragment (FIG. 3A). Analyzing by gel electrophoresis, the size of assembly PCR product, as expected, was 409 bp (FIG. 3B). After that, the products were inserted into pBlunt vector and the insertion order was checked by NdeI and NheI. In order to further confirm, the plasmid was sequenced to check its sequence. On the other hand, P11-A primer was substituted for the tenth primer to anneal another 408 bp fragment, and a basic recognition unit (20 kDa) with different molecular weight, which could be used for assembling protein markers with different molecular weights, was thus obtained by the same method. To form two basic recognition units of 14-tag, restriction enzymes, NdeI and HindIII, were used to insert 15 kDa and 20 kDa sequence into pRSETB expression vector respectively.

3. Gene Cloning of GST, TRX and MBP

The primers comprising the designed restriction enzyme cutting sites was used to amplify the plasmids containing GST, TRX or MBP gene by polymerase chain reaction (PCR). Those amplified fragments were annealed into pBlunt vector and then cut by restriction enzymes. Gel electrophoresis was used to prove that the size of cutting fragments were as expected: MBP was 1134 bp, GST was 645 bp, and TRX was 300 bp (FIG. 3 C-D). Accuracy of the sequences was further confirmed by sequencing process. These three proteins were used as constructing material for increasing molecular weight of recombinant protein marker. The size of MBP protein was about 39.6 kDa; GST protein was about 25 kDa; and TRX protein was about 10 kDa.

4. Gene Cloning of the Recombinant Proteins Having Different Molecular Weight

Figure 4:
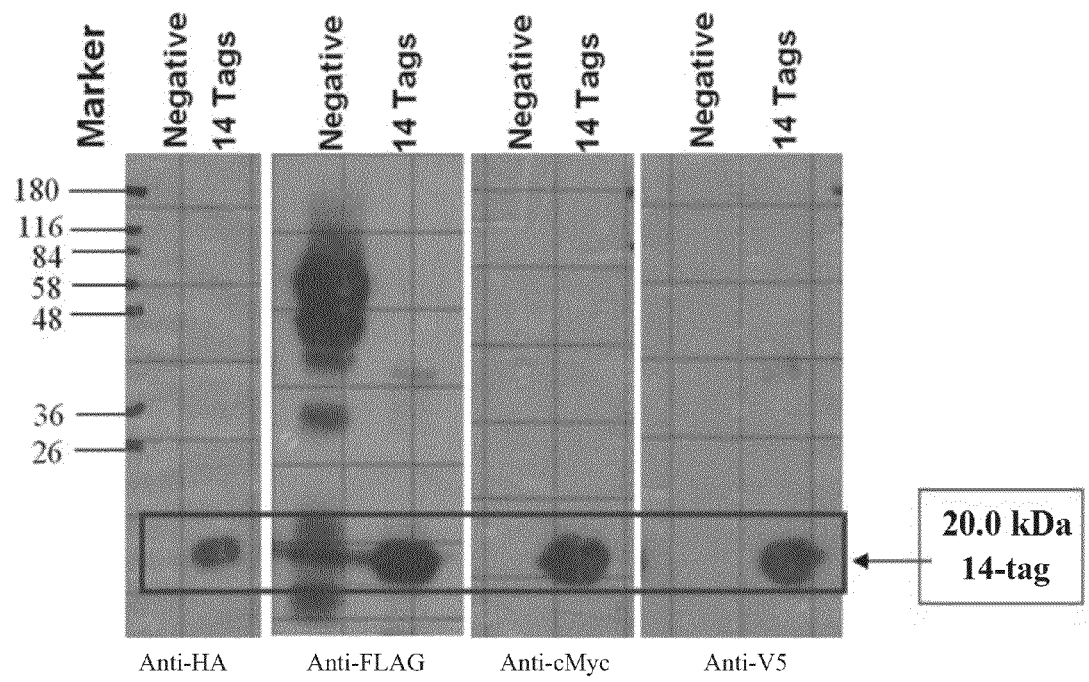
FIG. 4 shows the results that confirm 14-tag basic recognition unit expression. Western blotting is used to prove that the basic recognition unit (20 kDa) can be recognized by different antibodies and develop on film. The results confirm the feasibility of strategy of present invention since the basic recognition unit can be recognized by anti-HA antibody, anti-flag antibody, anti-cMyc antibody, anti-V5 antibody, and etc.
Figure 5:
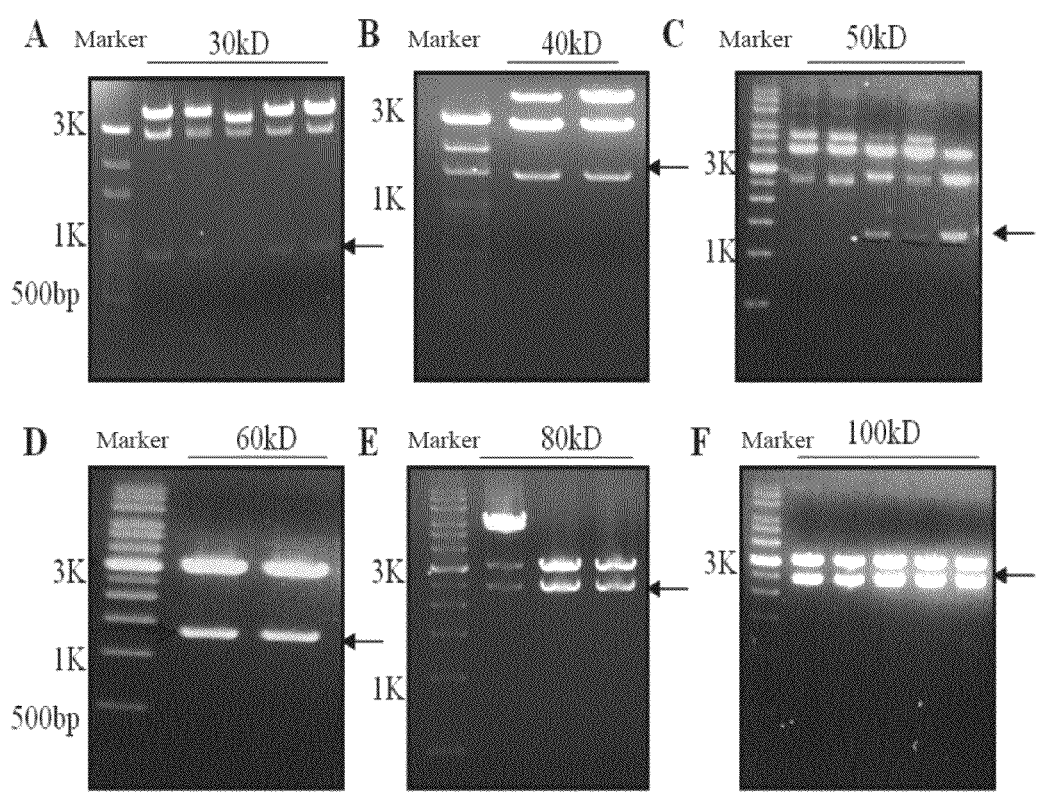
FIGS. 5A-F show the gene cloning result of 30-100 kDa protein markers. After assembling of 30-100 kDa protein markers, the size of each target fragments are confirmed 800, 1447, 1489, 1447, 2565, and 2544 bp by restriction enzymes, respectively. M indicates protein molecular weight marker.
Figure 6:
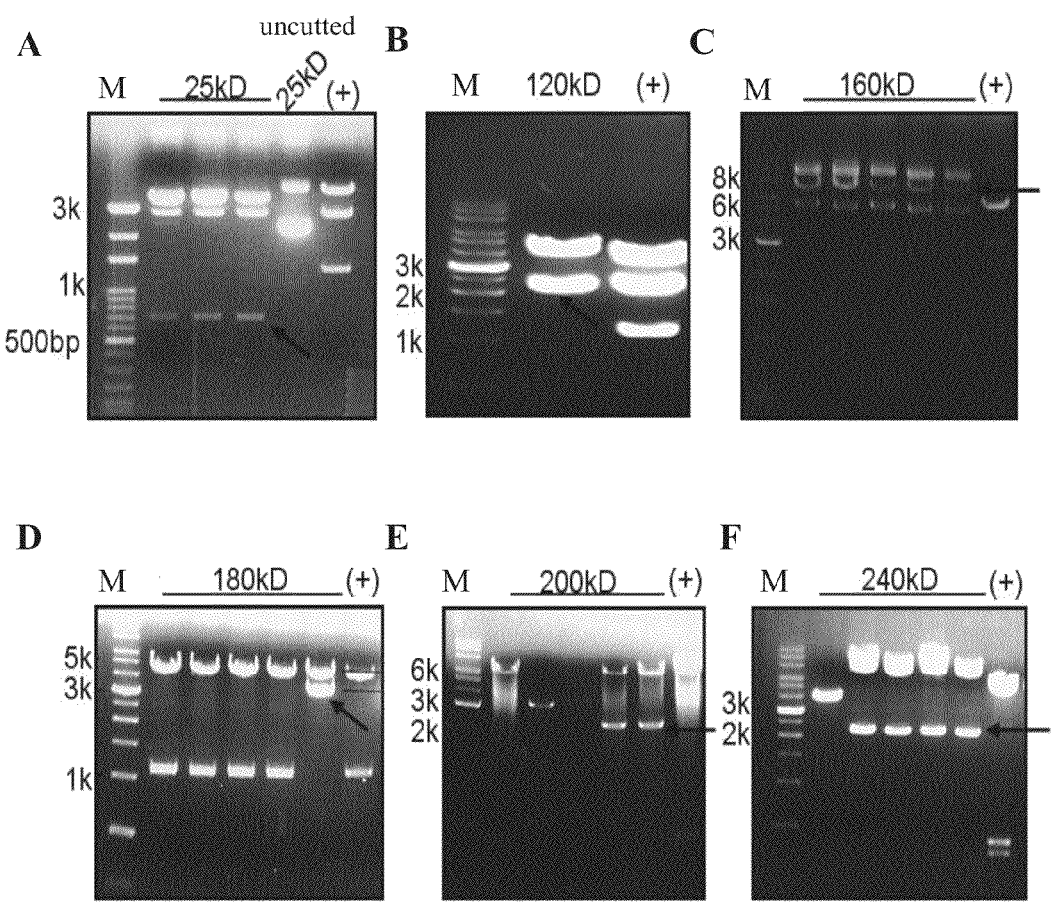
FIGS. 6A-F show the gene cloning results of 25 and 120-240 kDa protein markers. After assembling of 25 and 120-240 kDa protein markers, the size of each target fragments are confirmed 705, 2173, 7565, 3253, 2181, and 2187 bp by restriction enzymes respectively. (+) indicates positive control; and M indicates protein molecular weight marker.

When construction of the main structure of 14-tag, GST, TRX and MBP was completed, Western blotting was utilized to confirm the basic recognition unit was able to be recognized by different anti-tag antibodies (FIG. 4). The protein markers were then assembled based on the designed restriction enzyme map (FIG. 2). Since the main structure and material for construction of plasmid DNA has been sequenced, another sequencing procedure was omitted after the subcloning but restriction enzymes digestion and agarose gel electrophoresis were done to confirm that the inserted fragments were consistent with the expectation (FIG. 5 A-F and FIG. 6 A-F).

5. Ensuring the Expression of Recombinant Protein Markers

Figure 7:
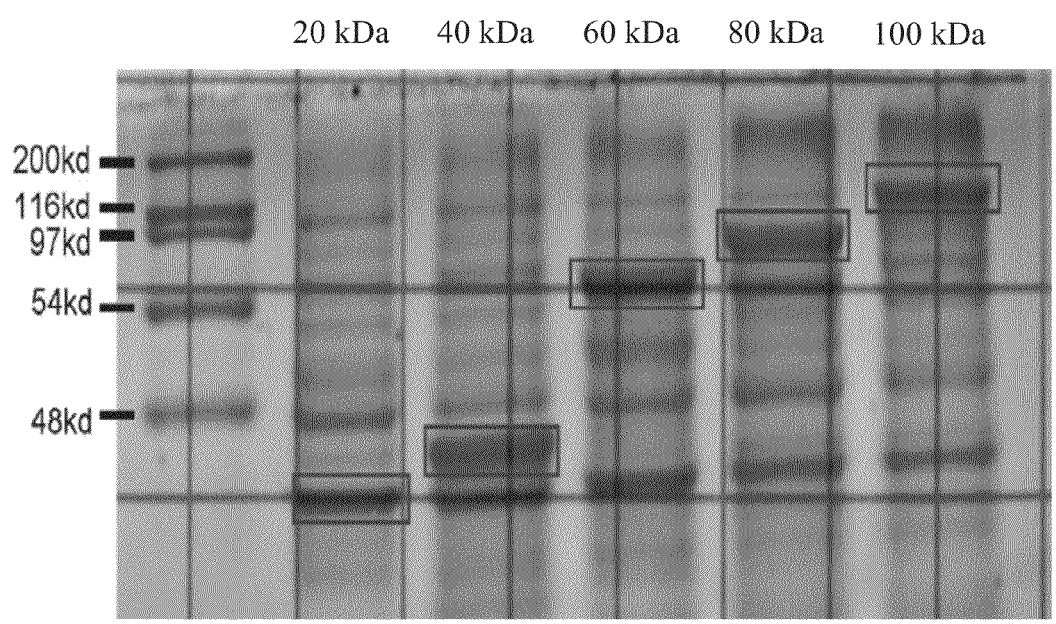
FIG. 7 shows the result of SDS-PAGE gel electrophoresis for analyzing molecular markers with different molecular weights.
Figure 8:
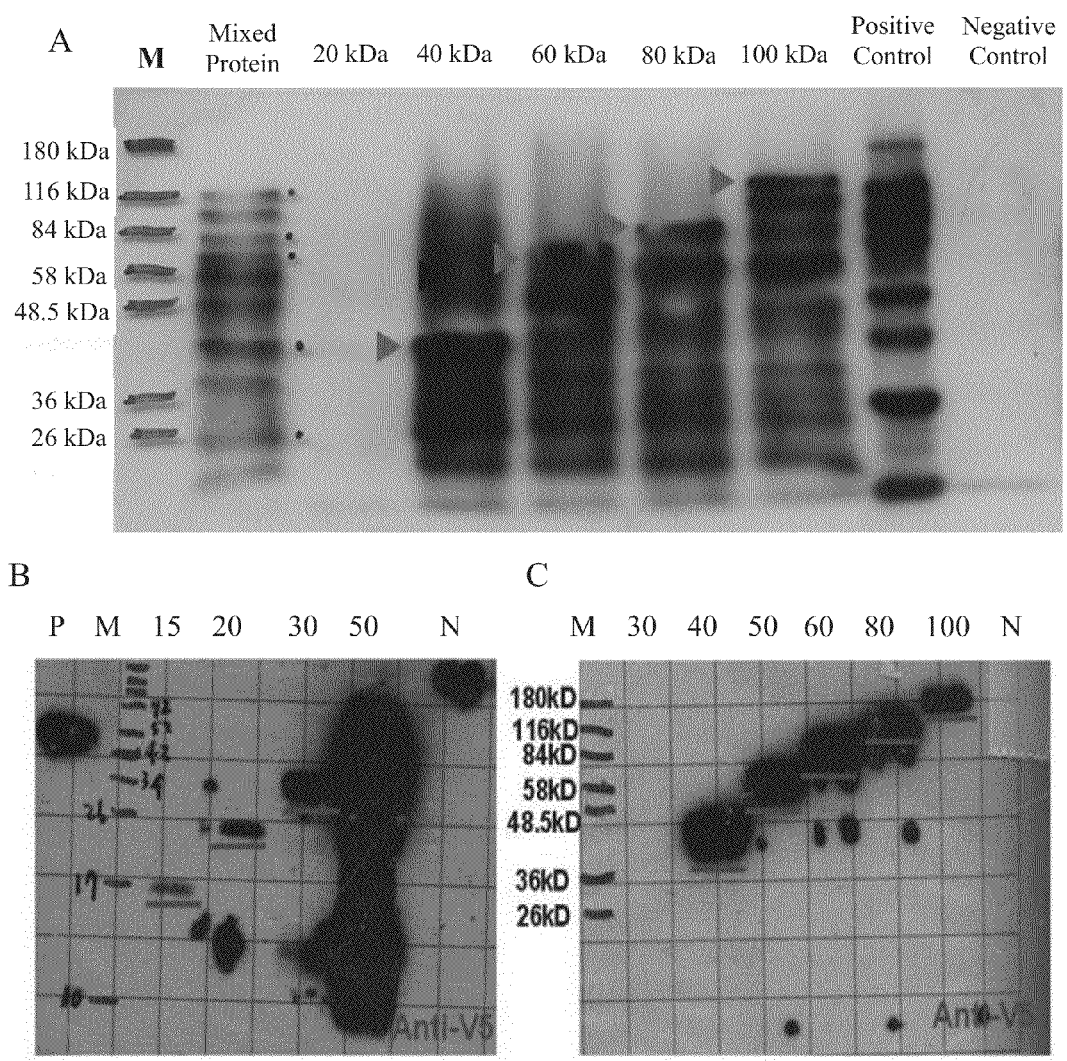
FIG. 8 shows results of (A) anti-Myc antibody or (B-C) anti-V5 antibody as primary antibody for recognizing protein markers with different molecular weights. M indicates protein marker; P indicates positive control; and N indicates negative control. The unit of protein molecular weight is kDa.

After constructing the plasmids encoding the protein markers with different molecular weights, these plasmids were transformed into BL21 (DE 3) E. coli, which was served as protein expression system. The transformed E. coli was cultured for a short time, and 0.1 mM isopropyl β-D-1-thiogalactopyranoside (IPTG) was then added to the cultures for inducing protein expression. The result of SDS-PAGE analysis (FIG. 7) confirmed that the transformed recombinant protein markers were expressed by E. coli. Various antibodies (shown in previous Table 4) were used to perform Western blotting, and the results confirmed the ability of E. coli to express recombinant protein markers with correct size, which could be recognized by various antibodies and shown as products with same molecular weight. The outcomes showed that all the protein markers having different molecular weights comprised the 14-tag basic recognition unit (FIG. 8 A-C).

Figure 9:
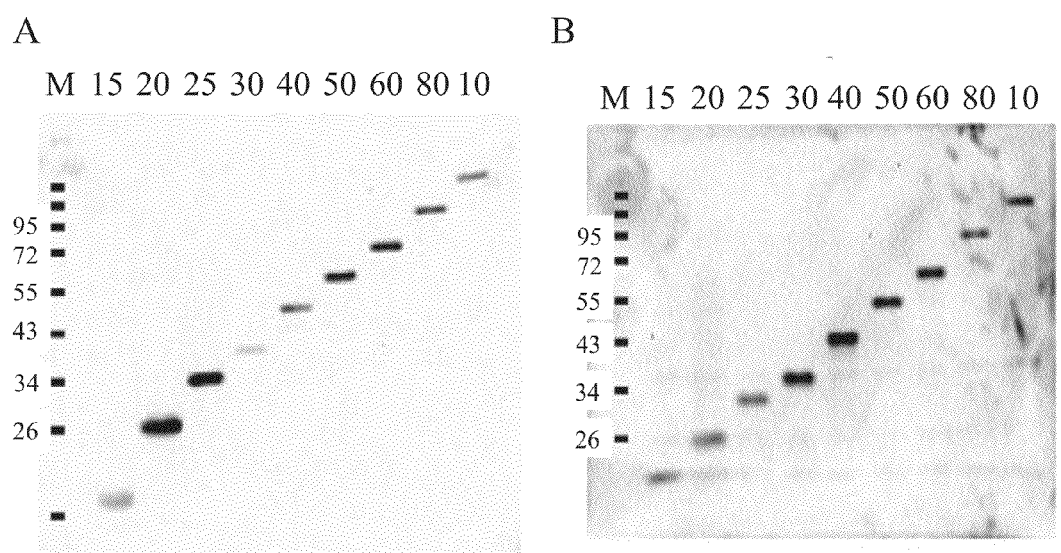
FIG. 9 shows the recognition results of protein markers with different molecular weights by (A) anti-His antibody (1:200 dilution); (B) anti-S antibody (1:4000 dilution); (C) anti-V5 antibody (1:4000 dilution); and (D) anti-Myc antibody (1:7500 dilution) after adjustment. The 15 kDa to 100 kDa recombinant protein markers can be developed clearly and obtain similar results regardless of using what kinds of antibody. Images in FIGS. 9 A, B and D are captured by chemiluminescent detection system (Bio-rad). M indicates protein marker. The unit of protein molecular weight is kDa.
Figure 9:
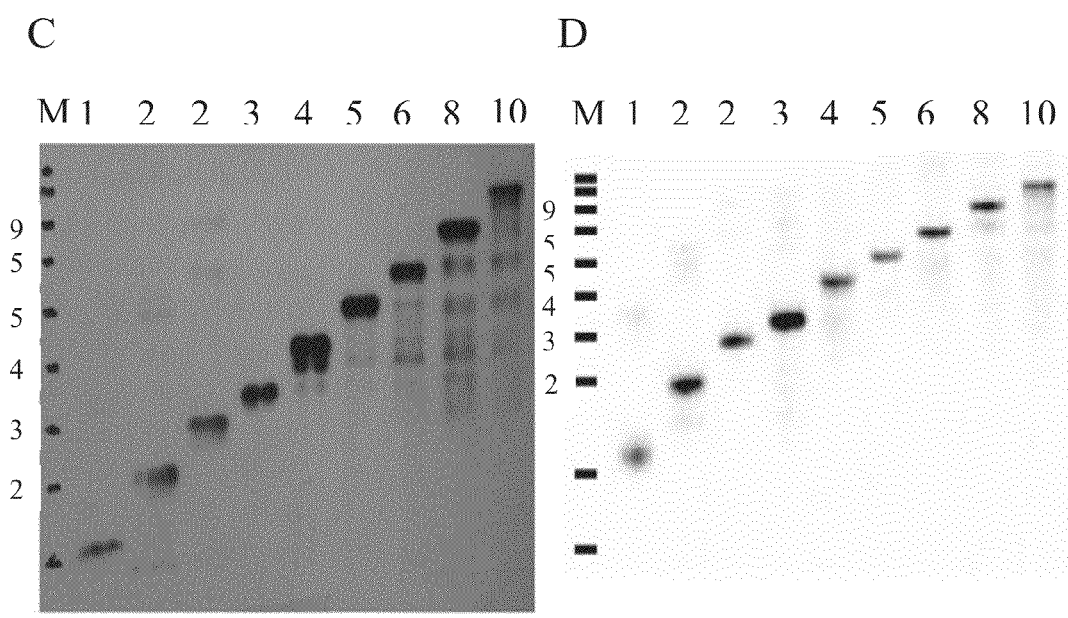
Figure 10:
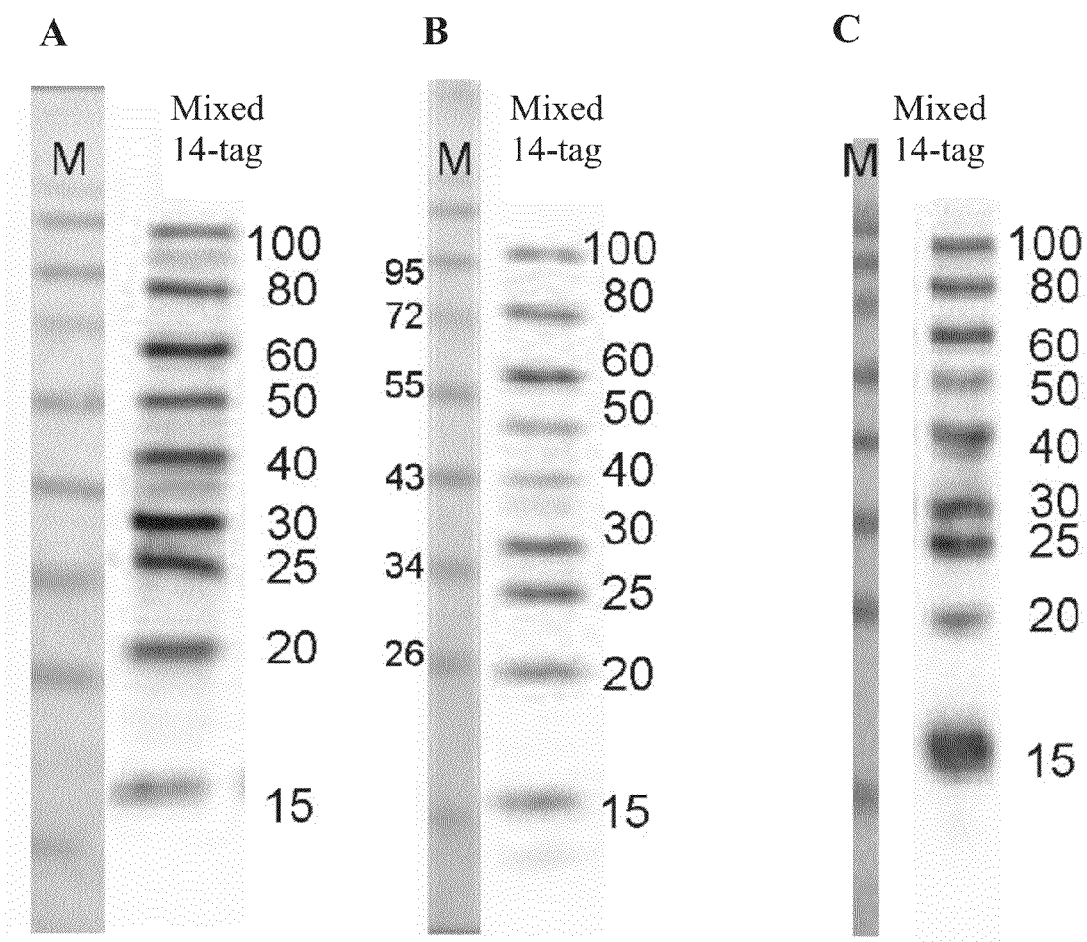
FIG. 10 shows the recognition results of protein markers with different molecular weights using (A) anti-Myc antibody (1:7500 dilution); (B) anti-HA antibody (1:4000 dilution); and (C) anti-flag antibody (1:7500 dilution) after combination and adjustment. The 15 kDa to 100 kDa recombinant protein markers can be developed clearly and obtain similar results regardless of using what kinds of antibody. Images in FIGS. 10 A to C are captured by chemiluminescent detection system (Bio-rad). M indicates protein marker. The unit of protein molecular weight is kDa.

6. Making the Combination of Recombinant Protein Markers and Analyzing its Commercialization Potential The plasmid DNAs having different molecular weights were transformed into E. coli and recombinant proteins expression thereof was induced respectively. Bacteria were subjected to centrifugation followed by formulated into sample solution with reducing dye. The protein markers with different molecular weights were mixed in different ratio. After adjusting ratio and volume for several times, the combination was completed. At last, Western blotting was used to prove that the combination of recombinant protein markers with different molecular weights was able to be recognized by various anti-tag antibodies and represented ladder-like bands clearly on the film (FIG. 9 A-D and FIG. 10 A-C). The results displayed that there were background noises between 80 kDa and 100 kDa, and also between 30 kDa and 40 kDa. The strength of background noise was altered while adding different antibodies, suggesting that the background noise may result from non-specific binding of the antibodies.

The result of Western blotting (FIG. 9 D) was further analyzed to obtain the Rf (retention factor) value. It could be found that the molecular weight of the present recombination protein markers was positively correlated to the migration distance of the proteins. The log value of molecular weight and migration distance of each recombinant protein marker of present invention was shown in Table 5.

TABLE 5

The log value of molecular weight (log M.W.) and the migration distance of each recombinant protein markers of present invention

| M.W. (kDa) | Log M.W. | Migration Distance (mm) |
|---|---|---|
| 100 | 2.00 | 4 |
| 80 | 1.90 | 6 |
| 60 | 1.78 | 8.5 |
| 50 | 1.70 | 10.5 |
| 40 | 1.60 | 13 |
| 30 | 1.48 | 16.5 |
| 25 | 1.40 | 18 |
| 20 | 1.30 | 22 |
| 15 | 1.18 | 28.5 |

Figure 11:
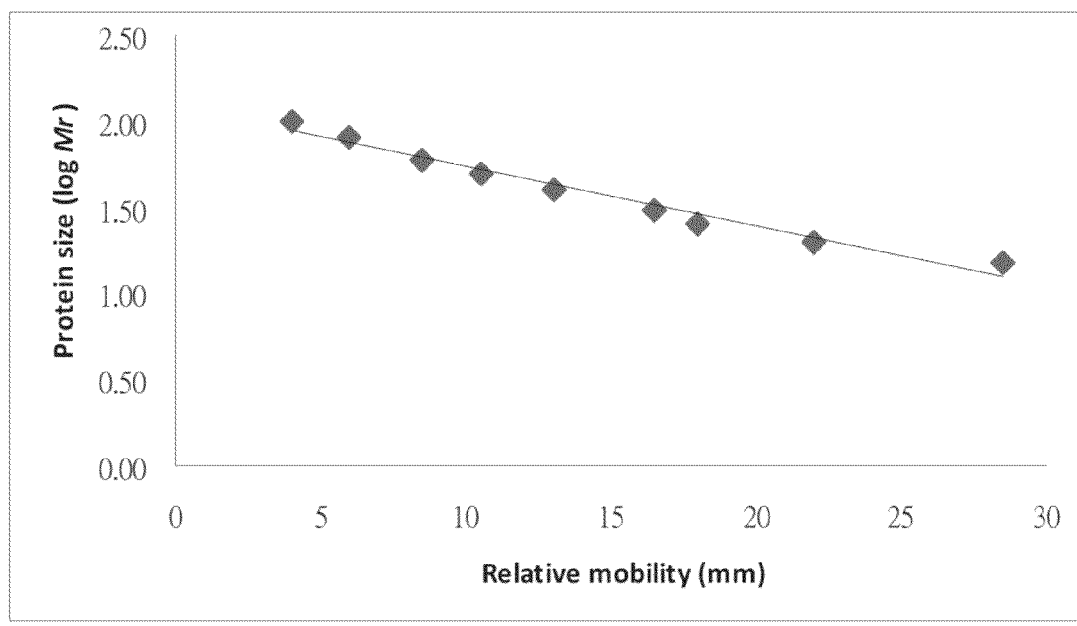
FIG. 11 shows the linear regression curves of log value of molecular weight versus relative mobility measured from FIG. 9. The vertical axis indicates log value of molecular weight of protein marker; and the horizontal axis indicates relative mobility (mm). The equation of regression line can be represented as y=−0.0345x+2.08 and the obtained $R^2$ value is 0.9821.

The linear regression of log value of molecular weight versus migration distance was performed (FIG. 11 A-B). The results demonstrated that the coefficient determination ($R^2$) of commercial protein marker (FERMANTAS) was 0.9821, whereas the $R^2$ of low range protein markers of the present invention was 0.9723 (FIG. 11 B), which is lower than that of the commercial protein marker.

One skilled in the art readily appreciates that the present invention is well adapted to carry out the objects and obtain the ends and advantages mentioned, as well as those inherent therein. The animals, processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. An auto-developing and regularly-weighted protein molecular weight marker kit, which comprises:
(a) a plurality of recombinant proteins having formula (I), $$(B)_m\text{-}A\text{-}(C)_n \quad \text{(I),}$$

wherein A is the polypeptide of SEQ ID NO: 1, B and C are independently any mutually identical or different polypeptides with the value of molecular weight being a multiple of 5 kDa, and m and n are independently 0 or any integer larger than 0; and
(b) one or more solvents for stabilizing the recombinant proteins.

2. The auto-developing and regularly-weighted protein molecular weight marker kit of claim 1, wherein B and C are selected from thioredoxin comprising the amino acid sequence of SEQ ID NO: 2, glutathione-S-transferase comprising the amino acid sequence of SEQ ID NO: 3, maltose-binding protein comprising the amino acid sequence of SEQ ID NO: 4, or artificial peptide sequence comprising the amino acid sequence of SEQ ID NO: 5.

3. The auto-developing and regularly-weighted protein molecular weight marker kit of claim 1, wherein the plurality of recombinant proteins having formula (I) are selected from the group consisting of the polypeptide of SEQ ID NO: 1, the polypeptide of SEQ ID NO: 6, the polypeptide of SEQ ID NO: 7, the polypeptide of SEQ ID NO: 8, the polypeptide of SEQ ID NO: 9, the polypeptide of SEQ ID NO: 10, the polypeptide of SEQ ID NO: 11, the polypeptide of SEQ ID NO: 12, the polypeptide of SEQ ID NO: 13, the polypeptide of SEQ ID NO: 14, the polypeptide of SEQ ID NO: 15, the polypeptide of SEQ ID NO: 16, the polypeptide of SEQ ID NO: 17, and the polypeptide of SEQ ID NO: 18.

4. The auto-developing and regularly-weighted protein molecular weight marker kit of claim 1, wherein the polypeptide of SEQ ID NO: 1 is recognized by an antibody selected from the group consisting of anti-His6-tag antibody, anti-HA-tag antibody, anti-T7-tag antibody, anti-E-tag antibody, anti-VSV-g-tag antibody, anti-V5-tag antibody, anti-AU5-tag antibody, anti-S-tag antibody, anti-HSV-tag antibody, anti-FLAG-tag antibody, anti-Lumio-tag antibody, anti-Glu-Glu-tag antibody, anti-cMyc-tag antibody, and anti-AU1-tag antibody.

5. The auto-developing and regularly-weighted protein molecular weight marker kit of claim 1, which is used as protein marker for SDS-PAGE.

6. The auto-developing and regularly-weighted protein molecular weight marker kit of claim 1, which is used as protein marker and/or positive control of Western blotting utilized antibodies below for color development: anti-His6-tag antibody, anti-HA-tag antibody, anti-T7-tag antibody, anti-E-tag antibody, anti-VSV-g-tag antibody, anti-V5-tag antibody, anti-AU5-tag antibody, anti-S-tag antibody, anti-HSV-tag antibody, anti-FLAG-tag antibody, anti-Lumio-tag antibody, anti-Glu-Glu-tag antibody, anti-cMyc-tag antibody, or anti-AU1-tag antibody.

7. A method for preparing an auto-developing and regularly-weighted protein molecular weight marker kit comprising:
(a) constructing vectors, which comprises a plurality of nucleotide sequences encoding recombinant proteins of formula (I) independently, to obtain recombinant protein expression vectors, $$(B)_m\text{-}A\text{-}(C)_n \qquad (I),$$

wherein A is the polypeptide of SEQ ID NO: 1, B and C are independently any mutually identical or different polypeptides with the value of molecular weight being a multiple of 5 kDa, and m and n are independently 0 or any integer larger than 0;
(b) transforming the recombinant protein expression vectors into competent cells;
(c) selecting the competent cells carrying the recombinant protein expression vectors;
(d) inducing the competent cells carrying the recombinant protein expression vectors to express the recombinant proteins by administrating an inducer; and
extracting each of recombinant protein with different molecular weights independently, and mixing a plurality of recombinant proteins with one or more recombinant protein stabilizing solvents.

8. The method of claim 7, which further comprises a step of purifying the recombinant proteins, which is performed by using an affinity column or 5200 gel filtration, before mixing the plurality of recombinant proteins with one or more recombinant protein stabilizing solvents to increase the recombinant protein purity.

9. The method of claim 7, wherein the plurality of nucleotide sequences encoding recombinant protein of formula (I) are selected from the group consisting of a nucleotide sequence encoding the polypeptide of SEQ ID NO: 1, a nucleotide sequence encoding the polypeptide of SEQ ID NO: 6, a nucleotide sequence encoding the polypeptide of SEQ ID NO: 7, a nucleotide sequence encoding the polypeptide of SEQ ID NO: 8, a nucleotide sequence encoding the polypeptide of SEQ ID NO: 9, a nucleotide sequence encoding the polypeptide of SEQ ID NO: 10, a nucleotide sequence encoding the polypeptide of SEQ ID NO: 11, a nucleotide sequence encoding the polypeptide of SEQ ID NO: 12, a nucleotide sequence encoding the polypeptide of SEQ ID NO: 13, a nucleotide sequence encoding the polypeptide of SEQ ID NO: 14, a nucleotide sequence encoding the polypeptide of SEQ ID NO: 15, a nucleotide sequence encoding the polypeptide of SEQ ID NO: 16, a nucleotide sequence encoding the polypeptide of SEQ ID NO: 17, and a nucleotide sequence encoding the polypeptide of SEQ ID NO: 18.

* * * * *

SEQUENCE LISTING

<160> NUMBER OF SEQ ID NOS: 68

<210> SEQ ID NO 1
<211> LENGTH: 132
<212> TYPE: PRT
<213> ORGANISM: Artificial
<220> FEATURE:
<223> OTHER INFORMATION: Synthesized 14-tag protein
<220> FEATURE:
<221> NAME/KEY: PEPTIDE
<222> LOCATION: (1)..(132)

<400> SEQUENCE: 1

Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
    50                  55                  60

Leu Leu Gly Leu Asp Ser Thr Asp Phe Tyr Leu Lys Glu Thr Ala Ala
65                  70                  75                  80

Ala Lys Phe Glu Arg Gln His Met Asp Ser Gln Pro Glu Leu Ala Pro
                85                  90                  95

Glu Asp Pro Glu Asp Tyr Lys Asp Asp Asp Lys Cys Cys Pro Gly
            100                 105                 110

Cys Cys Glu Glu Glu Glu Tyr Met Pro Met Glu Gln Lys Leu Ile Ser
        115                 120                 125

Glu Glu Asp Leu
    130

<210> SEQ ID NO 2
<211> LENGTH: 92
<212> TYPE: PRT
<213> ORGANISM: Artificial
<220> FEATURE:
<223> OTHER INFORMATION: Synthesized TRX protein
<220> FEATURE:
<221> NAME/KEY: PEPTIDE
<222> LOCATION: (1)..(92)

<400> SEQUENCE: 2

Ser Asp Lys Ile Ile His Leu Thr Asp Asp Ser Phe Asp Thr Asp Val
1               5                   10                  15

Leu Lys Ala Asp Gly Ala Ile Leu Val Asp Phe Trp Ala Glu Trp Cys
            20                  25                  30

Gly Pro Cys Lys Met Ile Ala Pro Ile Leu Asp Glu Ile Ala Asp Glu
        35                  40                  45

Tyr Gln Gly Lys Leu Thr Val Ala Lys Leu Asn Ile Asp Gln Asn Pro
    50                  55                  60

Gly Thr Ala Pro Lys Tyr Gly Ile Arg Gly Ile Pro Thr Leu Leu Leu
65                  70                  75                  80

Phe Lys Asn Gly Glu Val Ala Ala Thr Lys Val Gly
                85                  90

<210> SEQ ID NO 3
<211> LENGTH: 212
<212> TYPE: PRT
<213> ORGANISM: Artificial
<220> FEATURE:

<223> OTHER INFORMATION: Synthesized GST protein
<220> FEATURE:
<221> NAME/KEY: PEPTIDE
<222> LOCATION: (1)..(212)

<400> SEQUENCE: 3

```
Leu Glu Met Ser Pro Ile Leu Gly Tyr Trp Lys Ile Lys Gly Leu Val
1               5                   10                  15

Gln Pro Thr Arg Leu Leu Leu Glu Tyr Leu Glu Glu Lys Tyr Glu Glu
            20                  25                  30

His Leu Tyr Glu Arg Asp Glu Gly Asp Lys Trp Arg Asn Lys Lys Phe
        35                  40                  45

Glu Leu Gly Leu Glu Phe Pro Asn Leu Pro Tyr Tyr Ile Asp Gly Asp
    50                  55                  60

Val Lys Leu Thr Gln Ser Met Ala Ile Ile Arg Tyr Ile Ala Asp Lys
65                  70                  75                  80

His Asn Met Leu Gly Gly Cys Pro Lys Glu Arg Ala Glu Ile Ser Met
                85                  90                  95

Leu Glu Gly Ala Val Leu Asp Ile Arg Tyr Gly Val Ser Arg Ile Ala
            100                 105                 110

Tyr Ser Lys Asp Phe Glu Thr Leu Lys Val Asp Phe Leu Ser Lys Leu
        115                 120                 125

Pro Glu Met Leu Lys Met Phe Glu Asp Arg Leu Cys His Lys Thr Tyr
    130                 135                 140

Leu Asn Gly Asp His Val Thr His Pro Asp Phe Met Leu Tyr Asp Ala
145                 150                 155                 160

Leu Asp Val Val Leu Tyr Met Asp Pro Met Cys Leu Asp Ala Phe Pro
                165                 170                 175

Lys Leu Val Cys Phe Lys Lys Arg Ile Glu Ala Ile Pro Gln Ile Asp
            180                 185                 190

Lys Tyr Leu Lys Ser Ser Lys Tyr Met His Pro Trp Val Asn Asp Ile
        195                 200                 205

Val Asp Glu Phe
    210
```

<210> SEQ ID NO 4
<211> LENGTH: 366
<212> TYPE: PRT
<213> ORGANISM: Artificial
<220> FEATURE:
<223> OTHER INFORMATION: Synthesized MBP1 protein
<220> FEATURE:
<221> NAME/KEY: PEPTIDE
<222> LOCATION: (1)..(366)

<400> SEQUENCE: 4

```
Val Asp Met His Lys Ile Glu Glu Gly Lys Leu Val Ile Trp Ile Asn
1               5                   10                  15

Gly Asp Lys Gly Tyr Asn Gly Leu Ala Glu Val Gly Lys Lys Phe Glu
            20                  25                  30

Lys Asp Thr Gly Ile Lys Val Thr Val Glu His Pro Asp Lys Leu Glu
        35                  40                  45

Glu Lys Phe Pro Gln Val Ala Ala Thr Gly Asp Gly Pro Asp Ile Ile
    50                  55                  60

Phe Trp Ala His Asp Arg Phe Gly Gly Tyr Ala Gln Ser Gly Leu Leu
65                  70                  75                  80

Ala Glu Ile Thr Pro Asp Lys Ala Phe Gln Asp Lys Leu Tyr Pro Phe
                85                  90                  95
```

Thr Trp Asp Ala Val Arg Tyr Asn Gly Lys Leu Ile Ala Tyr Pro Ile
            100                 105                 110

Ala Val Glu Ala Leu Ser Leu Ile Tyr Asn Lys Asp Leu Leu Pro Asn
        115                 120                 125

Pro Pro Lys Thr Trp Glu Glu Ile Pro Ala Leu Asp Lys Glu Leu Lys
130                 135                 140

Ala Lys Gly Lys Ser Ala Leu Met Phe Asn Leu Gln Glu Pro Tyr Phe
145                 150                 155                 160

Thr Trp Pro Pro Ile Ala Ala Asp Gly Gly Tyr Ala Phe Lys Tyr Glu
                165                 170                 175

Asn Gly Lys Tyr Asp Ile Lys Asp Val Gly Val Asp Asn Ala Gly Ala
            180                 185                 190

Lys Ala Gly Leu Thr Phe Leu Val Asp Leu Ile Lys Asn Lys His Met
        195                 200                 205

Asn Ala Asp Thr Asp Tyr Ser Ile Ala Glu Ala Phe Asn Lys Gly
            210                 215                 220

Glu Thr Ala Met Thr Ile Asn Gly Pro Trp Ala Trp Ser Asn Ile Asp
225                 230                 235                 240

Thr Ser Lys Val Asn Tyr Gly Val Thr Val Leu Pro Thr Phe Lys Gly
                245                 250                 255

Gln Pro Ser Lys Pro Phe Val Gly Val Leu Ser Ala Gly Ile Asn Ala
            260                 265                 270

Ala Ser Pro Asn Lys Glu Leu Ala Lys Glu Phe Leu Glu Asn Tyr Leu
        275                 280                 285

Leu Thr Asp Glu Gly Leu Glu Ala Val Asn Lys Asp Lys Pro Leu Gly
        290                 295                 300

Ala Val Ala Leu Lys Ser Tyr Glu Glu Glu Leu Ala Lys Asp Pro Arg
305                 310                 315                 320

Ile Ala Ala Thr Met Glu Asn Ala Gln Lys Gly Glu Ile Met Pro Asn
                325                 330                 335

Ile Pro Gln Met Ser Ala Phe Trp Tyr Ala Val Arg Thr Ala Val Ile
            340                 345                 350

Asn Ala Ala Ser Gly Arg Gln Thr Val Asp Glu Ala Val Asn
        355                 360                 365

<210> SEQ ID NO 5
<211> LENGTH: 42
<212> TYPE: PRT
<213> ORGANISM: Artificial
<220> FEATURE:
<223> OTHER INFORMATION: Synthesized 5 kDa peptide
<220> FEATURE:
<221> NAME/KEY: PEPTIDE
<222> LOCATION: (1)..(42)

<400> SEQUENCE: 5

Leu Glu Gly Asp Val Lys Leu Thr Gln Ser Tyr Ala Ser Met Thr Gly
1               5                   10                  15

Gly Gln Gln Met Gly Arg Asp Leu Tyr Asp Asp Asp Lys Asp Arg
            20                  25                  30

Ser Ala Ala Gly Thr Met Glu Phe Glu Ala
        35                  40

<210> SEQ ID NO 6
<211> LENGTH: 174
<212> TYPE: PRT
<213> ORGANISM: Artificial

<220> FEATURE:
<223> OTHER INFORMATION: Synthesized 20kDa peptide
<220> FEATURE:
<221> NAME/KEY: PEPTIDE
<222> LOCATION: (1)..(174)

<400> SEQUENCE: 6

Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
50                  55                  60

Leu Leu Gly Leu Asp Ser Thr Asp Phe Tyr Leu Lys Glu Thr Ala Ala
65                  70                  75                  80

Ala Lys Phe Glu Arg Gln His Met Asp Ser Gln Pro Glu Leu Ala Pro
                85                  90                  95

Glu Asp Pro Glu Asp Tyr Lys Asp Asp Asp Lys Cys Cys Pro Gly
            100                 105                 110

Cys Cys Glu Glu Glu Glu Tyr Met Pro Met Glu Gln Lys Leu Ile Ser
        115                 120                 125

Glu Glu Asp Leu Leu Glu Gly Asp Val Lys Leu Thr Gln Ser Tyr Ala
130                 135                 140

Ser Met Thr Gly Gly Gln Gln Met Gly Arg Asp Leu Tyr Asp Asp Asp
145                 150                 155                 160

Asp Lys Asp Arg Ser Ala Ala Gly Thr Met Glu Phe Glu Ala
                165                 170

<210> SEQ ID NO 7
<211> LENGTH: 230
<212> TYPE: PRT
<213> ORGANISM: Artificial
<220> FEATURE:
<223> OTHER INFORMATION: Synthesized 25 kDa peptide
<220> FEATURE:
<221> NAME/KEY: PEPTIDE
<222> LOCATION: (1)..(230)

<400> SEQUENCE: 7

Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
50                  55                  60

Leu Leu Gly Leu Asp Ser Thr Asp Phe Tyr Leu Lys Glu Thr Ala Ala
65                  70                  75                  80

Ala Lys Phe Glu Arg Gln His Met Asp Ser Gln Pro Glu Leu Ala Pro
                85                  90                  95

Glu Asp Pro Glu Asp Tyr Lys Asp Asp Asp Lys Cys Cys Pro Gly
            100                 105                 110

Cys Cys Glu Glu Glu Glu Tyr Met Pro Met Glu Gln Lys Leu Ile Ser
        115                 120                 125

Glu Glu Asp Leu Leu Asp Glu Phe Ser Asp Lys Ile Ile His Leu Thr

```
            130             135             140
Asp Asp Ser Phe Asp Thr Asp Val Leu Lys Ala Asp Gly Ala Ile Leu
145                 150                 155                 160

Val Asp Phe Trp Ala Glu Trp Cys Gly Pro Cys Lys Met Ile Ala Pro
                165                 170                 175

Ile Leu Asp Glu Ile Ala Asp Glu Tyr Gln Gly Lys Leu Thr Val Ala
            180                 185                 190

Lys Leu Asn Ile Asp Gln Asn Pro Gly Thr Ala Pro Lys Tyr Gly Ile
                195                 200                 205

Arg Gly Ile Pro Thr Leu Leu Leu Phe Lys Asn Gly Glu Val Ala Ala
            210                 215                 220

Thr Lys Val Gly Lys Leu
225                 230

<210> SEQ ID NO 8
<211> LENGTH: 266
<212> TYPE: PRT
<213> ORGANISM: Artificial
<220> FEATURE:
<223> OTHER INFORMATION: Synthesized 30 kDa peptide
<220> FEATURE:
<221> NAME/KEY: PEPTIDE
<222> LOCATION: (1)..(266)

<400> SEQUENCE: 8

Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
    50                  55                  60

Leu Leu Gly Leu Asp Ser Thr Asp Phe Tyr Leu Lys Glu Thr Ala Ala
65                  70                  75                  80

Ala Lys Phe Glu Arg Gln His Met Asp Ser Gln Pro Glu Leu Ala Pro
                85                  90                  95

Glu Asp Pro Glu Asp Tyr Lys Asp Asp Asp Lys Cys Cys Pro Gly Cys Gly
            100                 105                 110

Cys Cys Glu Glu Glu Tyr Met Pro Met Glu Gln Lys Leu Ile Ser
        115                 120                 125

Glu Glu Asp Leu Leu Glu Gly Asp Val Lys Leu Thr Gln Ser Tyr Ala
    130                 135                 140

Ser Met Thr Gly Gly Gln Gln Met Gly Arg Asp Leu Tyr Asp Asp Asp
145                 150                 155                 160

Asp Lys Asp Arg Ser Ala Ala Gly Thr Met Glu Phe Ser Asp Lys Ile
                165                 170                 175

Ile His Leu Thr Asp Asp Ser Phe Asp Thr Asp Val Leu Lys Ala Asp
            180                 185                 190

Gly Ala Ile Leu Val Asp Phe Trp Ala Glu Trp Cys Gly Pro Cys Lys
        195                 200                 205

Met Ile Ala Pro Ile Leu Asp Glu Ile Ala Asp Glu Tyr Gln Gly Lys
    210                 215                 220

Leu Thr Val Ala Lys Leu Asn Ile Asp Gln Asn Pro Gly Thr Ala Pro
225                 230                 235                 240

Lys Tyr Gly Ile Arg Gly Ile Pro Thr Leu Leu Leu Phe Lys Asn Gly
```

```
                        245                 250                 255
Glu Val Ala Ala Thr Lys Val Gly Lys Leu
            260                 265

<210> SEQ ID NO 9
<211> LENGTH: 344
<212> TYPE: PRT
<213> ORGANISM: Artificial
<220> FEATURE:
<223> OTHER INFORMATION: Synthesized 40 kDa peptide
<220> FEATURE:
<221> NAME/KEY: PEPTIDE
<222> LOCATION: (1)..(344)

<400> SEQUENCE: 9

Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
50                  55                  60

Leu Leu Gly Leu Asp Ser Thr Asp Phe Tyr Leu Lys Glu Thr Ala Ala
65                  70                  75                  80

Ala Lys Phe Glu Arg Gln His Met Asp Ser Gln Pro Glu Leu Ala Pro
                85                  90                  95

Glu Asp Pro Glu Asp Tyr Lys Asp Asp Asp Lys Cys Cys Pro Gly
            100                 105                 110

Cys Cys Glu Glu Glu Glu Tyr Met Pro Met Glu Gln Lys Leu Ile Ser
        115                 120                 125

Glu Glu Asp Leu Leu Glu Met Ser Pro Ile Leu Gly Tyr Trp Lys Ile
    130                 135                 140

Lys Gly Leu Val Gln Pro Thr Arg Leu Leu Leu Glu Tyr Leu Glu Glu
145                 150                 155                 160

Lys Tyr Glu Glu His Leu Tyr Glu Arg Asp Glu Gly Asp Lys Trp Arg
                165                 170                 175

Asn Lys Lys Phe Glu Leu Gly Leu Glu Phe Pro Asn Leu Pro Tyr Tyr
            180                 185                 190

Ile Asp Gly Asp Val Lys Leu Thr Gln Ser Met Ala Ile Ile Arg Tyr
        195                 200                 205

Ile Ala Asp Lys His Asn Met Leu Gly Gly Cys Pro Lys Glu Arg Ala
    210                 215                 220

Glu Ile Ser Met Leu Glu Gly Ala Val Leu Asp Ile Arg Tyr Gly Val
225                 230                 235                 240

Ser Arg Ile Ala Tyr Ser Lys Asp Phe Glu Thr Leu Lys Val Asp Phe
                245                 250                 255

Leu Ser Lys Leu Pro Glu Met Leu Lys Met Phe Glu Asp Arg Leu Cys
            260                 265                 270

His Lys Thr Tyr Leu Asn Gly Asp His Val Thr His Pro Asp Phe Met
        275                 280                 285

Leu Tyr Asp Ala Leu Asp Val Val Leu Tyr Met Asp Pro Met Cys Leu
    290                 295                 300

Asp Ala Phe Pro Lys Leu Val Cys Phe Lys Lys Arg Ile Glu Ala Ile
305                 310                 315                 320

Pro Gln Ile Asp Lys Tyr Leu Lys Ser Ser Lys Tyr Met His Pro Trp
```

```
                    325                 330                 335

Val Asn Asp Ile Val Asp Glu Phe
            340

<210> SEQ ID NO 10
<211> LENGTH: 438
<212> TYPE: PRT
<213> ORGANISM: Artificial
<220> FEATURE:
<223> OTHER INFORMATION: Synthesized 50 kDa peptide
<220> FEATURE:
<221> NAME/KEY: PEPTIDE
<222> LOCATION: (1)..(438)

<400> SEQUENCE: 10

Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
    50                  55                  60

Leu Leu Gly Leu Asp Ser Thr Asp Phe Tyr Leu Lys Glu Thr Ala Ala
65                  70                  75                  80

Ala Lys Phe Glu Arg Gln His Met Asp Ser Gln Pro Glu Leu Ala Pro
            85                  90                  95

Glu Asp Pro Glu Asp Tyr Lys Asp Asp Asp Lys Cys Cys Pro Gly
        100                 105                 110

Cys Cys Glu Glu Glu Glu Tyr Met Pro Met Glu Gln Lys Leu Ile Ser
    115                 120                 125

Glu Glu Asp Leu Leu Glu Met Ser Pro Ile Leu Gly Tyr Trp Lys Ile
130                 135                 140

Lys Gly Leu Val Gln Pro Thr Arg Leu Leu Leu Glu Tyr Leu Glu Glu
145                 150                 155                 160

Lys Tyr Glu Glu His Leu Tyr Glu Arg Asp Glu Gly Asp Lys Trp Arg
            165                 170                 175

Asn Lys Lys Phe Glu Leu Gly Leu Glu Phe Pro Asn Leu Pro Tyr Tyr
        180                 185                 190

Ile Asp Gly Asp Val Lys Leu Thr Gln Ser Met Ala Ile Ile Arg Tyr
    195                 200                 205

Ile Ala Asp Lys His Asn Met Leu Gly Gly Cys Pro Lys Glu Arg Ala
    210                 215                 220

Glu Ile Ser Met Leu Glu Gly Ala Val Leu Asp Ile Arg Tyr Gly Val
225                 230                 235                 240

Ser Arg Ile Ala Tyr Ser Lys Asp Phe Glu Thr Leu Lys Val Asp Phe
            245                 250                 255

Leu Ser Lys Leu Pro Glu Met Leu Lys Met Phe Glu Asp Arg Leu Cys
        260                 265                 270

His Lys Thr Tyr Leu Asn Gly Asp His Val Thr His Pro Asp Phe Met
    275                 280                 285

Leu Tyr Asp Ala Leu Asp Val Val Leu Tyr Met Asp Pro Met Cys Leu
    290                 295                 300

Asp Ala Phe Pro Lys Leu Val Cys Phe Lys Lys Arg Ile Glu Ala Ile
305                 310                 315                 320

Pro Gln Ile Asp Lys Tyr Leu Lys Ser Ser Lys Tyr Met His Pro Trp
```

```
                325                 330                 335
Val Asn Asp Ile Val Asp Glu Phe Ser Asp Lys Ile Ile His Leu Thr
            340                 345                 350

Asp Asp Ser Phe Asp Thr Asp Val Leu Lys Ala Asp Gly Ala Ile Leu
            355                 360                 365

Val Asp Phe Trp Ala Glu Trp Cys Gly Pro Cys Lys Met Ile Ala Pro
370                 375                 380

Ile Leu Asp Glu Ile Ala Asp Glu Tyr Gln Gly Lys Leu Thr Val Ala
385                 390                 395                 400

Lys Leu Asn Ile Asp Gln Asn Pro Gly Thr Ala Pro Lys Tyr Gly Ile
            405                 410                 415

Arg Gly Ile Pro Thr Leu Leu Leu Phe Lys Asn Gly Glu Val Ala Ala
            420                 425                 430

Thr Lys Val Gly Lys Leu
            435

<210> SEQ ID NO 11
<211> LENGTH: 561
<212> TYPE: PRT
<213> ORGANISM: Artificial
<220> FEATURE:
<223> OTHER INFORMATION: Synthesized 60 kDa peptide
<220> FEATURE:
<221> NAME/KEY: PEPTIDE
<222> LOCATION: (1)..(561)

<400> SEQUENCE: 11

Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
50                  55                  60

Leu Leu Gly Leu Asp Ser Thr Asp Phe Tyr Leu Lys Glu Thr Ala Ala
65                  70                  75                  80

Ala Lys Phe Glu Arg Gln His Met Asp Ser Gln Pro Glu Leu Ala Pro
                85                  90                  95

Glu Asp Pro Glu Asp Tyr Lys Asp Asp Asp Lys Cys Cys Pro Gly
            100                 105                 110

Cys Cys Glu Glu Glu Tyr Met Pro Met Glu Gln Lys Leu Ile Ser
            115                 120                 125

Glu Glu Asp Leu Leu Glu Met Ser Pro Ile Leu Gly Tyr Trp Lys Ile
        130                 135                 140

Lys Gly Leu Val Gln Pro Thr Arg Leu Leu Leu Glu Tyr Leu Glu Glu
145                 150                 155                 160

Lys Tyr Glu Glu His Leu Tyr Glu Arg Asp Glu Gly Asp Lys Trp Arg
                165                 170                 175

Asn Lys Lys Phe Glu Leu Gly Leu Glu Phe Pro Asn Leu Pro Tyr Tyr
            180                 185                 190

Ile Asp Gly Asp Val Lys Leu Thr Gln Ser Met Ala Ile Ile Arg Tyr
        195                 200                 205

Ile Ala Asp Lys His Asn Met Leu Gly Gly Cys Pro Lys Glu Arg Ala
    210                 215                 220

Glu Ile Ser Met Leu Glu Gly Ala Val Leu Asp Ile Arg Tyr Gly Val
```

```
                    225                 230                 235                 240
            Ser Arg Ile Ala Tyr Ser Lys Asp Phe Glu Thr Leu Lys Val Asp Phe
                            245                 250                 255

Leu Ser Lys Leu Pro Glu Met Leu Lys Met Phe Glu Asp Arg Leu Cys
                        260                 265                 270

His Lys Thr Tyr Leu Asn Gly Asp His Val Thr His Pro Asp Phe Met
                        275                 280                 285

Leu Tyr Asp Ala Leu Asp Val Val Leu Tyr Met Asp Pro Met Cys Leu
                        290                 295                 300

Asp Ala Phe Pro Lys Leu Val Cys Phe Lys Lys Arg Ile Glu Ala Ile
            305                 310                 315                 320

Pro Gln Ile Asp Lys Tyr Leu Lys Ser Ser Lys Tyr Met His Pro Trp
                            325                 330                 335

Val Asn Asp Ile Val Asp Glu Phe Ser Asp Lys Ile Ile His Leu Thr
                        340                 345                 350

Asp Asp Ser Phe Asp Thr Asp Val Leu Lys Ala Asp Gly Ala Ile Leu
                        355                 360                 365

Val Asp Phe Trp Ala Glu Trp Cys Gly Pro Cys Lys Met Ile Ala Pro
                    370                 375                 380

Ile Leu Asp Glu Ile Ala Asp Glu Tyr Gln Gly Lys Leu Thr Val Ala
            385                 390                 395                 400

Lys Leu Asn Ile Asp Gln Asn Pro Gly Thr Ala Pro Lys Tyr Gly Ile
                            405                 410                 415

Arg Gly Ile Pro Thr Leu Leu Leu Phe Lys Asn Gly Glu Val Ala Ala
                        420                 425                 430

Thr Lys Val Gly Lys Leu Ala Ser Met Thr Gly Gly Gln Gln Met Gly
                        435                 440                 445

Arg Asp Leu Tyr Asp Asp Asp Lys Asp Arg Ser Ala Ala Gly Thr
                    450                 455                 460

Met Glu Phe Ser Asp Lys Ile Ile His Leu Thr Asp Asp Ser Phe Asp
            465                 470                 475                 480

Thr Asp Val Leu Lys Ala Asp Gly Ala Ile Leu Val Asp Phe Trp Ala
                            485                 490                 495

Glu Trp Cys Gly Pro Cys Lys Met Ile Ala Pro Ile Leu Asp Glu Ile
                        500                 505                 510

Ala Asp Glu Tyr Gln Gly Lys Leu Thr Val Ala Lys Leu Asn Ile Asp
                        515                 520                 525

Gln Asn Pro Gly Thr Ala Pro Lys Tyr Gly Ile Arg Gly Ile Pro Thr
                    530                 535                 540

Leu Leu Leu Phe Lys Asn Gly Glu Val Ala Ala Thr Lys Val Gly Lys
            545                 550                 555                 560

Leu

<210> SEQ ID NO 12
<211> LENGTH: 704
<212> TYPE: PRT
<213> ORGANISM: Artificial
<220> FEATURE:
<223> OTHER INFORMATION: Synthesized 80 kDa peptide
<220> FEATURE:
<221> NAME/KEY: PEPTIDE
<222> LOCATION: (1)..(704)

<400> SEQUENCE: 12

Met Arg Gly Ser His His His His His His Tyr Pro Tyr Asp Val Pro
            1               5                   10                  15
```

```
Asp Tyr Ala Asp Thr Tyr Arg Tyr Ile Met Ala Ser Met Thr Gly Gly
             20                  25                  30

Gln Gln Met Gly Ala Pro Val Pro Tyr Pro Asp Pro Leu Glu Pro Arg
             35                  40              45

Tyr Thr Asp Ile Glu Met Asn Arg Leu Gly Lys Pro Ile Pro Asn Pro
 50                  55                  60

Leu Leu Gly Leu Asp Ser Thr Asp Phe Tyr Leu Lys Glu Thr Ala Ala
 65                  70                  75                  80

Ala Lys Phe Glu Arg Gln His Met Asp Ser Gln Pro Glu Leu Ala Pro
                 85                  90                  95

Glu Asp Pro Glu Asp Tyr Lys Asp Asp Asp Lys Cys Cys Pro Gly
             100                 105                 110

Cys Cys Glu Glu Glu Glu Tyr Met Pro Met Glu Gln Lys Leu Ile Ser
             115                 120                 125

Glu Glu Asp Leu Leu Glu Met Ser Pro Ile Leu Gly Tyr Trp Lys Ile
 130                 135                 140

Lys Gly Leu Val Gln Pro Thr Arg Leu Leu Leu Glu Tyr Leu Glu Glu
145                 150                 155                 160

Lys Tyr Glu Glu His Leu Tyr Glu Arg Asp Glu Gly Asp Lys Trp Arg
                 165                 170                 175

Asn Lys Lys Phe Glu Leu Gly Leu Glu Phe Pro Asn Leu Pro Tyr Tyr
             180                 185                 190

Ile Asp Gly Asp Val Lys Leu Thr Gln Ser Met Ala Ile Ile Arg Tyr
             195                 200                 205

Ile Ala Asp Lys His Asn Met Leu Gly Gly Cys Pro Lys Glu Arg Ala
             210                 215                 220

Glu Ile Ser Met Leu Glu Gly Ala Val Leu Asp Ile Arg Tyr Gly Val
225                 230                 235                 240

Ser Arg Ile Ala Tyr Ser Lys Asp Phe Glu Thr Leu Lys Val Asp Phe
                 245                 250                 255

Leu Ser Lys Leu Pro Glu Met Leu Lys Met Phe Glu Asp Arg Leu Cys
             260                 265                 270

His Lys Thr Tyr Leu Asn Gly Asp His Val Thr His Pro Asp Phe Met
             275                 280                 285

Leu Tyr Asp Ala Leu Asp Val Val Leu Tyr Met Asp Pro Met Cys Leu
 290                 295                 300

Asp Ala Phe Pro Lys Leu Val Cys Phe Lys Lys Arg Ile Glu Ala Ile
305                 310                 315                 320

Pro Gln Ile Asp Lys Tyr Leu Lys Ser Ser Lys Tyr Met His Pro Trp
                 325                 330                 335

Val Asn Lys Ile Glu Glu Gly Lys Leu Val Ile Trp Ile Asn Gly Asp
             340                 345                 350

Lys Gly Tyr Asn Gly Leu Ala Glu Val Gly Lys Lys Phe Glu Lys Asp
             355                 360                 365

Thr Gly Ile Lys Val Thr Val Glu His Pro Asp Lys Leu Glu Glu Lys
             370                 375                 380

Phe Pro Gln Val Ala Ala Thr Gly Asp Gly Pro Asp Ile Ile Phe Trp
385                 390                 395                 400

Ala His Asp Arg Phe Gly Gly Tyr Ala Gln Ser Gly Leu Leu Ala Glu
                 405                 410                 415

Ile Thr Pro Asp Lys Ala Phe Gln Asp Lys Leu Tyr Pro Phe Thr Trp
             420                 425                 430
```

```
Asp Ala Val Arg Tyr Asn Gly Lys Leu Ile Ala Tyr Pro Ile Ala Val
            435                 440                 445

Glu Ala Leu Ser Leu Ile Tyr Asn Lys Asp Leu Leu Pro Asn Pro Pro
        450                 455                 460

Lys Thr Trp Glu Glu Ile Pro Ala Leu Asp Lys Glu Leu Lys Ala Lys
465                 470                 475                 480

Gly Lys Ser Ala Leu Met Phe Asn Leu Gln Glu Pro Tyr Phe Thr Trp
                485                 490                 495

Pro Leu Ile Ala Ala Asp Gly Gly Tyr Ala Phe Lys Tyr Glu Asn Gly
            500                 505                 510

Lys Tyr Asp Ile Lys Asp Val Gly Val Asp Asn Ala Gly Ala Lys Ala
        515                 520                 525

Gly Leu Thr Phe Leu Val Asp Leu Ile Lys Asn Lys His Met Asn Ala
530                 535                 540

Asp Thr Asp Tyr Ser Ile Ala Glu Ala Ala Phe Asn Lys Gly Glu Thr
545                 550                 555                 560

Ala Met Thr Ile Asn Gly Pro Trp Ala Trp Ser Asn Ile Asp Thr Ser
                565                 570                 575

Lys Val Asn Tyr Gly Val Thr Val Leu Pro Thr Phe Lys Gly Gln Pro
            580                 585                 590

Ser Lys Pro Phe Val Gly Val Leu Ser Ala Gly Ile Asn Ala Ala Ser
        595                 600                 605

Pro Asn Lys Glu Leu Ala Lys Glu Phe Leu Glu Asn Tyr Leu Leu Thr
610                 615                 620

Asp Glu Gly Leu Glu Ala Val Asn Lys Asp Lys Pro Leu Gly Ala Val
625                 630                 635                 640

Ala Leu Lys Ser Tyr Glu Glu Glu Leu Ala Lys Asp Pro Arg Ile Ala
                645                 650                 655

Ala Thr Met Glu Asn Ala Gln Lys Gly Glu Ile Met Pro Asn Ile Pro
            660                 665                 670

Gln Met Ser Ala Phe Trp Tyr Ala Val Arg Thr Ala Val Ile Asn Ala
        675                 680                 685

Ala Ser Gly Arg Gln Thr Val Asp Glu Ala Asp Ile Pro Trp Lys Leu
690                 695                 700

<210> SEQ ID NO 13
<211> LENGTH: 921
<212> TYPE: PRT
<213> ORGANISM: Artificial
<220> FEATURE:
<223> OTHER INFORMATION: Synthesized 100 kDa peptide
<220> FEATURE:
<221> NAME/KEY: PEPTIDE
<222> LOCATION: (1)..(921)

<400> SEQUENCE: 13

Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
    50                  55                  60

Leu Leu Gly Leu Asp Ser Thr Asp Phe Tyr Leu Lys Glu Thr Ala Ala
65                  70                  75                  80
```

```
Ala Lys Phe Glu Arg Gln His Met Asp Ser Gln Pro Glu Leu Ala Pro
                85                  90                  95
Glu Asp Pro Glu Asp Tyr Lys Asp Asp Asp Lys Cys Cys Pro Gly
            100                 105                 110
Cys Cys Glu Glu Glu Tyr Met Pro Met Glu Gln Lys Leu Ile Ser
        115                 120                 125
Glu Glu Asp Leu Leu Glu Met Ser Pro Ile Leu Gly Tyr Trp Lys Ile
    130                 135                 140
Lys Gly Leu Val Gln Pro Thr Arg Leu Leu Leu Glu Tyr Leu Glu Glu
145                 150                 155                 160
Lys Tyr Glu Glu His Leu Tyr Glu Arg Asp Glu Gly Asp Lys Trp Arg
                165                 170                 175
Asn Lys Lys Phe Glu Leu Gly Leu Glu Phe Pro Asn Leu Pro Tyr Tyr
            180                 185                 190
Ile Asp Gly Asp Val Lys Leu Thr Gln Ser Met Ala Ile Ile Arg Tyr
        195                 200                 205
Ile Ala Asp Lys His Asn Met Leu Gly Gly Cys Pro Lys Glu Arg Ala
    210                 215                 220
Glu Ile Ser Met Leu Glu Gly Ala Val Leu Asp Ile Arg Tyr Gly Val
225                 230                 235                 240
Ser Arg Ile Ala Tyr Ser Lys Asp Phe Glu Thr Leu Lys Val Asp Phe
                245                 250                 255
Leu Ser Lys Leu Pro Glu Met Leu Lys Met Phe Glu Asp Arg Leu Cys
            260                 265                 270
His Lys Thr Tyr Leu Asn Gly Asp His Val Thr His Pro Asp Phe Met
        275                 280                 285
Leu Tyr Asp Ala Leu Asp Val Val Leu Tyr Met Asp Pro Met Cys Leu
    290                 295                 300
Asp Ala Phe Pro Lys Leu Val Cys Phe Lys Lys Arg Ile Glu Ala Ile
305                 310                 315                 320
Pro Gln Ile Asp Lys Tyr Leu Lys Ser Ser Lys Tyr Met His Pro Trp
                325                 330                 335
Val Asn Lys Ile Glu Glu Gly Lys Leu Val Ile Trp Ile Asn Gly Asp
            340                 345                 350
Lys Gly Tyr Asn Gly Leu Ala Glu Val Gly Lys Lys Phe Glu Lys Asp
        355                 360                 365
Thr Gly Ile Lys Val Thr Val Glu His Pro Asp Lys Leu Glu Glu Lys
    370                 375                 380
Phe Pro Gln Val Ala Ala Thr Gly Asp Gly Pro Asp Ile Ile Phe Trp
385                 390                 395                 400
Ala His Asp Arg Phe Gly Gly Tyr Ala Gln Ser Gly Leu Leu Ala Glu
                405                 410                 415
Ile Thr Pro Asp Lys Ala Phe Gln Asp Lys Leu Tyr Pro Phe Thr Trp
            420                 425                 430
Asp Ala Val Arg Tyr Asn Gly Lys Leu Ile Ala Tyr Pro Ile Ala Val
        435                 440                 445
Glu Ala Leu Ser Leu Ile Tyr Asn Lys Asp Leu Leu Pro Asn Pro Pro
    450                 455                 460
Lys Thr Trp Glu Glu Ile Pro Ala Leu Asp Lys Glu Leu Lys Ala Lys
465                 470                 475                 480
Gly Lys Ser Ala Leu Met Phe Asn Leu Gln Glu Pro Tyr Phe Thr Trp
                485                 490                 495
Pro Leu Ile Ala Ala Asp Gly Gly Tyr Ala Phe Lys Tyr Glu Asn Gly
```

```
                500             505             510
Lys Tyr Asp Ile Lys Asp Val Gly Val Asp Asn Ala Gly Ala Lys Ala
            515                 520                 525

Gly Leu Thr Phe Leu Val Asp Leu Ile Lys Asn Lys His Met Asn Ala
            530                 535             540

Asp Thr Asp Tyr Ser Ile Ala Glu Ala Ala Phe Asn Lys Gly Glu Thr
545                 550                 555                 560

Ala Met Thr Ile Asn Gly Pro Trp Ala Trp Ser Asn Ile Asp Thr Ser
                565                 570                 575

Lys Val Asn Tyr Gly Val Thr Val Leu Pro Thr Phe Lys Gly Gln Pro
            580                 585                 590

Ser Lys Pro Phe Val Gly Val Leu Ser Ala Gly Ile Asn Ala Ala Ser
            595                 600                 605

Pro Asn Lys Glu Leu Ala Lys Glu Phe Leu Glu Asn Tyr Leu Leu Thr
            610                 615                 620

Asp Glu Gly Leu Glu Ala Val Asn Lys Asp Lys Pro Leu Gly Ala Val
625                 630                 635                 640

Ala Leu Lys Ser Tyr Glu Glu Glu Leu Ala Lys Asp Pro Arg Ile Ala
                645                 650                 655

Ala Thr Met Glu Asn Ala Gln Lys Gly Glu Ile Met Pro Asn Ile Pro
                660                 665                 670

Gln Met Ser Ala Phe Trp Tyr Ala Val Arg Thr Ala Val Ile Asn Ala
            675                 680                 685

Ala Ser Gly Arg Gln Thr Val Asp Glu Ala Asp Ile Val Asp Glu Phe
            690                 695                 700

Ser Asp Lys Ile Ile His Leu Thr Asp Asp Ser Phe Asp Thr Asp Val
705                 710                 715                 720

Leu Lys Ala Asp Gly Ala Ile Leu Val Asp Phe Trp Ala Glu Trp Cys
                725                 730                 735

Gly Pro Cys Lys Met Ile Ala Pro Ile Leu Asp Glu Ile Ala Asp Glu
            740                 745                 750

Tyr Gln Gly Lys Leu Thr Val Ala Lys Leu Asn Ile Asp Gln Asn Pro
            755                 760                 765

Gly Thr Ala Pro Lys Tyr Gly Ile Arg Gly Ile Pro Thr Leu Leu Leu
            770                 775                 780

Phe Lys Asn Gly Glu Val Ala Ala Thr Lys Val Gly Lys Leu Ala Ser
785                 790                 795                 800

Met Thr Gly Gly Gln Gln Met Gly Arg Asp Leu Tyr Asp Asp Asp Asp
                805                 810                 815

Lys Asp Arg Ser Ala Ala Gly Thr Met Glu Phe Ser Asp Lys Ile Ile
            820                 825                 830

His Leu Thr Asp Asp Ser Phe Asp Thr Asp Val Leu Lys Ala Asp Gly
            835                 840                 845

Ala Ile Leu Val Asp Phe Trp Ala Glu Trp Cys Gly Pro Cys Lys Met
850                 855                 860

Ile Ala Pro Ile Leu Asp Glu Ile Ala Asp Glu Tyr Gln Gly Lys Leu
865                 870                 875                 880

Thr Val Ala Lys Leu Asn Ile Asp Gln Asn Pro Gly Thr Ala Pro Lys
                885                 890                 895

Tyr Gly Ile Arg Gly Ile Pro Thr Leu Leu Leu Phe Lys Asn Gly Glu
            900                 905                 910

Val Ala Ala Thr Lys Val Gly Lys Leu
            915                 920
```

-continued

```
<210> SEQ ID NO 14
<211> LENGTH: 798
<212> TYPE: PRT
<213> ORGANISM: Artificial
<220> FEATURE:
<223> OTHER INFORMATION: Synthesized 120 kDa peptide
<220> FEATURE:
<221> NAME/KEY: PEPTIDE
<222> LOCATION: (1)..(798)

<400> SEQUENCE: 14

Met Arg Gly Ser His His His His His His Tyr Pro Tyr Asp Val Pro
 1               5                  10                  15

Asp Tyr Ala Asp Thr Tyr Arg Tyr Ile Met Ala Ser Met Thr Gly Gly
             20                  25                  30

Gln Gln Met Gly Ala Pro Val Pro Tyr Pro Asp Pro Leu Glu Pro Arg
         35                  40                  45

Tyr Thr Asp Ile Glu Met Asn Arg Leu Gly Lys Pro Ile Pro Asn Pro
     50                  55                  60

Leu Leu Gly Leu Asp Ser Thr Asp Phe Tyr Leu Lys Glu Thr Ala Ala
 65                  70                  75                  80

Ala Lys Phe Glu Arg Gln His Met Asp Ser Gln Pro Glu Leu Ala Pro
                 85                  90                  95

Glu Asp Pro Glu Asp Tyr Lys Asp Asp Asp Lys Cys Cys Pro Gly
            100                 105                 110

Cys Cys Glu Glu Glu Tyr Met Pro Met Glu Gln Lys Leu Ile Ser
        115                 120                 125

Glu Glu Asp Leu Leu Glu Met Ser Pro Ile Leu Gly Tyr Trp Lys Ile
    130                 135                 140

Lys Gly Leu Val Gln Pro Thr Arg Leu Leu Leu Glu Tyr Leu Glu Glu
145                 150                 155                 160

Lys Tyr Glu Glu His Leu Tyr Glu Arg Asp Glu Gly Asp Lys Trp Arg
                165                 170                 175

Asn Lys Lys Phe Glu Leu Gly Leu Glu Phe Pro Asn Leu Pro Tyr Tyr
            180                 185                 190

Ile Asp Gly Asp Val Lys Leu Thr Gln Ser Met Ala Ile Ile Arg Tyr
        195                 200                 205

Ile Ala Asp Lys His Asn Met Leu Gly Gly Cys Pro Lys Glu Arg Ala
    210                 215                 220

Glu Ile Ser Met Leu Glu Gly Ala Val Leu Asp Ile Arg Tyr Gly Val
225                 230                 235                 240

Ser Arg Ile Ala Tyr Ser Lys Asp Phe Glu Thr Leu Lys Val Asp Phe
                245                 250                 255

Leu Ser Lys Leu Pro Glu Met Leu Lys Met Phe Glu Asp Arg Leu Cys
            260                 265                 270

His Lys Thr Tyr Leu Asn Gly Asp His Val Thr His Pro Asp Phe Met
        275                 280                 285

Leu Tyr Asp Ala Leu Asp Val Val Leu Tyr Met Asp Pro Met Cys Leu
    290                 295                 300

Asp Ala Phe Pro Lys Leu Val Cys Phe Lys Arg Ile Glu Ala Ile
305                 310                 315                 320

Pro Gln Ile Asp Lys Tyr Leu Lys Ser Ser Lys Tyr Met His Pro Trp
                325                 330                 335

Val Asn Lys Ile Glu Glu Gly Lys Leu Val Ile Trp Ile Asn Gly Asp
            340                 345                 350
```

```
Lys Gly Tyr Asn Gly Leu Ala Glu Val Gly Lys Lys Phe Glu Lys Asp
        355                 360                 365

Thr Gly Ile Lys Val Thr Val Glu His Pro Asp Lys Leu Glu Glu Lys
    370                 375                 380

Phe Pro Gln Val Ala Ala Thr Gly Asp Gly Pro Asp Ile Ile Phe Trp
385                 390                 395                 400

Ala His Asp Arg Phe Gly Gly Tyr Ala Gln Ser Gly Leu Leu Ala Glu
                405                 410                 415

Ile Thr Pro Asp Lys Ala Phe Gln Asp Lys Leu Tyr Pro Phe Thr Trp
                420                 425                 430

Asp Ala Val Arg Tyr Asn Gly Lys Leu Ile Ala Tyr Pro Ile Ala Val
            435                 440                 445

Glu Ala Leu Ser Leu Ile Tyr Asn Lys Asp Leu Leu Pro Asn Pro Pro
    450                 455                 460

Lys Thr Trp Glu Glu Ile Pro Ala Leu Asp Lys Glu Leu Lys Ala Lys
465                 470                 475                 480

Gly Lys Ser Ala Leu Met Phe Asn Leu Gln Glu Pro Tyr Phe Thr Trp
                485                 490                 495

Pro Leu Ile Ala Ala Asp Gly Gly Tyr Ala Phe Lys Tyr Glu Asn Gly
                500                 505                 510

Lys Tyr Asp Ile Lys Asp Val Gly Val Asp Asn Ala Gly Ala Lys Ala
            515                 520                 525

Gly Leu Thr Phe Leu Val Asp Leu Ile Lys Asn Lys His Met Asn Ala
    530                 535                 540

Asp Thr Asp Tyr Ser Ile Ala Glu Ala Ala Phe Asn Lys Gly Glu Thr
545                 550                 555                 560

Ala Met Thr Ile Asn Gly Pro Trp Ala Trp Ser Asn Ile Asp Thr Ser
                565                 570                 575

Lys Val Asn Tyr Gly Val Thr Val Leu Pro Thr Phe Lys Gly Gln Pro
            580                 585                 590

Ser Lys Pro Phe Val Gly Val Leu Ser Ala Gly Ile Asn Ala Ala Ser
    595                 600                 605

Pro Asn Lys Glu Leu Ala Lys Glu Phe Leu Glu Asn Tyr Leu Leu Thr
610                 615                 620

Asp Glu Gly Leu Glu Ala Val Asn Lys Asp Lys Pro Leu Gly Ala Val
625                 630                 635                 640

Ala Leu Lys Ser Tyr Glu Glu Glu Leu Ala Lys Asp Pro Arg Ile Ala
                645                 650                 655

Ala Thr Met Glu Asn Ala Gln Lys Gly Glu Ile Met Pro Asn Ile Pro
                660                 665                 670

Gln Met Ser Ala Phe Trp Tyr Ala Val Arg Thr Ala Val Ile Asn Ala
            675                 680                 685

Ala Ser Gly Arg Gln Thr Val Asp Glu Ala Asp Ile Val Asp Glu Phe
    690                 695                 700

Ser Asp Lys Ile Ile His Leu Thr Asp Asp Ser Phe Asp Thr Asp Val
705                 710                 715                 720

Leu Lys Ala Asp Gly Ala Ile Leu Val Asp Phe Trp Ala Glu Trp Cys
                725                 730                 735

Gly Pro Cys Lys Met Ile Ala Pro Ile Leu Asp Glu Ile Ala Asp Glu
                740                 745                 750

Tyr Gln Gly Lys Leu Thr Val Ala Lys Leu Asn Ile Asp Gln Asn Pro
            755                 760                 765
```

```
Gly Thr Ala Pro Lys Tyr Gly Ile Arg Gly Ile Pro Thr Leu Leu Leu
        770                 775                 780

Phe Lys Asn Gly Glu Val Ala Ala Thr Lys Val Gly Lys Leu
785                 790                 795
```

<210> SEQ ID NO 15
<211> LENGTH: 1432
<212> TYPE: PRT
<213> ORGANISM: Artificial
<220> FEATURE:
<223> OTHER INFORMATION: Synthesized 160 kDa peptide
<220> FEATURE:
<221> NAME/KEY: PEPTIDE
<222> LOCATION: (1)..(1432)

<400> SEQUENCE: 15

```
Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
50                  55                  60

Leu Leu Gly Leu Asp Ser Thr Asp Phe Tyr Leu Lys Glu Thr Ala Ala
65                  70                  75                  80

Ala Lys Phe Glu Arg Gln His Met Asp Ser Gln Pro Glu Leu Ala Pro
            85                  90                  95

Glu Asp Pro Glu Asp Tyr Lys Asp Asp Asp Lys Cys Cys Pro Cys Gly
        100                 105                 110

Cys Cys Glu Glu Glu Glu Tyr Met Pro Met Glu Gln Lys Leu Ile Ser
            115                 120                 125

Glu Glu Asp Leu Leu Glu Met Ser Pro Ile Leu Gly Tyr Trp Lys Ile
        130                 135                 140

Lys Gly Leu Val Gln Pro Thr Arg Leu Leu Leu Glu Tyr Leu Glu Glu
145                 150                 155                 160

Lys Tyr Glu Glu His Leu Tyr Glu Arg Asp Glu Gly Asp Lys Trp Arg
                165                 170                 175

Asn Lys Lys Phe Glu Leu Gly Leu Glu Phe Pro Asn Leu Pro Tyr Tyr
            180                 185                 190

Ile Asp Gly Asp Val Lys Leu Thr Gln Ser Met Ala Ile Ile Arg Tyr
        195                 200                 205

Ile Ala Asp Lys His Asn Met Leu Gly Gly Cys Pro Lys Glu Arg Ala
    210                 215                 220

Glu Ile Ser Met Leu Glu Gly Ala Val Leu Asp Ile Arg Tyr Gly Val
225                 230                 235                 240

Ser Arg Ile Ala Tyr Ser Lys Asp Phe Glu Thr Leu Lys Val Asp Phe
                245                 250                 255

Leu Ser Lys Leu Pro Glu Met Leu Lys Met Phe Glu Asp Arg Leu Cys
            260                 265                 270

His Lys Thr Tyr Leu Asn Gly Asp His Val Thr His Pro Asp Phe Met
        275                 280                 285

Leu Tyr Asp Ala Leu Asp Val Val Leu Tyr Met Asp Pro Met Cys Leu
    290                 295                 300

Asp Ala Phe Pro Lys Leu Val Cys Phe Lys Lys Arg Ile Glu Ala Ile
305                 310                 315                 320
```

```
Pro Gln Ile Asp Lys Tyr Leu Lys Ser Ser Lys Tyr Met His Pro Trp
            325                 330                 335

Val Asn Lys Ile Glu Glu Gly Lys Leu Val Ile Trp Ile Asn Gly Asp
            340                 345                 350

Lys Gly Tyr Asn Gly Leu Ala Glu Val Gly Lys Lys Phe Glu Lys Asp
            355                 360                 365

Thr Gly Ile Lys Val Thr Val Glu His Pro Asp Lys Leu Glu Glu Lys
            370                 375                 380

Phe Pro Gln Val Ala Ala Thr Gly Asp Gly Pro Asp Ile Ile Phe Trp
385                 390                 395                 400

Ala His Asp Arg Phe Gly Gly Tyr Ala Gln Ser Gly Leu Leu Ala Glu
                405                 410                 415

Ile Thr Pro Asp Lys Ala Phe Gln Asp Lys Leu Tyr Pro Phe Thr Trp
            420                 425                 430

Asp Ala Val Arg Tyr Asn Gly Lys Leu Ile Ala Tyr Pro Ile Ala Val
            435                 440                 445

Glu Ala Leu Ser Leu Ile Tyr Asn Lys Asp Leu Leu Pro Asn Pro Pro
            450                 455                 460

Lys Thr Trp Glu Glu Ile Pro Ala Leu Asp Lys Glu Leu Lys Ala Lys
465                 470                 475                 480

Gly Lys Ser Ala Leu Met Phe Asn Leu Gln Glu Pro Tyr Phe Thr Trp
                485                 490                 495

Pro Leu Ile Ala Ala Asp Gly Gly Tyr Ala Phe Lys Tyr Glu Asn Gly
            500                 505                 510

Lys Tyr Asp Ile Lys Asp Val Gly Val Asp Asn Ala Gly Ala Lys Ala
            515                 520                 525

Gly Leu Thr Phe Leu Val Asp Leu Ile Lys Asn Lys His Met Asn Ala
            530                 535                 540

Asp Thr Asp Tyr Ser Ile Ala Glu Ala Ala Phe Asn Lys Gly Glu Thr
545                 550                 555                 560

Ala Met Thr Ile Asn Gly Pro Trp Ala Trp Ser Asn Ile Asp Thr Ser
                565                 570                 575

Lys Val Asn Tyr Gly Val Thr Val Leu Pro Thr Phe Lys Gly Gln Pro
            580                 585                 590

Ser Lys Pro Phe Val Gly Val Leu Ser Ala Gly Ile Asn Ala Ala Ser
            595                 600                 605

Pro Asn Lys Glu Leu Ala Lys Glu Phe Leu Glu Asn Tyr Leu Leu Thr
            610                 615                 620

Asp Glu Gly Leu Glu Ala Val Asn Lys Asp Lys Pro Leu Gly Ala Val
625                 630                 635                 640

Ala Leu Lys Ser Tyr Glu Glu Glu Leu Ala Lys Asp Pro Arg Ile Ala
                645                 650                 655

Ala Thr Met Glu Asn Ala Gln Lys Gly Glu Ile Met Pro Asn Ile Pro
            660                 665                 670

Gln Met Ser Ala Phe Trp Tyr Ala Val Arg Thr Ala Val Ile Asn Ala
            675                 680                 685

Ala Ser Gly Arg Gln Thr Val Asp Glu Ala Asp Ile Val Asp Met His
            690                 695                 700

Lys Ile Glu Glu Gly Lys Leu Val Ile Trp Ile Asn Gly Asp Lys Gly
705                 710                 715                 720

Tyr Asn Gly Leu Ala Glu Val Gly Lys Lys Phe Glu Lys Asp Thr Gly
                725                 730                 735

Ile Lys Val Thr Val Glu His Pro Asp Lys Leu Glu Glu Lys Phe Pro
```

-continued

```
                740                 745                 750
Gln Val Ala Ala Thr Gly Asp Gly Pro Asp Ile Ile Phe Trp Ala His
            755                 760                 765
Asp Arg Phe Gly Gly Tyr Ala Gln Ser Gly Leu Leu Ala Glu Ile Thr
        770                 775                 780
Pro Asp Lys Ala Phe Gln Asp Lys Leu Tyr Pro Phe Thr Trp Asp Ala
785                 790                 795                 800
Val Arg Tyr Asn Gly Lys Leu Ile Ala Tyr Pro Ile Ala Val Glu Ala
                805                 810                 815
Leu Ser Leu Ile Tyr Asn Lys Asp Leu Leu Pro Asn Pro Lys Thr
            820                 825                 830
Trp Glu Glu Ile Pro Ala Leu Asp Lys Glu Leu Lys Ala Lys Gly Lys
            835                 840                 845
Ser Ala Leu Met Phe Asn Leu Gln Glu Pro Tyr Phe Thr Trp Pro Pro
        850                 855                 860
Ile Ala Ala Asp Gly Gly Tyr Ala Phe Lys Tyr Glu Asn Gly Lys Tyr
865                 870                 875                 880
Asp Ile Lys Asp Val Gly Val Asp Asn Ala Gly Ala Lys Ala Gly Leu
                885                 890                 895
Thr Phe Leu Val Asp Leu Ile Lys Asn Lys His Met Asn Ala Asp Thr
            900                 905                 910
Asp Tyr Ser Ile Ala Glu Ala Ala Phe Asn Lys Gly Glu Thr Ala Met
        915                 920                 925
Thr Ile Asn Gly Pro Trp Ala Trp Ser Asn Ile Asp Thr Ser Lys Val
        930                 935                 940
Asn Tyr Gly Val Thr Val Leu Pro Thr Phe Lys Gly Gln Pro Ser Lys
945                 950                 955                 960
Pro Phe Val Gly Val Leu Ser Ala Gly Ile Asn Ala Ala Ser Pro Asn
                965                 970                 975
Lys Glu Leu Ala Lys Glu Phe Leu Glu Asn Tyr Leu Leu Thr Asp Glu
            980                 985                 990
Gly Leu Glu Ala Val Asn Lys Asp  Lys Pro Leu Gly Ala  Val Ala Leu
        995                 1000                1005
Lys Ser  Tyr Glu Glu Glu Leu  Ala Lys Asp Pro Arg  Ile Ala Ala
    1010                1015                1020
Thr Met  Glu Asn Ala Gln Lys  Gly Glu Ile Met Pro  Asn Ile Pro
    1025                1030                1035
Gln Met  Ser Ala Phe Trp Tyr  Ala Val Arg Thr Ala  Val Ile Asn
    1040                1045                1050
Ala Ala  Ser Gly Arg Gln Thr  Val Asp Glu Ala Val  Asn Lys Ile
    1055                1060                1065
Glu Glu  Gly Lys Leu Val Ile  Trp Ile Asn Gly Asp  Lys Gly Tyr
    1070                1075                1080
Asn Gly  Leu Ala Glu Val Gly  Lys Lys Phe Glu Lys  Asp Thr Gly
    1085                1090                1095
Ile Lys  Val Thr Val Glu His  Pro Asp Lys Leu Glu  Glu Lys Phe
    1100                1105                1110
Pro Gln  Val Ala Ala Thr Gly  Asp Gly Pro Asp Ile  Ile Phe Trp
    1115                1120                1125
Ala His  Asp Arg Phe Gly Gly  Tyr Ala Gln Ser Gly  Leu Leu Ala
    1130                1135                1140
Glu Ile  Thr Pro Asp Lys Ala  Phe Gln Asp Lys Leu  Tyr Pro Phe
    1145                1150                1155
```

```
Thr Trp Asp Ala Val Arg Tyr Asn Gly Lys Leu Ile Ala Tyr Pro
    1160                1165                1170

Ile Ala Val Glu Ala Leu Ser Leu Ile Tyr Asn Lys Asp Leu Leu
    1175                1180                1185

Pro Asn Pro Pro Lys Thr Trp Glu Glu Ile Pro Ala Leu Asp Lys
    1190                1195                1200

Glu Leu Lys Ala Lys Gly Lys Ser Ala Leu Met Phe Asn Leu Gln
    1205                1210                1215

Glu Pro Tyr Phe Thr Trp Pro Leu Ile Ala Ala Asp Gly Gly Tyr
    1220                1225                1230

Ala Phe Lys Tyr Glu Asn Gly Lys Tyr Asp Ile Lys Asp Val Gly
    1235                1240                1245

Val Asp Asn Ala Gly Ala Lys Ala Gly Leu Thr Phe Leu Val Asp
    1250                1255                1260

Leu Ile Lys Asn Lys His Met Asn Ala Asp Thr Asp Tyr Ser Ile
    1265                1270                1275

Ala Glu Ala Ala Phe Asn Lys Gly Glu Thr Ala Met Thr Ile Asn
    1280                1285                1290

Gly Pro Trp Ala Trp Ser Asn Ile Asp Thr Ser Lys Val Asn Tyr
    1295                1300                1305

Gly Val Thr Val Leu Pro Thr Phe Lys Gly Gln Pro Ser Lys Pro
    1310                1315                1320

Phe Val Gly Val Leu Ser Ala Gly Ile Asn Ala Ala Ser Pro Asn
    1325                1330                1335

Lys Glu Leu Ala Lys Glu Phe Leu Glu Asn Tyr Leu Leu Thr Asp
    1340                1345                1350

Glu Gly Leu Glu Ala Val Asn Lys Asp Lys Pro Leu Gly Ala Val
    1355                1360                1365

Ala Leu Lys Ser Tyr Glu Glu Glu Leu Ala Lys Asp Pro Arg Ile
    1370                1375                1380

Ala Ala Thr Met Glu Asn Ala Gln Lys Gly Glu Ile Met Pro Asn
    1385                1390                1395

Ile Pro Gln Met Ser Ala Phe Trp Tyr Ala Val Arg Thr Ala Val
    1400                1405                1410

Ile Asn Ala Ala Ser Gly Arg Gln Thr Val Asp Glu Ala Asp Ile
    1415                1420                1425

Pro Trp Lys Leu
    1430

<210> SEQ ID NO 16
<211> LENGTH: 1641
<212> TYPE: PRT
<213> ORGANISM: Artificial
<220> FEATURE:
<223> OTHER INFORMATION: Synthesized 180 kDa peptide
<220> FEATURE:
<221> NAME/KEY: PEPTIDE
<222> LOCATION: (1)..(1641)

<400> SEQUENCE: 16

Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45
```

-continued

```
Tyr Thr Asp Ile Glu Met Asn Arg Leu Gly Lys Pro Ile Pro Asn Pro
 50                  55                  60

Leu Leu Gly Leu Asp Ser Thr Asp Phe Tyr Leu Lys Glu Thr Ala Ala
 65                  70                  75                  80

Ala Lys Phe Glu Arg Gln His Met Asp Ser Gln Pro Glu Leu Ala Pro
                 85                  90                  95

Glu Asp Pro Glu Asp Tyr Lys Asp Asp Asp Lys Cys Cys Pro Gly
                100                 105                 110

Cys Cys Glu Glu Glu Glu Tyr Met Pro Met Glu Gln Lys Leu Ile Ser
                115                 120                 125

Glu Glu Asp Leu Leu Glu Met Ser Pro Ile Leu Gly Tyr Trp Lys Ile
130                 135                 140

Lys Gly Leu Val Gln Pro Thr Arg Leu Leu Leu Glu Tyr Leu Glu Glu
145                 150                 155                 160

Lys Tyr Glu Glu His Leu Tyr Glu Arg Asp Glu Gly Asp Lys Trp Arg
                165                 170                 175

Asn Lys Lys Phe Glu Leu Gly Leu Glu Phe Pro Asn Leu Pro Tyr Tyr
                180                 185                 190

Ile Asp Gly Asp Val Lys Leu Thr Gln Ser Met Ala Ile Ile Arg Tyr
                195                 200                 205

Ile Ala Asp Lys His Asn Met Leu Gly Gly Cys Pro Lys Glu Arg Ala
210                 215                 220

Glu Ile Ser Met Leu Glu Gly Ala Val Leu Asp Ile Arg Tyr Gly Val
225                 230                 235                 240

Ser Arg Ile Ala Tyr Ser Lys Asp Phe Glu Thr Leu Lys Val Asp Phe
                245                 250                 255

Leu Ser Lys Leu Pro Glu Met Leu Lys Met Phe Glu Asp Arg Leu Cys
                260                 265                 270

His Lys Thr Tyr Leu Asn Gly Asp His Val Thr His Pro Asp Phe Met
                275                 280                 285

Leu Tyr Asp Ala Leu Asp Val Val Leu Tyr Met Asp Pro Met Cys Leu
290                 295                 300

Asp Ala Phe Pro Lys Leu Val Cys Phe Lys Lys Arg Ile Glu Ala Ile
305                 310                 315                 320

Pro Gln Ile Asp Lys Tyr Leu Lys Ser Ser Lys Tyr Met His Lys Ile
                325                 330                 335

Glu Glu Gly Lys Leu Val Ile Trp Ile Asn Gly Asp Lys Gly Tyr Asn
                340                 345                 350

Gly Leu Ala Glu Val Gly Lys Lys Phe Glu Lys Asp Thr Gly Ile Lys
                355                 360                 365

Val Thr Val Glu His Pro Asp Lys Leu Glu Glu Lys Phe Pro Gln Val
370                 375                 380

Ala Ala Thr Gly Asp Gly Pro Asp Ile Ile Phe Trp Ala His Asp Arg
385                 390                 395                 400

Phe Gly Gly Tyr Ala Gln Ser Gly Leu Leu Ala Glu Ile Thr Pro Asp
                405                 410                 415

Lys Ala Phe Gln Asp Lys Leu Tyr Pro Phe Thr Trp Asp Ala Val Arg
                420                 425                 430

Tyr Asn Gly Lys Leu Ile Ala Tyr Pro Ile Ala Val Glu Ala Leu Ser
                435                 440                 445

Leu Ile Tyr Asn Lys Asp Leu Leu Pro Asn Pro Pro Lys Thr Trp Glu
450                 455                 460
```

Glu Ile Pro Ala Leu Asp Lys Glu Leu Lys Ala Lys Gly Lys Ser Ala
465                 470                 475                 480

Leu Met Phe Asn Leu Gln Glu Pro Tyr Phe Thr Trp Pro Pro Ile Ala
            485                 490                 495

Ala Asp Gly Gly Tyr Ala Phe Lys Tyr Glu Asn Gly Lys Tyr Asp Ile
        500                 505                 510

Lys Asp Val Gly Val Asp Asn Ala Gly Ala Lys Ala Gly Leu Thr Phe
    515                 520                 525

Leu Val Asp Leu Ile Lys Asn Lys His Met Asn Ala Asp Thr Asp Tyr
530                 535                 540

Ser Ile Ala Glu Ala Ala Phe Asn Lys Gly Glu Thr Ala Met Thr Ile
545                 550                 555                 560

Asn Gly Pro Trp Ala Trp Ser Asn Ile Asp Thr Ser Lys Val Asn Tyr
            565                 570                 575

Gly Val Thr Val Leu Pro Thr Phe Lys Gly Gln Pro Ser Lys Pro Phe
        580                 585                 590

Val Gly Val Leu Ser Ala Gly Ile Asn Ala Ala Ser Pro Asn Lys Glu
    595                 600                 605

Leu Ala Lys Glu Phe Leu Glu Asn Tyr Leu Leu Thr Asp Glu Gly Leu
610                 615                 620

Glu Ala Val Asn Lys Asp Lys Pro Leu Gly Ala Val Ala Leu Lys Ser
625                 630                 635                 640

Tyr Glu Glu Glu Leu Ala Lys Asp Pro Arg Ile Ala Ala Thr Met Glu
            645                 650                 655

Asn Ala Gln Lys Gly Glu Ile Met Pro Asn Ile Pro Gln Met Ser Ala
        660                 665                 670

Phe Trp Tyr Ala Val Arg Thr Ala Val Ile Asn Ala Ala Ser Gly Arg
    675                 680                 685

Gln Thr Val Asp Glu Ala Val Asn Lys Ile Glu Glu Gly Lys Leu Val
690                 695                 700

Ile Trp Ile Asn Gly Asp Lys Gly Tyr Asn Gly Leu Ala Glu Val Gly
705                 710                 715                 720

Lys Lys Phe Glu Lys Asp Thr Gly Ile Lys Val Thr Val Glu His Pro
            725                 730                 735

Asp Lys Leu Glu Glu Lys Phe Pro Gln Val Ala Ala Thr Gly Asp Gly
        740                 745                 750

Pro Asp Ile Ile Phe Trp Ala His Asp Arg Phe Gly Gly Tyr Ala Gln
    755                 760                 765

Ser Gly Leu Leu Ala Glu Ile Thr Pro Asp Lys Ala Phe Gln Asp Lys
770                 775                 780

Leu Tyr Pro Phe Thr Trp Asp Ala Val Arg Tyr Asn Gly Lys Leu Ile
785                 790                 795                 800

Ala Tyr Pro Ile Ala Val Glu Ala Leu Ser Leu Ile Tyr Asn Lys Asp
            805                 810                 815

Leu Leu Pro Asn Pro Pro Lys Thr Trp Glu Glu Ile Pro Ala Leu Asp
        820                 825                 830

Lys Glu Leu Lys Ala Lys Gly Lys Ser Ala Leu Met Phe Asn Leu Gln
835                 840                 845

Glu Pro Tyr Phe Thr Trp Pro Leu Ile Ala Ala Asp Gly Gly Tyr Ala
            850                 855                 860

Phe Lys Tyr Glu Asn Gly Lys Tyr Asp Ile Lys Asp Val Gly Val Asp
865                 870                 875                 880

Asn Ala Gly Ala Lys Ala Gly Leu Thr Phe Leu Val Asp Leu Ile Lys

```
                885                 890                 895
Asn Lys His Met Asn Ala Asp Thr Asp Tyr Ser Ile Ala Glu Ala Ala
            900                 905                 910
Phe Asn Lys Gly Glu Thr Ala Met Thr Ile Asn Gly Pro Trp Ala Trp
            915                 920                 925
Ser Asn Ile Asp Thr Ser Lys Val Asn Tyr Gly Val Thr Val Leu Pro
    930                 935                 940
Thr Phe Lys Gly Gln Pro Ser Lys Pro Phe Val Gly Val Leu Ser Ala
945                 950                 955                 960
Gly Ile Asn Ala Ala Ser Pro Asn Lys Glu Leu Ala Lys Glu Phe Leu
                965                 970                 975
Glu Asn Tyr Leu Leu Thr Asp Glu Gly Leu Glu Ala Val Asn Lys Asp
            980                 985                 990
Lys Pro Leu Gly Ala Val Ala Leu Lys Ser Tyr Glu Glu Glu Leu Ala
            995                 1000                1005
Lys Asp Pro Arg Ile Ala Ala Thr Met Glu Asn Ala Gln Lys Gly
    1010                1015                1020
Glu Ile Met Pro Asn Ile Pro Gln Met Ser Ala Phe Trp Tyr Ala
    1025                1030                1035
Val Arg Thr Ala Val Ile Asn Ala Ala Ser Gly Arg Gln Thr Val
    1040                1045                1050
Asp Glu Ala Asp Asn Lys Ile Glu Glu Gly Lys Leu Val Ile Trp
    1055                1060                1065
Ile Asn Gly Asp Lys Gly Tyr Asn Gly Leu Ala Glu Val Gly Lys
    1070                1075                1080
Lys Phe Glu Lys Asp Thr Gly Ile Lys Val Thr Val Glu His Pro
    1085                1090                1095
Asp Lys Leu Glu Glu Lys Phe Pro Gln Val Ala Ala Thr Gly Asp
    1100                1105                1110
Gly Pro Asp Ile Ile Phe Trp Ala His Asp Arg Phe Gly Gly Tyr
    1115                1120                1125
Ala Gln Ser Gly Leu Leu Ala Glu Ile Thr Pro Asp Lys Ala Phe
    1130                1135                1140
Gln Asp Lys Leu Tyr Pro Phe Thr Trp Asp Ala Val Arg Tyr Asn
    1145                1150                1155
Gly Lys Leu Ile Ala Tyr Pro Ile Ala Val Glu Ala Leu Ser Leu
    1160                1165                1170
Ile Tyr Asn Lys Asp Leu Leu Pro Asn Pro Pro Lys Thr Trp Glu
    1175                1180                1185
Glu Ile Pro Ala Leu Asp Lys Glu Leu Lys Ala Lys Gly Lys Ser
    1190                1195                1200
Ala Leu Met Phe Asn Leu Gln Glu Pro Tyr Phe Thr Trp Pro Leu
    1205                1210                1215
Ile Ala Ala Asp Gly Gly Tyr Ala Phe Lys Tyr Glu Asn Gly Lys
    1220                1225                1230
Tyr Asp Ile Lys Asp Val Gly Val Asp Asn Ala Gly Ala Lys Ala
    1235                1240                1245
Gly Leu Thr Phe Leu Val Asp Leu Ile Lys Asn Lys His Met Asn
    1250                1255                1260
Ala Asp Thr Asp Tyr Ser Ile Ala Glu Ala Ala Phe Asn Lys Gly
    1265                1270                1275
Glu Thr Ala Met Thr Ile Asn Gly Pro Trp Ala Trp Ser Asn Ile
    1280                1285                1290
```

```
Asp Thr Ser Lys Val Asn Tyr Gly Val Thr Val Leu Pro Thr Phe
    1295                1300                1305

Lys Gly Gln Pro Ser Lys Pro Phe Val Gly Val Leu Ser Ala Gly
    1310                1315                1320

Ile Asn Ala Ala Ser Pro Asn Lys Glu Leu Ala Lys Glu Phe Leu
    1325                1330                1335

Glu Asn Tyr Leu Leu Thr Asp Glu Gly Leu Glu Ala Val Asn Lys
    1340                1345                1350

Asp Lys Pro Leu Gly Ala Val Ala Leu Lys Ser Tyr Glu Glu Glu
    1355                1360                1365

Leu Ala Lys Asp Pro Arg Ile Ala Ala Thr Met Glu Asn Ala Gln
    1370                1375                1380

Lys Gly Glu Ile Met Pro Asn Ile Pro Gln Met Ser Ala Phe Trp
    1385                1390                1395

Tyr Ala Val Arg Thr Ala Val Ile Asn Ala Ala Ser Gly Arg Gln
    1400                1405                1410

Thr Val Asp Glu Ala Asp Ile Val Asp Glu Phe Ser Asp Lys Ile
    1415                1420                1425

Ile His Leu Thr Asp Asp Ser Phe Asp Thr Asp Val Leu Lys Ala
    1430                1435                1440

Asp Gly Ala Ile Leu Val Asp Phe Trp Ala Glu Trp Cys Gly Pro
    1445                1450                1455

Cys Lys Met Ile Ala Pro Ile Leu Asp Glu Ile Ala Asp Glu Tyr
    1460                1465                1470

Gln Gly Lys Leu Thr Val Ala Lys Leu Asn Ile Asp Gln Asn Pro
    1475                1480                1485

Gly Thr Ala Pro Lys Tyr Gly Ile Arg Gly Ile Pro Thr Leu Leu
    1490                1495                1500

Leu Phe Lys Asn Gly Glu Val Ala Ala Thr Lys Val Gly Lys Leu
    1505                1510                1515

Ala Ser Met Thr Gly Gly Gln Gln Met Gly Arg Asp Leu Tyr Asp
    1520                1525                1530

Asp Asp Asp Lys Asp Arg Ser Ala Ala Gly Thr Met Glu Phe Ser
    1535                1540                1545

Asp Lys Ile Ile His Leu Thr Asp Asp Ser Phe Asp Thr Asp Val
    1550                1555                1560

Leu Lys Ala Asp Gly Ala Ile Leu Val Asp Phe Trp Ala Glu Trp
    1565                1570                1575

Cys Gly Pro Cys Lys Met Ile Ala Pro Ile Leu Asp Glu Ile Ala
    1580                1585                1590

Asp Glu Tyr Gln Gly Lys Leu Thr Val Ala Lys Leu Asn Ile Asp
    1595                1600                1605

Gln Asn Pro Gly Thr Ala Pro Lys Tyr Gly Ile Arg Gly Ile Pro
    1610                1615                1620

Thr Leu Leu Leu Phe Lys Asn Gly Glu Val Ala Ala Thr Lys Val
    1625                1630                1635

Gly Lys Leu
    1640

<210> SEQ ID NO 17
<211> LENGTH: 1790
<212> TYPE: PRT
<213> ORGANISM: Artificial
<220> FEATURE:
```

<223> OTHER INFORMATION: Synthesized 200 kDa peptide
<220> FEATURE:
<221> NAME/KEY: PEPTIDE
<222> LOCATION: (1)..(1790)

<400> SEQUENCE: 17

```
Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
    50                  55                  60

Leu Leu Gly Leu Asp Ser Thr Asp Phe Tyr Leu Lys Glu Thr Ala Ala
65                  70                  75                  80

Ala Lys Phe Glu Arg Gln His Met Asp Ser Gln Pro Glu Leu Ala Pro
                85                  90                  95

Glu Asp Pro Glu Asp Tyr Lys Asp Asp Asp Lys Cys Cys Pro Gly
            100                 105                 110

Cys Cys Glu Glu Glu Tyr Met Pro Met Gln Lys Leu Ile Ser
            115                 120                 125

Glu Glu Asp Leu Leu Glu Met Ser Pro Ile Leu Gly Tyr Trp Lys Ile
    130                 135                 140

Lys Gly Leu Val Gln Pro Thr Arg Leu Leu Leu Glu Tyr Leu Glu Glu
145                 150                 155                 160

Lys Tyr Glu Glu His Leu Tyr Glu Arg Asp Gly Asp Lys Trp Arg
                165                 170                 175

Asn Lys Lys Phe Glu Leu Gly Leu Glu Phe Pro Asn Leu Pro Tyr Tyr
            180                 185                 190

Ile Asp Gly Asp Val Lys Leu Thr Gln Ser Met Ala Ile Ile Arg Tyr
        195                 200                 205

Ile Ala Asp Lys His Asn Met Leu Gly Gly Cys Pro Lys Glu Arg Ala
210                 215                 220

Glu Ile Ser Met Leu Glu Gly Ala Val Leu Asp Ile Arg Tyr Gly Val
225                 230                 235                 240

Ser Arg Ile Ala Tyr Ser Lys Asp Phe Glu Thr Leu Lys Val Asp Phe
                245                 250                 255

Leu Ser Lys Leu Pro Glu Met Leu Lys Met Phe Glu Asp Arg Leu Cys
            260                 265                 270

His Lys Thr Tyr Leu Asn Gly Asp His Val Thr His Pro Asp Phe Met
        275                 280                 285

Leu Tyr Asp Ala Leu Asp Val Val Leu Tyr Met Asp Pro Met Cys Leu
    290                 295                 300

Asp Ala Phe Pro Lys Leu Val Cys Phe Lys Lys Arg Ile Glu Ala Ile
305                 310                 315                 320

Pro Gln Ile Asp Lys Tyr Leu Lys Ser Ser Lys Tyr Met His Lys Ile
                325                 330                 335

Glu Glu Gly Lys Leu Val Ile Trp Ile Asn Gly Asp Lys Gly Tyr Asn
            340                 345                 350

Gly Leu Ala Glu Val Gly Lys Lys Phe Glu Lys Asp Thr Gly Ile Lys
        355                 360                 365

Val Thr Val Glu His Pro Asp Lys Leu Glu Glu Lys Phe Pro Gln Val
    370                 375                 380
```

-continued

```
Ala Ala Thr Gly Asp Gly Pro Asp Ile Ile Phe Trp Ala His Asp Arg
385                 390                 395                 400

Phe Gly Gly Tyr Ala Gln Ser Gly Leu Leu Ala Glu Ile Thr Pro Asp
            405                 410                 415

Lys Ala Phe Gln Asp Lys Leu Tyr Pro Phe Thr Trp Asp Ala Val Arg
        420                 425                 430

Tyr Asn Gly Lys Leu Ile Ala Tyr Pro Ile Ala Val Glu Ala Leu Ser
    435                 440                 445

Leu Ile Tyr Asn Lys Asp Leu Leu Pro Asn Pro Lys Thr Trp Glu
450                 455                 460

Glu Ile Pro Ala Leu Asp Lys Glu Leu Lys Ala Lys Gly Lys Ser Ala
465                 470                 475                 480

Leu Met Phe Asn Leu Gln Glu Pro Tyr Phe Thr Trp Pro Pro Ile Ala
            485                 490                 495

Ala Asp Gly Gly Tyr Ala Phe Lys Tyr Glu Asn Gly Lys Tyr Asp Ile
        500                 505                 510

Lys Asp Val Gly Val Asp Asn Ala Gly Ala Lys Ala Gly Leu Thr Phe
    515                 520                 525

Leu Val Asp Leu Ile Lys Asn Lys His Met Asn Ala Asp Thr Asp Tyr
530                 535                 540

Ser Ile Ala Glu Ala Ala Phe Asn Lys Gly Glu Thr Ala Met Thr Ile
545                 550                 555                 560

Asn Gly Pro Trp Ala Trp Ser Asn Ile Asp Thr Ser Lys Val Asn Tyr
            565                 570                 575

Gly Val Thr Val Leu Pro Thr Phe Lys Gly Gln Pro Ser Lys Pro Phe
        580                 585                 590

Val Gly Val Leu Ser Ala Gly Ile Asn Ala Ala Ser Pro Asn Lys Glu
    595                 600                 605

Leu Ala Lys Glu Phe Leu Glu Asn Tyr Leu Leu Thr Asp Glu Gly Leu
610                 615                 620

Glu Ala Val Asn Lys Asp Lys Pro Leu Gly Ala Val Ala Leu Lys Ser
625                 630                 635                 640

Tyr Glu Glu Glu Leu Ala Lys Asp Pro Arg Ile Ala Ala Thr Met Glu
            645                 650                 655

Asn Ala Gln Lys Gly Glu Ile Met Pro Asn Ile Pro Gln Met Ser Ala
        660                 665                 670

Phe Trp Tyr Ala Val Arg Thr Ala Val Ile Asn Ala Ala Ser Gly Arg
    675                 680                 685

Gln Thr Val Asp Glu Ala Val Asn Lys Ile Glu Glu Gly Lys Leu Val
690                 695                 700

Ile Trp Ile Asn Gly Asp Lys Gly Tyr Asn Gly Leu Ala Glu Val Gly
705                 710                 715                 720

Lys Lys Phe Glu Lys Asp Thr Gly Ile Lys Val Thr Val Glu His Pro
            725                 730                 735

Asp Lys Leu Glu Glu Lys Phe Pro Gln Val Ala Ala Thr Gly Asp Gly
        740                 745                 750

Pro Asp Ile Ile Phe Trp Ala His Asp Arg Phe Gly Gly Tyr Ala Gln
    755                 760                 765

Ser Gly Leu Leu Ala Glu Ile Thr Pro Asp Lys Ala Phe Gln Asp Lys
770                 775                 780

Leu Tyr Pro Phe Thr Trp Asp Ala Val Arg Tyr Asn Gly Lys Leu Ile
785                 790                 795                 800

Ala Tyr Pro Ile Ala Val Glu Ala Leu Ser Leu Ile Tyr Asn Lys Asp
```

```
                  805                 810                 815
Leu Leu Pro Asn Pro Lys Thr Trp Glu Glu Ile Pro Ala Leu Asp
              820                 825                 830

Lys Glu Leu Lys Ala Lys Gly Lys Ser Ala Leu Met Phe Asn Leu Gln
              835                 840                 845

Glu Pro Tyr Phe Thr Trp Pro Leu Ile Ala Ala Asp Gly Gly Tyr Ala
850               855                 860

Phe Lys Tyr Glu Asn Gly Lys Tyr Asp Ile Lys Asp Val Gly Val Asp
865               870                 875                 880

Asn Ala Gly Ala Lys Ala Gly Leu Thr Phe Leu Val Asp Leu Ile Lys
                  885                 890                 895

Asn Lys His Met Asn Ala Asp Thr Asp Tyr Ser Ile Ala Glu Ala Ala
              900                 905                 910

Phe Asn Lys Gly Glu Thr Ala Met Thr Ile Asn Gly Pro Trp Ala Trp
              915                 920                 925

Ser Asn Ile Asp Thr Ser Lys Val Asn Tyr Gly Val Thr Val Leu Pro
              930                 935                 940

Thr Phe Lys Gly Gln Pro Ser Lys Pro Phe Val Gly Val Leu Ser Ala
945               950                 955                 960

Gly Ile Asn Ala Ala Ser Pro Asn Lys Glu Leu Ala Lys Glu Phe Leu
                  965                 970                 975

Glu Asn Tyr Leu Leu Thr Asp Glu Gly Leu Glu Ala Val Asn Lys Asp
              980                 985                 990

Lys Pro Leu Gly Ala Val Ala Leu Lys Ser Tyr Glu Glu Glu Leu Ala
              995                 1000                1005

Lys Asp Pro Arg Ile Ala Ala Thr Met Glu Asn Ala Gln Lys Gly
    1010                1015                1020

Glu Ile Met Pro Asn Ile Pro Gln Met Ser Ala Phe Trp Tyr Ala
    1025                1030                1035

Val Arg Thr Ala Val Ile Asn Ala Ala Ser Gly Arg Gln Thr Val
    1040                1045                1050

Asp Glu Ala Asp Ile Val Asp Met His Lys Ile Glu Glu Gly Lys
    1055                1060                1065

Leu Val Ile Trp Ile Asn Gly Asp Lys Gly Tyr Asn Gly Leu Ala
    1070                1075                1080

Glu Val Gly Lys Lys Phe Glu Lys Asp Thr Gly Ile Lys Val Thr
    1085                1090                1095

Val Glu His Pro Asp Lys Leu Glu Glu Lys Phe Pro Gln Val Ala
    1100                1105                1110

Ala Thr Gly Asp Gly Pro Asp Ile Ile Phe Trp Ala His Asp Arg
    1115                1120                1125

Phe Gly Gly Tyr Ala Gln Ser Gly Leu Leu Ala Glu Ile Thr Pro
    1130                1135                1140

Asp Lys Ala Phe Gln Asp Lys Leu Tyr Pro Phe Thr Trp Asp Ala
    1145                1150                1155

Val Arg Tyr Asn Gly Lys Leu Ile Ala Tyr Pro Ile Ala Val Glu
    1160                1165                1170

Ala Leu Ser Leu Ile Tyr Asn Lys Asp Leu Leu Pro Asn Pro Pro
    1175                1180                1185

Lys Thr Trp Glu Glu Ile Pro Ala Leu Asp Lys Glu Leu Lys Ala
    1190                1195                1200

Lys Gly Lys Ser Ala Leu Met Phe Asn Leu Gln Glu Pro Tyr Phe
    1205                1210                1215
```

```
Thr Trp Pro Pro Ile Ala Ala Asp Gly Gly Tyr Ala Phe Lys Tyr
1220            1225                1230

Glu Asn Gly Lys Tyr Asp Ile Lys Asp Val Gly Val Asp Asn Ala
1235            1240                1245

Gly Ala Lys Ala Gly Leu Thr Phe Leu Val Asp Leu Ile Lys Asn
1250            1255                1260

Lys His Met Asn Ala Asp Thr Asp Tyr Ser Ile Ala Glu Ala Ala
1265            1270                1275

Phe Asn Lys Gly Glu Thr Ala Met Thr Ile Asn Gly Pro Trp Ala
1280            1285                1290

Trp Ser Asn Ile Asp Thr Ser Lys Val Asn Tyr Gly Val Thr Val
1295            1300                1305

Leu Pro Thr Phe Lys Gly Gln Pro Ser Lys Pro Phe Val Gly Val
1310            1315                1320

Leu Ser Ala Gly Ile Asn Ala Ala Ser Pro Asn Lys Glu Leu Ala
1325            1330                1335

Lys Glu Phe Leu Glu Asn Tyr Leu Leu Thr Asp Glu Gly Leu Glu
1340            1345                1350

Ala Val Asn Lys Asp Lys Pro Leu Gly Ala Val Ala Leu Lys Ser
1355            1360                1365

Tyr Glu Glu Glu Leu Ala Lys Asp Pro Arg Ile Ala Ala Thr Met
1370            1375                1380

Glu Asn Ala Gln Lys Gly Glu Ile Met Pro Asn Ile Pro Gln Met
1385            1390                1395

Ser Ala Phe Trp Tyr Ala Val Arg Thr Ala Val Ile Asn Ala Ala
1400            1405                1410

Ser Gly Arg Gln Thr Val Asp Glu Ala Val Asn Lys Ile Glu Glu
1415            1420                1425

Gly Lys Leu Val Ile Trp Ile Asn Gly Asp Lys Gly Tyr Asn Gly
1430            1435                1440

Leu Ala Glu Val Gly Lys Lys Phe Glu Lys Asp Thr Gly Ile Lys
1445            1450                1455

Val Thr Val Glu His Pro Asp Lys Leu Glu Glu Lys Phe Pro Gln
1460            1465                1470

Val Ala Ala Thr Gly Asp Gly Pro Asp Ile Ile Phe Trp Ala His
1475            1480                1485

Asp Arg Phe Gly Gly Tyr Ala Gln Ser Gly Leu Leu Ala Glu Ile
1490            1495                1500

Thr Pro Asp Lys Ala Phe Gln Asp Lys Leu Tyr Pro Phe Thr Trp
1505            1510                1515

Asp Ala Val Arg Tyr Asn Gly Lys Leu Ile Ala Tyr Pro Ile Ala
1520            1525                1530

Val Glu Ala Leu Ser Leu Ile Tyr Asn Lys Asp Leu Leu Pro Asn
1535            1540                1545

Pro Pro Lys Thr Trp Glu Glu Ile Pro Ala Leu Asp Lys Glu Leu
1550            1555                1560

Lys Ala Lys Gly Lys Ser Ala Leu Met Phe Asn Leu Gln Glu Pro
1565            1570                1575

Tyr Phe Thr Trp Pro Leu Ile Ala Ala Asp Gly Gly Tyr Ala Phe
1580            1585                1590

Lys Tyr Glu Asn Gly Lys Tyr Asp Ile Lys Asp Val Gly Val Asp
1595            1600                1605
```

```
Asn Ala Gly Ala Lys Ala Gly Leu Thr Phe Leu Val Asp Leu Ile
    1610                1615                1620

Lys Asn Lys His Met Asn Ala Asp Thr Asp Tyr Ser Ile Ala Glu
    1625                1630                1635

Ala Ala Phe Asn Lys Gly Glu Thr Ala Met Thr Ile Asn Gly Pro
    1640                1645                1650

Trp Ala Trp Ser Asn Ile Asp Thr Ser Lys Val Asn Tyr Gly Val
    1655                1660                1665

Thr Val Leu Pro Thr Phe Lys Gly Gln Pro Ser Lys Pro Phe Val
    1670                1675                1680

Gly Val Leu Ser Ala Gly Ile Asn Ala Ala Ser Pro Asn Lys Glu
    1685                1690                1695

Leu Ala Lys Glu Phe Leu Glu Asn Tyr Leu Leu Thr Asp Glu Gly
    1700                1705                1710

Leu Glu Ala Val Asn Lys Asp Lys Pro Leu Gly Ala Val Ala Leu
    1715                1720                1725

Lys Ser Tyr Glu Glu Glu Leu Ala Lys Asp Pro Arg Ile Ala Ala
    1730                1735                1740

Thr Met Glu Asn Ala Gln Lys Gly Glu Ile Met Pro Asn Ile Pro
    1745                1750                1755

Gln Met Ser Ala Phe Trp Tyr Ala Val Arg Thr Ala Val Ile Asn
    1760                1765                1770

Ala Ala Ser Gly Arg Gln Thr Val Asp Glu Ala Asp Ile Pro Trp
    1775                1780                1785

Lys Leu
    1790

<210> SEQ ID NO 18
<211> LENGTH: 2152
<212> TYPE: PRT
<213> ORGANISM: Artificial
<220> FEATURE:
<223> OTHER INFORMATION: Synthesized 240 kDa peptide
<220> FEATURE:
<221> NAME/KEY: PEPTIDE
<222> LOCATION: (1)..(2152)

<400> SEQUENCE: 18

Met Arg Gly Ser His His His His His His Tyr Pro Tyr Asp Val Pro
1               5                   10                  15

Asp Tyr Ala Asp Thr Tyr Arg Tyr Ile Met Ala Ser Met Thr Gly Gly
            20                  25                  30

Gln Gln Met Gly Ala Pro Val Pro Tyr Pro Asp Pro Leu Glu Pro Arg
        35                  40                  45

Tyr Thr Asp Ile Glu Met Asn Arg Leu Gly Lys Pro Ile Pro Asn Pro
    50                  55                  60

Leu Leu Gly Leu Asp Ser Thr Asp Phe Tyr Leu Lys Glu Thr Ala Ala
65                  70                  75                  80

Ala Lys Phe Glu Arg Gln His Met Asp Ser Gln Pro Glu Leu Ala Pro
            85                  90                  95

Glu Asp Pro Glu Asp Tyr Lys Asp Asp Asp Lys Cys Cys Pro Gly
            100                 105                 110

Cys Cys Glu Glu Glu Glu Tyr Met Pro Met Glu Gln Lys Leu Ile Ser
        115                 120                 125

Glu Glu Asp Leu Leu Glu Met Ser Pro Ile Leu Gly Tyr Trp Lys Ile
    130                 135                 140
```

```
Lys Gly Leu Val Gln Pro Thr Arg Leu Leu Leu Glu Tyr Leu Glu Glu
145                 150                 155                 160

Lys Tyr Glu Glu His Leu Tyr Glu Arg Asp Glu Gly Asp Lys Trp Arg
                165                 170                 175

Asn Lys Lys Phe Glu Leu Gly Leu Glu Phe Pro Asn Leu Pro Tyr Tyr
            180                 185                 190

Ile Asp Gly Asp Val Lys Leu Thr Gln Ser Met Ala Ile Ile Arg Tyr
        195                 200                 205

Ile Ala Asp Lys His Asn Met Leu Gly Gly Cys Pro Lys Glu Arg Ala
    210                 215                 220

Glu Ile Ser Met Leu Glu Gly Ala Val Leu Asp Ile Arg Tyr Gly Val
225                 230                 235                 240

Ser Arg Ile Ala Tyr Ser Lys Asp Phe Glu Thr Leu Lys Val Asp Phe
                245                 250                 255

Leu Ser Lys Leu Pro Glu Met Leu Lys Met Phe Glu Asp Arg Leu Cys
            260                 265                 270

His Lys Thr Tyr Leu Asn Gly Asp His Val Thr His Pro Asp Phe Met
        275                 280                 285

Leu Tyr Asp Ala Leu Asp Val Val Leu Tyr Met Asp Pro Met Cys Leu
    290                 295                 300

Asp Ala Phe Pro Lys Leu Val Cys Phe Lys Lys Arg Ile Glu Ala Ile
305                 310                 315                 320

Pro Gln Ile Asp Lys Tyr Leu Lys Ser Ser Lys Tyr Met His Lys Ile
                325                 330                 335

Glu Glu Gly Lys Leu Val Ile Trp Ile Asn Gly Asp Lys Gly Tyr Asn
            340                 345                 350

Gly Leu Ala Glu Val Gly Lys Lys Phe Glu Lys Asp Thr Gly Ile Lys
        355                 360                 365

Val Thr Val Glu His Pro Asp Lys Leu Glu Glu Lys Phe Pro Gln Val
    370                 375                 380

Ala Ala Thr Gly Asp Gly Pro Asp Ile Ile Phe Trp Ala His Asp Arg
385                 390                 395                 400

Phe Gly Gly Tyr Ala Gln Ser Gly Leu Leu Ala Glu Ile Thr Pro Asp
                405                 410                 415

Lys Ala Phe Gln Asp Lys Leu Tyr Pro Phe Thr Trp Asp Ala Val Arg
            420                 425                 430

Tyr Asn Gly Lys Leu Ile Ala Tyr Pro Ile Ala Val Glu Ala Leu Ser
        435                 440                 445

Leu Ile Tyr Asn Lys Asp Leu Leu Pro Asn Pro Pro Lys Thr Trp Glu
450                 455                 460

Glu Ile Pro Ala Leu Asp Lys Glu Leu Lys Ala Lys Gly Lys Ser Ala
465                 470                 475                 480

Leu Met Phe Asn Leu Gln Glu Pro Tyr Phe Thr Trp Pro Leu Ile Ala
                485                 490                 495

Ala Asp Gly Gly Tyr Ala Phe Lys Tyr Glu Asn Gly Lys Tyr Asp Ile
            500                 505                 510

Lys Asp Val Gly Val Asp Asn Ala Gly Ala Lys Ala Gly Leu Thr Phe
        515                 520                 525

Leu Val Asp Leu Ile Lys Asn Lys His Met Asn Ala Asp Thr Asp Tyr
    530                 535                 540

Ser Ile Ala Glu Ala Ala Phe Asn Lys Gly Glu Thr Ala Met Thr Ile
545                 550                 555                 560

Asn Gly Pro Trp Ala Trp Ser Asn Ile Asp Thr Ser Lys Val Asn Tyr
```

```
            565                 570                 575
Gly Val Thr Val Leu Pro Thr Phe Lys Gly Gln Pro Ser Lys Pro Phe
                580                 585                 590

Val Gly Val Leu Ser Ala Gly Ile Asn Ala Ala Ser Pro Asn Lys Glu
                595                 600                 605

Leu Ala Lys Glu Phe Leu Glu Asn Tyr Leu Leu Thr Asp Glu Gly Leu
            610                 615                 620

Glu Ala Val Asn Lys Asp Lys Pro Leu Gly Ala Val Ala Leu Lys Ser
625                 630                 635                 640

Tyr Glu Glu Leu Ala Lys Asp Pro Arg Ile Ala Ala Thr Met Glu
                645                 650                 655

Asn Ala Gln Lys Gly Glu Ile Met Pro Asn Ile Pro Gln Met Ser Ala
                660                 665                 670

Phe Trp Tyr Ala Val Arg Thr Ala Val Ile Asn Ala Ala Ser Gly Arg
            675                 680                 685

Gln Thr Val Asp Glu Ala Val Asn Lys Ile Glu Glu Gly Lys Leu Val
            690                 695                 700

Ile Trp Ile Asn Gly Asp Lys Gly Tyr Asn Gly Leu Ala Glu Val Gly
705                 710                 715                 720

Lys Lys Phe Glu Lys Asp Thr Gly Ile Lys Val Thr Val Glu His Pro
                725                 730                 735

Asp Lys Leu Glu Glu Lys Phe Pro Gln Val Ala Ala Thr Gly Asp Gly
                740                 745                 750

Pro Asp Ile Ile Phe Trp Ala His Asp Arg Phe Gly Gly Tyr Ala Gln
            755                 760                 765

Ser Gly Leu Leu Ala Glu Ile Thr Pro Asp Lys Ala Phe Gln Asp Lys
            770                 775                 780

Leu Tyr Pro Phe Thr Trp Asp Ala Val Arg Tyr Asn Gly Lys Leu Ile
785                 790                 795                 800

Ala Tyr Pro Ile Ala Val Glu Ala Leu Ser Leu Ile Tyr Asn Lys Asp
                805                 810                 815

Leu Leu Pro Asn Pro Pro Lys Thr Trp Glu Glu Ile Pro Ala Leu Asp
            820                 825                 830

Lys Glu Leu Lys Ala Lys Gly Lys Ser Ala Leu Met Phe Asn Leu Gln
            835                 840                 845

Glu Pro Tyr Phe Thr Trp Pro Leu Ile Ala Ala Asp Gly Gly Tyr Ala
            850                 855                 860

Phe Lys Tyr Glu Asn Gly Lys Tyr Asp Ile Lys Asp Val Gly Val Asp
865                 870                 875                 880

Asn Ala Gly Ala Lys Ala Gly Leu Thr Phe Leu Val Asp Leu Ile Lys
                885                 890                 895

Asn Lys His Met Asn Ala Asp Thr Asp Tyr Ser Ile Ala Glu Ala Ala
                900                 905                 910

Phe Asn Lys Gly Glu Thr Ala Met Thr Ile Asn Gly Pro Trp Ala Trp
            915                 920                 925

Ser Asn Ile Asp Thr Ser Lys Val Asn Tyr Gly Val Thr Val Leu Pro
            930                 935                 940

Thr Phe Lys Gly Gln Pro Ser Lys Pro Phe Val Gly Val Leu Ser Ala
945                 950                 955                 960

Gly Ile Asn Ala Ala Ser Pro Asn Lys Glu Leu Ala Lys Glu Phe Leu
                965                 970                 975

Glu Asn Tyr Leu Leu Thr Asp Glu Gly Leu Glu Ala Val Asn Lys Asp
            980                 985                 990
```

```
Lys Pro Leu Gly Ala Val Ala Leu  Lys Ser Tyr Glu Glu  Glu Leu Ala
        995                1000                1005

Lys Asp  Pro Arg Ile Ala Ala  Thr Met Glu Asn Ala  Gln Lys Gly
    1010                1015                1020

Glu Ile  Met Pro Asn Ile Pro  Gln Met Ser Ala Phe  Trp Tyr Ala
    1025                1030                1035

Val Arg  Thr Ala Val Ile Asn  Ala Ala Ser Gly Arg  Gln Thr Val
    1040                1045                1050

Asp Glu  Ala Asp Asn Lys Ile  Glu Glu Gly Lys Leu  Val Ile Trp
    1055                1060                1065

Ile Asn  Gly Asp Lys Gly Tyr  Asn Gly Leu Ala Glu  Val Gly Lys
    1070                1075                1080

Lys Phe  Glu Lys Asp Thr Gly  Ile Lys Val Thr Val  Glu His Pro
    1085                1090                1095

Asp Lys  Leu Glu Glu Lys Phe  Pro Gln Val Ala Ala  Thr Gly Asp
    1100                1105                1110

Gly Pro  Asp Ile Ile Phe Trp  Ala His Asp Arg Phe  Gly Gly Tyr
    1115                1120                1125

Ala Gln  Ser Gly Leu Leu Ala  Glu Ile Thr Pro Asp  Lys Ala Phe
    1130                1135                1140

Gln Asp  Lys Leu Tyr Pro Phe  Thr Trp Asp Ala Val  Arg Tyr Asn
    1145                1150                1155

Gly Lys  Leu Ile Ala Tyr Pro  Ile Ala Val Glu Ala  Leu Ser Leu
    1160                1165                1170

Ile Tyr  Asn Lys Asp Leu Leu  Pro Asn Pro Pro Lys  Thr Trp Glu
    1175                1180                1185

Glu Ile  Pro Ala Leu Asp Lys  Glu Leu Lys Ala Lys  Gly Lys Ser
    1190                1195                1200

Ala Leu  Met Phe Asn Leu Gln  Glu Pro Tyr Phe Thr  Trp Pro Leu
    1205                1210                1215

Ile Ala  Ala Asp Gly Gly Tyr  Ala Phe Lys Tyr Glu  Asn Gly Lys
    1220                1225                1230

Tyr Asp  Ile Lys Asp Val Gly  Val Asp Asn Ala Gly  Ala Lys Ala
    1235                1240                1245

Gly Leu  Thr Phe Leu Val Asp  Leu Ile Lys Asn Lys  His Met Asn
    1250                1255                1260

Ala Asp  Thr Asp Tyr Ser Ile  Ala Glu Ala Ala Phe  Asn Lys Gly
    1265                1270                1275

Glu Thr  Ala Met Thr Ile Asn  Gly Pro Trp Ala Trp  Ser Asn Ile
    1280                1285                1290

Asp Thr  Ser Lys Val Asn Tyr  Gly Val Thr Val Leu  Pro Thr Phe
    1295                1300                1305

Lys Gly  Gln Pro Ser Lys Pro  Phe Val Gly Val Leu  Ser Ala Gly
    1310                1315                1320

Ile Asn  Ala Ala Ser Pro Asn  Lys Glu Leu Ala Lys  Glu Phe Leu
    1325                1330                1335

Glu Asn  Tyr Leu Leu Thr Asp  Glu Gly Leu Glu Ala  Val Asn Lys
    1340                1345                1350

Asp Lys  Pro Leu Gly Ala Val  Ala Leu Lys Ser Tyr  Glu Glu Glu
    1355                1360                1365

Leu Ala  Lys Asp Pro Arg Ile  Ala Ala Thr Met Glu  Asn Ala Gln
    1370                1375                1380
```

-continued

```
Lys Gly Glu Ile Met Pro Asn Ile Pro Gln Met Ser Ala Phe Trp
    1385                1390                1395

Tyr Ala Val Arg Thr Ala Val Ile Asn Ala Ala Ser Gly Arg Gln
    1400                1405                1410

Thr Val Asp Glu Ala Asp Ile Val Asp Met His Lys Ile Glu Glu
    1415                1420                1425

Gly Lys Leu Val Ile Trp Ile Asn Gly Asp Lys Gly Tyr Asn Gly
    1430                1435                1440

Leu Ala Glu Val Gly Lys Lys Phe Glu Lys Asp Thr Gly Ile Lys
    1445                1450                1455

Val Thr Val Glu His Pro Asp Lys Leu Glu Glu Lys Phe Pro Gln
    1460                1465                1470

Val Ala Ala Thr Gly Asp Gly Pro Asp Ile Ile Phe Trp Ala His
    1475                1480                1485

Asp Arg Phe Gly Gly Tyr Ala Gln Ser Gly Leu Leu Ala Glu Ile
    1490                1495                1500

Thr Pro Asp Lys Ala Phe Gln Asp Lys Leu Tyr Pro Phe Thr Trp
    1505                1510                1515

Asp Ala Val Arg Tyr Asn Gly Lys Leu Ile Ala Tyr Pro Ile Ala
    1520                1525                1530

Val Glu Ala Leu Ser Leu Ile Tyr Asn Lys Asp Leu Leu Pro Asn
    1535                1540                1545

Pro Pro Lys Thr Trp Glu Glu Ile Pro Ala Leu Asp Lys Glu Leu
    1550                1555                1560

Lys Ala Lys Gly Lys Ser Ala Leu Met Phe Asn Leu Gln Glu Pro
    1565                1570                1575

Tyr Phe Thr Trp Pro Pro Ile Ala Ala Asp Gly Gly Tyr Ala Phe
    1580                1585                1590

Lys Tyr Glu Asn Gly Lys Tyr Asp Ile Lys Asp Val Gly Val Asp
    1595                1600                1605

Asn Ala Gly Ala Lys Ala Gly Leu Thr Phe Leu Val Asp Leu Ile
    1610                1615                1620

Lys Asn Lys His Met Asn Ala Asp Thr Asp Tyr Ser Ile Ala Glu
    1625                1630                1635

Ala Ala Phe Asn Lys Gly Glu Thr Ala Met Thr Ile Asn Gly Pro
    1640                1645                1650

Trp Ala Trp Ser Asn Ile Asp Thr Ser Lys Val Asn Tyr Gly Val
    1655                1660                1665

Thr Val Leu Pro Thr Phe Lys Gly Gln Pro Ser Lys Pro Phe Val
    1670                1675                1680

Gly Val Leu Ser Ala Gly Ile Asn Ala Ala Ser Pro Asn Lys Glu
    1685                1690                1695

Leu Ala Lys Glu Phe Leu Glu Asn Tyr Leu Leu Thr Asp Glu Gly
    1700                1705                1710

Leu Glu Ala Val Asn Lys Asp Lys Pro Leu Gly Ala Val Ala Leu
    1715                1720                1725

Lys Ser Tyr Glu Glu Glu Leu Ala Lys Asp Pro Arg Ile Ala Ala
    1730                1735                1740

Thr Met Glu Asn Ala Gln Lys Gly Glu Ile Met Pro Asn Ile Pro
    1745                1750                1755

Gln Met Ser Ala Phe Trp Tyr Ala Val Arg Thr Ala Val Ile Asn
    1760                1765                1770

Ala Ala Ser Gly Arg Gln Thr Val Asp Glu Ala Val Asn Lys Ile
```

```
        1775                1780                1785
Glu Glu Gly Lys Leu Val Ile Trp Ile Asn Gly Asp Lys Gly Tyr
        1790                1795                1800
Asn Gly Leu Ala Glu Val Gly Lys Lys Phe Glu Lys Asp Thr Gly
        1805                1810                1815
Ile Lys Val Thr Val Glu His Pro Asp Lys Leu Glu Glu Lys Phe
        1820                1825                1830
Pro Gln Val Ala Ala Thr Gly Asp Gly Pro Asp Ile Ile Phe Trp
        1835                1840                1845
Ala His Asp Arg Phe Gly Gly Tyr Ala Gln Ser Gly Leu Leu Ala
        1850                1855                1860
Glu Ile Thr Pro Asp Lys Ala Phe Gln Asp Lys Leu Tyr Pro Phe
        1865                1870                1875
Thr Trp Asp Ala Val Arg Tyr Asn Gly Lys Leu Ile Ala Tyr Pro
        1880                1885                1890
Ile Ala Val Glu Ala Leu Ser Leu Ile Tyr Asn Lys Asp Leu Leu
        1895                1900                1905
Pro Asn Pro Pro Lys Thr Trp Glu Glu Ile Pro Ala Leu Asp Lys
        1910                1915                1920
Glu Leu Lys Ala Lys Gly Lys Ser Ala Leu Met Phe Asn Leu Gln
        1925                1930                1935
Glu Pro Tyr Phe Thr Trp Pro Leu Ile Ala Ala Asp Gly Gly Tyr
        1940                1945                1950
Ala Phe Lys Tyr Glu Asn Gly Lys Tyr Asp Ile Lys Asp Val Gly
        1955                1960                1965
Val Asp Asn Ala Gly Ala Lys Ala Gly Leu Thr Phe Leu Val Asp
        1970                1975                1980
Leu Ile Lys Asn Lys His Met Asn Ala Asp Thr Asp Tyr Ser Ile
        1985                1990                1995
Ala Glu Ala Ala Phe Asn Lys Gly Glu Thr Ala Met Thr Ile Asn
        2000                2005                2010
Gly Pro Trp Ala Trp Ser Asn Ile Asp Thr Ser Lys Val Asn Tyr
        2015                2020                2025
Gly Val Thr Val Leu Pro Thr Phe Lys Gly Gln Pro Ser Lys Pro
        2030                2035                2040
Phe Val Gly Val Leu Ser Ala Gly Ile Asn Ala Ala Ser Pro Asn
        2045                2050                2055
Lys Glu Leu Ala Lys Glu Phe Leu Glu Asn Tyr Leu Leu Thr Asp
        2060                2065                2070
Glu Gly Leu Glu Ala Val Asn Lys Asp Lys Pro Leu Gly Ala Val
        2075                2080                2085
Ala Leu Lys Ser Tyr Glu Glu Glu Leu Ala Lys Asp Pro Arg Ile
        2090                2095                2100
Ala Ala Thr Met Glu Asn Ala Gln Lys Gly Glu Ile Met Pro Asn
        2105                2110                2115
Ile Pro Gln Met Ser Ala Phe Trp Tyr Ala Val Arg Thr Ala Val
        2120                2125                2130
Ile Asn Ala Ala Ser Gly Arg Gln Thr Val Asp Glu Ala Asp Ile
        2135                2140                2145
Pro Trp Lys Leu
        2150

<210> SEQ ID NO 19
```

```
<211> LENGTH: 6
<212> TYPE: PRT
<213> ORGANISM: Artificial
<220> FEATURE:
<223> OTHER INFORMATION: Synthesized His-tag peptide
<220> FEATURE:
<221> NAME/KEY: PEPTIDE
<222> LOCATION: (1)..(6)

<400> SEQUENCE: 19

His His His His His His
1               5

<210> SEQ ID NO 20
<211> LENGTH: 18
<212> TYPE: DNA
<213> ORGANISM: Artificial
<220> FEATURE:
<223> OTHER INFORMATION: Synthesized His-tag DNA
<220> FEATURE:
<221> NAME/KEY: misc_feature
<222> LOCATION: (1)..(18)

<400> SEQUENCE: 20
catcatcatc atcatcat                                                        18

<210> SEQ ID NO 21
<211> LENGTH: 10
<212> TYPE: PRT
<213> ORGANISM: Artificial
<220> FEATURE:
<223> OTHER INFORMATION: Synthesized c-Myc-tag peptide
<220> FEATURE:
<221> NAME/KEY: PEPTIDE
<222> LOCATION: (1)..(10)

<400> SEQUENCE: 21

Glu Gln Lys Leu Ile Ser Glu Glu Asp Leu
1               5                   10

<210> SEQ ID NO 22
<211> LENGTH: 30
<212> TYPE: DNA
<213> ORGANISM: Artificial
<220> FEATURE:
<223> OTHER INFORMATION: Synthesized c-Myc-tag DNA
<220> FEATURE:
<221> NAME/KEY: misc_feature
<222> LOCATION: (1)..(30)

<400> SEQUENCE: 22
gaacaaaaac tcatctcaga agaggatctg                                           30

<210> SEQ ID NO 23
<211> LENGTH: 9
<212> TYPE: PRT
<213> ORGANISM: Artificial
<220> FEATURE:
<223> OTHER INFORMATION: Synthesized HA-tag peptide
<220> FEATURE:
<221> NAME/KEY: PEPTIDE
<222> LOCATION: (1)..(9)

<400> SEQUENCE: 23

Tyr Pro Tyr Asp Val Pro Asp Tyr Ala
1               5

<210> SEQ ID NO 24
<211> LENGTH: 27
```

```
<212> TYPE: DNA
<213> ORGANISM: Artificial
<220> FEATURE:
<223> OTHER INFORMATION: Synthesized HA-tag DNA
<220> FEATURE:
<221> NAME/KEY: misc_feature
<222> LOCATION: (1)..(27)

<400> SEQUENCE: 24
tatccatatg atgttccaga ttatgct                                         27

<210> SEQ ID NO 25
<211> LENGTH: 15
<212> TYPE: PRT
<213> ORGANISM: Artificial
<220> FEATURE:
<223> OTHER INFORMATION: Synthesized S-tag paptide
<220> FEATURE:
<221> NAME/KEY: PEPTIDE
<222> LOCATION: (1)..(15)

<400> SEQUENCE: 25

Lys Glu Thr Ala Ala Ala Lys Phe Glu Arg Gln His Met Asp Ser
1               5                   10                  15

<210> SEQ ID NO 26
<211> LENGTH: 45
<212> TYPE: DNA
<213> ORGANISM: Artificial
<220> FEATURE:
<223> OTHER INFORMATION: Synthesized S-tag DNA
<220> FEATURE:
<221> NAME/KEY: misc_feature
<222> LOCATION: (1)..(45)

<400> SEQUENCE: 26
aaagaaaccg ctgctgctaa attcgaacgc cagcacatgg acagc                     45

<210> SEQ ID NO 27
<211> LENGTH: 8
<212> TYPE: PRT
<213> ORGANISM: Artificial
<220> FEATURE:
<223> OTHER INFORMATION: Synthesized Flag-tag peptide
<220> FEATURE:
<221> NAME/KEY: PEPTIDE
<222> LOCATION: (1)..(8)

<400> SEQUENCE: 27

Asp Tyr Lys Asp Asp Asp Asp Lys
1               5

<210> SEQ ID NO 28
<211> LENGTH: 24
<212> TYPE: DNA
<213> ORGANISM: Artificial
<220> FEATURE:
<223> OTHER INFORMATION: Synthesized Flag-tag DNA
<220> FEATURE:
<221> NAME/KEY: misc_feature
<222> LOCATION: (1)..(24)

<400> SEQUENCE: 28
gattacaagg atgacgacga taag                                            24

<210> SEQ ID NO 29
<211> LENGTH: 14
<212> TYPE: PRT
<213> ORGANISM: Artificial
```

```
<220> FEATURE:
<223> OTHER INFORMATION: Synthesized V5-tag peptide
<220> FEATURE:
<221> NAME/KEY: PEPTIDE
<222> LOCATION: (1)..(14)

<400> SEQUENCE: 29

Gly Lys Pro Ile Pro Asn Pro Leu Leu Gly Leu Asp Ser Thr
1               5                   10

<210> SEQ ID NO 30
<211> LENGTH: 42
<212> TYPE: DNA
<213> ORGANISM: Artificial
<220> FEATURE:
<223> OTHER INFORMATION: Synthesized V5-tag DNA
<220> FEATURE:
<221> NAME/KEY: misc_feature
<222> LOCATION: (1)..(42)

<400> SEQUENCE: 30
ggtaagccta tccctaaccc tctcctcggt ctcgattcta cg                    42

<210> SEQ ID NO 31
<211> LENGTH: 11
<212> TYPE: PRT
<213> ORGANISM: Artificial
<220> FEATURE:
<223> OTHER INFORMATION: Synthesized T7-tag peptide
<220> FEATURE:
<221> NAME/KEY: PEPTIDE
<222> LOCATION: (1)..(11)

<400> SEQUENCE: 31

Met Ala Ser Met Thr Gly Gly Gln Gln Met Gly
1               5                   10

<210> SEQ ID NO 32
<211> LENGTH: 13
<212> TYPE: PRT
<213> ORGANISM: Artificial
<220> FEATURE:
<223> OTHER INFORMATION: Synthesized E-tag peptide
<220> FEATURE:
<221> NAME/KEY: PEPTIDE
<222> LOCATION: (1)..(13)

<400> SEQUENCE: 32

Gly Ala Pro Val Pro Tyr Pro Asp Pro Leu Glu Pro Arg
1               5                   10

<210> SEQ ID NO 33
<211> LENGTH: 39
<212> TYPE: DNA
<213> ORGANISM: Artificial
<220> FEATURE:
<223> OTHER INFORMATION: Synthesized E-tag DNA
<220> FEATURE:
<221> NAME/KEY: misc_feature
<222> LOCATION: (1)..(39)

<400> SEQUENCE: 33
ggtgcgccgg tgccgtatcc ggatccgctg gaaccgcgt                        39

<210> SEQ ID NO 34
<211> LENGTH: 11
<212> TYPE: PRT
<213> ORGANISM: Artificial
<220> FEATURE:
```

```
<223> OTHER INFORMATION: Synthesized VSV-g-tag peptide
<220> FEATURE:
<221> NAME/KEY: PEPTIDE
<222> LOCATION: (1)..(11)

<400> SEQUENCE: 34

Tyr Thr Asp Ile Glu Met Asn Arg Leu Gly Lys
1               5                   10

<210> SEQ ID NO 35
<211> LENGTH: 33
<212> TYPE: DNA
<213> ORGANISM: Artificial
<220> FEATURE:
<223> OTHER INFORMATION: Synthesized VSV-g-tag DNA
<220> FEATURE:
<221> NAME/KEY: misc_feature
<222> LOCATION: (1)..(33)

<400> SEQUENCE: 35
tacaccgaca tcgagatgaa ccggttgggc aag                                 33

<210> SEQ ID NO 36
<211> LENGTH: 12
<212> TYPE: PRT
<213> ORGANISM: Artificial
<220> FEATURE:
<223> OTHER INFORMATION: Synthesized HSV-tag peptide
<220> FEATURE:
<221> NAME/KEY: PEPTIDE
<222> LOCATION: (1)..(12)

<400> SEQUENCE: 36

Ser Gln Pro Glu Leu Ala Pro Glu Asp Pro Glu Asp
1               5                   10

<210> SEQ ID NO 37
<211> LENGTH: 36
<212> TYPE: DNA
<213> ORGANISM: Artificial
<220> FEATURE:
<223> OTHER INFORMATION: Synthesized HSV-tag DNA
<220> FEATURE:
<221> NAME/KEY: misc_feature
<222> LOCATION: (1)..(36)

<400> SEQUENCE: 37
agccagccag aactcgctcc tgaagaccca gaggat                              36

<210> SEQ ID NO 38
<211> LENGTH: 6
<212> TYPE: PRT
<213> ORGANISM: Artificial
<220> FEATURE:
<223> OTHER INFORMATION: Synthesized Lumio-tag peptide
<220> FEATURE:
<221> NAME/KEY: PEPTIDE
<222> LOCATION: (1)..(6)

<400> SEQUENCE: 38

Cys Cys Pro Gly Cys Cys
1               5

<210> SEQ ID NO 39
<211> LENGTH: 18
<212> TYPE: DNA
<213> ORGANISM: Artificial
<220> FEATURE:
<223> OTHER INFORMATION: Synthesized Lumio-tag DNA
```

```
<220> FEATURE:
<221> NAME/KEY: misc_feature
<222> LOCATION: (1)..(18)

<400> SEQUENCE: 39
tgttgtcctg gctgttgc                                                   18

<210> SEQ ID NO 40
<211> LENGTH: 10
<212> TYPE: PRT
<213> ORGANISM: Artificial
<220> FEATURE:
<223> OTHER INFORMATION: Synthesized Glu-Glu-tag peptide
<220> FEATURE:
<221> NAME/KEY: PEPTIDE
<222> LOCATION: (1)..(10)

<400> SEQUENCE: 40

Cys Glu Glu Glu Glu Tyr Met Pro Met Glu
1               5                   10

<210> SEQ ID NO 41
<211> LENGTH: 30
<212> TYPE: DNA
<213> ORGANISM: Artificial
<220> FEATURE:
<223> OTHER INFORMATION: Synthesized Glu-Glu-tag DNA
<220> FEATURE:
<221> NAME/KEY: misc_feature
<222> LOCATION: (1)..(30)

<400> SEQUENCE: 41
tgtgaagaag aagaatacat gccgatggaa                                      30

<210> SEQ ID NO 42
<211> LENGTH: 6
<212> TYPE: PRT
<213> ORGANISM: Artificial
<220> FEATURE:
<223> OTHER INFORMATION: Synthesized AU1-tag peptide
<220> FEATURE:
<221> NAME/KEY: PEPTIDE
<222> LOCATION: (1)..(6)

<400> SEQUENCE: 42

Asp Thr Tyr Arg Tyr Ile
1               5

<210> SEQ ID NO 43
<211> LENGTH: 18
<212> TYPE: DNA
<213> ORGANISM: Artificial
<220> FEATURE:
<223> OTHER INFORMATION: Synthesized AU1-tag DNA
<220> FEATURE:
<221> NAME/KEY: misc_feature
<222> LOCATION: (1)..(18)

<400> SEQUENCE: 43
gacacctacc gttacatc                                                   18

<210> SEQ ID NO 44
<211> LENGTH: 6
<212> TYPE: PRT
<213> ORGANISM: Artificial
<220> FEATURE:
<223> OTHER INFORMATION: Synthesized AU5-tag peptide
<220> FEATURE:
<221> NAME/KEY: PEPTIDE
```

-continued

<222> LOCATION: (1)..(6)

<400> SEQUENCE: 44

Thr Asp Phe Tyr Leu Lys
1               5

<210> SEQ ID NO 45
<211> LENGTH: 18
<212> TYPE: DNA
<213> ORGANISM: Artificial
<220> FEATURE:
<223> OTHER INFORMATION: Synthesized AU5-tag DNA
<220> FEATURE:
<221> NAME/KEY: misc_feature
<222> LOCATION: (1)..(18)

<400> SEQUENCE: 45
accgacttct acctgaag                                                    18

<210> SEQ ID NO 46
<211> LENGTH: 57
<212> TYPE: DNA
<213> ORGANISM: Artificial
<220> FEATURE:
<223> OTHER INFORMATION: Synthesized P1 primer
<220> FEATURE:
<221> NAME/KEY: misc_feature
<222> LOCATION: (1)..(57)

<400> SEQUENCE: 46
ggaacgccat atgcaccatc atcatcatca ttatccttac gatgttccag attatgc        57

<210> SEQ ID NO 47
<211> LENGTH: 40
<212> TYPE: DNA
<213> ORGANISM: Artificial
<220> FEATURE:
<223> OTHER INFORMATION: Synthesized P1 new primer
<220> FEATURE:
<221> NAME/KEY: misc_feature
<222> LOCATION: (1)..(40)

<400> SEQUENCE: 47
ggaattccat atgcggggtt ctcatcatca tcatcatcat                            40

<210> SEQ ID NO 48
<211> LENGTH: 57
<212> TYPE: DNA
<213> ORGANISM: Artificial
<220> FEATURE:
<223> OTHER INFORMATION: Synthesized P2-A primer
<220> FEATURE:
<221> NAME/KEY: misc_feature
<222> LOCATION: (1)..(57)

<400> SEQUENCE: 48
ccaccagtca tactggccat gatgtaacgg taggtgtcag cataatctgg aacatcg        57

<210> SEQ ID NO 49
<211> LENGTH: 57
<212> TYPE: DNA
<213> ORGANISM: Artificial
<220> FEATURE:
<223> OTHER INFORMATION: Synthesized P3 primer
<220> FEATURE:
<221> NAME/KEY: misc_feature
<222> LOCATION: (1)..(57)

<400> SEQUENCE: 49
ggccagtatg actggtggac agcaaatggg tgcgccggtg ccgtatccgg acccact            57

<210> SEQ ID NO 50
<211> LENGTH: 57
<212> TYPE: DNA
<213> ORGANISM: Artificial
<220> FEATURE:
<223> OTHER INFORMATION: Synthesized P4-A primer
<220> FEATURE:
<221> NAME/KEY: misc_feature
<222> LOCATION: (1)..(57)

<400> SEQUENCE: 50
cccaaccggt tcatctcgat gtcggtgtaa cgcggttcca gtgggtccgg atacggc            57

<210> SEQ ID NO 51
<211> LENGTH: 57
<212> TYPE: DNA
<213> ORGANISM: Artificial
<220> FEATURE:
<223> OTHER INFORMATION: Synthesized P5 primer
<220> FEATURE:
<221> NAME/KEY: misc_feature
<222> LOCATION: (1)..(57)

<400> SEQUENCE: 51
cgagatgaac cggttgggca agcctatccc taaccctctc ctcggtctcg attctac            57

<210> SEQ ID NO 52
<211> LENGTH: 57
<212> TYPE: DNA
<213> ORGANISM: Artificial
<220> FEATURE:
<223> OTHER INFORMATION: Synthesized P6-A primer
<220> FEATURE:
<221> NAME/KEY: misc_feature
<222> LOCATION: (1)..(57)

<400> SEQUENCE: 52
tcaaatttag cagcagcggt ttccttcagg tagaagtccg tagaatcgag accgagg            57

<210> SEQ ID NO 53
<211> LENGTH: 57
<212> TYPE: DNA
<213> ORGANISM: Artificial
<220> FEATURE:
<223> OTHER INFORMATION: Synthesized P7 primer
<220> FEATURE:
<221> NAME/KEY: misc_feature
<222> LOCATION: (1)..(57)

<400> SEQUENCE: 53
cgctgctgct aaatttgagc gccagcacat ggacagccag ccagaactcg ctcctga            57

<210> SEQ ID NO 54
<211> LENGTH: 57
<212> TYPE: DNA
<213> ORGANISM: Artificial
<220> FEATURE:
<223> OTHER INFORMATION: Synthesized P8-A primer
<220> FEATURE:
<221> NAME/KEY: misc_feature
<222> LOCATION: (1)..(57)

<400> SEQUENCE: 54
caacacttat cgtcgtcatc cttgtaatcc tctgggtctt caggagcgag ttctggc            57

```
<210> SEQ ID NO 55
<211> LENGTH: 57
<212> TYPE: DNA
<213> ORGANISM: Artificial
<220> FEATURE:
<223> OTHER INFORMATION: Synthesized P9 primer
<220> FEATURE:
<221> NAME/KEY: misc_feature
<222> LOCATION: (1)..(57)

<400> SEQUENCE: 55
tgacgacgat aagtgttgtc ctggctgttg cgaagaagaa gaatacatgc cgatgga        57

<210> SEQ ID NO 56
<211> LENGTH: 58
<212> TYPE: DNA
<213> ORGANISM: Artificial
<220> FEATURE:
<223> OTHER INFORMATION: Synthesized P10-A primer
<220> FEATURE:
<221> NAME/KEY: misc_feature
<222> LOCATION: (1)..(58)

<400> SEQUENCE: 56
ctagctagct cacagatcct cttctgagat gagtttttgt tccatcggca tgtattct       58

<210> SEQ ID NO 57
<211> LENGTH: 58
<212> TYPE: DNA
<213> ORGANISM: Artificial
<220> FEATURE:
<223> OTHER INFORMATION: Synthesized P10-A reverse primer
<220> FEATURE:
<221> NAME/KEY: misc_feature
<222> LOCATION: (1)..(58)

<400> SEQUENCE: 57
agaatacatg ccgatggaac aaaaactcat ctcagaagag gatctgtgag ctagctag       58

<210> SEQ ID NO 58
<211> LENGTH: 57
<212> TYPE: DNA
<213> ORGANISM: Artificial
<220> FEATURE:
<223> OTHER INFORMATION: Synthesized P11-A primer
<220> FEATURE:
<221> NAME/KEY: misc_feature
<222> LOCATION: (1)..(57)

<400> SEQUENCE: 58
ctagctagcg tacgattggg taagtttaac atcacccctcg agcagatcct cttctga       57

<210> SEQ ID NO 59
<211> LENGTH: 57
<212> TYPE: DNA
<213> ORGANISM: Artificial
<220> FEATURE:
<223> OTHER INFORMATION: Synthesized P11-A reverse primer
<220> FEATURE:
<221> NAME/KEY: misc_feature
<222> LOCATION: (1)..(57)

<400> SEQUENCE: 59
tcagaagagg atctgctcga gggtgatgtt aaacttaccc aatcgtacgc tagctag        57

<210> SEQ ID NO 60
<211> LENGTH: 24
<212> TYPE: DNA
<213> ORGANISM: Artificial
```

```
<220> FEATURE:
<223> OTHER INFORMATION: Synthesized GST-P1 primer
<220> FEATURE:
<221> NAME/KEY: misc_feature
<222> LOCATION: (1)..(24)

<400> SEQUENCE: 60
ctcgagatgt ccctatact aggt                                          24

<210> SEQ ID NO 61
<211> LENGTH: 59
<212> TYPE: DNA
<213> ORGANISM: Artificial
<220> FEATURE:
<223> OTHER INFORMATION: Synthesized GST-P2-A primer
<220> FEATURE:
<221> NAME/KEY: misc_feature
<222> LOCATION: (1)..(59)

<400> SEQUENCE: 61
gctagctcag aattcgtcga cgatatcgtt aacccatgga tgcatatact tgctggatt   59

<210> SEQ ID NO 62
<211> LENGTH: 58
<212> TYPE: DNA
<213> ORGANISM: Artificial
<220> FEATURE:
<223> OTHER INFORMATION: Synthesized MBP1-P1
<220> FEATURE:
<221> NAME/KEY: misc_feature
<222> LOCATION: (1)..(58)

<400> SEQUENCE: 62
gtcgacatgc ataaaatcga agaaggtaaa ctggtaatct ggattaacgg cgataaag    58

<210> SEQ ID NO 63
<211> LENGTH: 58
<212> TYPE: DNA
<213> ORGANISM: Artificial
<220> FEATURE:
<223> OTHER INFORMATION: Synthesized MBP1-P2-A primer
<220> FEATURE:
<221> NAME/KEY: misc_feature
<222> LOCATION: (1)..(58)

<400> SEQUENCE: 63
gttaacggct tcatcgacag tctgacgacc gctggcggcg ttgatcaccg cagtacgc    58

<210> SEQ ID NO 64
<211> LENGTH: 57
<212> TYPE: DNA
<213> ORGANISM: Artificial
<220> FEATURE:
<223> OTHER INFORMATION: Synthesized MBP2-P1 primer
<220> FEATURE:
<221> NAME/KEY: misc_feature
<222> LOCATION: (1)..(57)

<400> SEQUENCE: 64
gttaacaaaa tcgaagaagg taaactggta atctggatta acggcgataa aggctat     57

<210> SEQ ID NO 65
<211> LENGTH: 58
<212> TYPE: DNA
<213> ORGANISM: Artificial
<220> FEATURE:
<223> OTHER INFORMATION: Synthesized MBP2-P2-A primer
<220> FEATURE:
<221> NAME/KEY: misc_feature
```

```
<222> LOCATION: (1)..(58)

<400> SEQUENCE: 65
ctgcaggtcg acgatatcct aaagcttcca tgggatatcg gcttcatcga cagtctga       58

<210> SEQ ID NO 66
<211> LENGTH: 52
<212> TYPE: DNA
<213> ORGANISM: Artificial
<220> FEATURE:
<223> OTHER INFORMATION: Synthesized TRX-P1 primer
<220> FEATURE:
<221> NAME/KEY: misc_feature
<222> LOCATION: (1)..(52)

<400> SEQUENCE: 66
gtcgacgaat tcagcgataa aattattcac ctgactgacg acagttttga ca             52

<210> SEQ ID NO 67
<211> LENGTH: 50
<212> TYPE: DNA
<213> ORGANISM: Artificial
<220> FEATURE:
<223> OTHER INFORMATION: Synthesized TRX-P2-A primer
<220> FEATURE:
<221> NAME/KEY: misc_feature
<222> LOCATION: (1)..(50)

<400> SEQUENCE: 67
gctagcaagc ttacccactt tggttgccgc cacttcaccg tttttgaaca                50

<210> SEQ ID NO 68
<211> LENGTH: 33
<212> TYPE: DNA
<213> ORGANISM: Artificial
<220> FEATURE:
<223> OTHER INFORMATION: Synthesized T7-tag DNA
<220> FEATURE:
<221> NAME/KEY: misc_feature
<222> LOCATION: (1)..(33)

<400> SEQUENCE: 68
atggctagca tgactggtgg acagcaaatg ggt                                  33
```